United States Patent
Slaney et al.

(10) Patent No.: US 6,278,028 B1
(45) Date of Patent: Aug. 21, 2001

(54) LIQUID CRYSTAL COMPOUNDS, MIXTURES AND DEVICES

(75) Inventors: Andrew John Slaney; Damien Gerard McDonnell; Amarjit Kaur Samra; Maurice Stanley; Victoria Minter, all of Malvern; John William Goodby, Hull; Michael Hird, Hull; Simon John Cross, Hull; Chu Chuan Dong, Hull, all of (GB)

(73) Assignee: The Secretary of State for in Defence in Her Brittanic Majesty's Government of the United Kingdom of Great Britain and Northern Ireland, Farnborough (GB)

( * ) Notice: Subject to any disclaimer, the term of this patent is extended or adjusted under 35 U.S.C. 154(b) by 0 days.

(21) Appl. No.: 09/520,614

(22) Filed: Mar. 7, 2000

Related U.S. Application Data

(62) Division of application No. 09/225,361, filed on Jan. 5, 1999, which is a division of application No. 08/676,203, filed on Jul. 10, 1996, now Pat. No. 5,891,358.

(30) Foreign Application Priority Data

Jan. 10, 1994 (GB) .................................................. 9400330
Jan. 6, 1995 (WO) .................................. PCT/GB95/00018

(51) Int. Cl.[7] ......................... C07C 43/205; C07C 43/21; C07C 43/225; C09K 19/12; C09K 19/30
(52) U.S. Cl. ....................... 568/642; 568/643; 568/645; 252/299.63; 252/299.65; 252/299.66
(58) Field of Search ............................... 568/642, 643, 568/645; 252/299.63, 299.65, 299.66

(56) References Cited

U.S. PATENT DOCUMENTS

| | | | |
|---|---|---|---|
| 4,728,458 | 3/1988 | Higuchi et al. | 252/299.65 |
| 4,818,432 * | 4/1989 | Miyazawa et al. | 252/299.66 |
| 5,011,623 | 4/1991 | Yoshinaga et al. | 252/299.5 |
| 5,098,602 | 3/1992 | Hirai et al. | 252/299.65 |
| 5,114,614 | 5/1992 | Emoto et al. | 252/299.65 |
| 5,116,527 | 5/1992 | Coates et al. | 252/299.61 |
| 5,312,564 | 5/1994 | Miyazawa et al. | 252/299.65 |
| 5,494,605 * | 2/1996 | Kurihara et al. | 252/299.66 |
| 5,543,078 | 8/1996 | Walba et al. | 252/299.65 |
| 5,637,256 | 6/1997 | Walba et al. | 252/299.66 |
| 5,658,493 | 8/1997 | Walba et al. | 252/299.01 |

FOREIGN PATENT DOCUMENTS

| | | |
|---|---|---|
| 188222 | 1/1986 | (EP) . |
| 243209 | 10/1987 | (EP) . |
| 256 303 | 2/1988 | (EP) . |
| 283326 | 9/1988 | (EP) . |
| 315701 | 5/1989 | (EP) . |
| 421012 | 4/1991 | (EP) . |
| 2244566 | 12/1991 | (GB) . |
| 2-183231 | 7/1990 | (JP) . |
| WO A 8911451 | 11/1989 | (WO) . |
| PCT/US92/ 03427 | 4/1992 | (WO) . |
| WO A 9220058 | 11/1992 | (WO) . |

OTHER PUBLICATIONS

Chemical Abstracts, vol. 106(26) Abstract No. 225118b JP 61/229844 Oct. 1986.

(List continued on next page.)

*Primary Examiner*—Gary Geist
*Assistant Examiner*—Leigh C. Maier
(74) *Attorney, Agent, or Firm*—Nixon & Vanderhye

(57) ABSTRACT

An electroclinic device having two spaced cell walls each bearing electrode structures and treated on at least one facing surface with an alignment layer, a layer of a smectic liquid crystal material enclosed between the cell walls, where the liquid crystal material contains one or more of the compounds described by formula I as defined in the specification.

2 Claims, 22 Drawing Sheets

OTHER PUBLICATIONS

Liquid Crystals vol. 14, No. 4 1993 pp. 1095–1105 Williams "Studies of the higher order smectic . . . ".

ACS Symposium Ser. 455 (mater. Nonlinear Opt) pp. 484–496 Chapter 32, Walba et al "ferroelectric liquid . . . ".

Liquid Crystals, vol. 14, No. 6, 1993 Schmitt et al.

J. Applied Physics, vol. 70, No. 7, 10/91 pp. 3425–3430 Liu et al "The measurement of second harmonic . . . ".

Liquid Crystals vol. 13, No. 3, 3/93 p 403–412 Schönfeld et al "collective and molecular dynamics . . . ".

* cited by examiner

*Scheme 1*

*Scheme 2*

Scheme 3

*Scheme 4*

*Scheme 5*

*Scheme 6*

*Scheme 7*

Scheme 8

*Scheme 9*

*Scheme 10*

Scheme 11

Scheme 12

*Scheme 13*

Scheme 14

*Scheme 15*

*Scheme 16*

*Scheme 17*

LIQUID CRYSTAL COMPOUNDS, MIXTURES AND DEVICES

This is a division of application Ser. No. 09/225,361, filed Jan. 5, 1999, which is a division of Ser. No. 08/676,203 filed Jul. 10, 1996 now U.S. Pat. No. 5,891,358 issued Apr. 6, 1999.

This invention relates to liquid crystal materials, in particular it relates to liquid crystal materials which exhibit one or more smectic phases.

Liquid crystals can exist in various phases. In essence there are three different classes of liquid crystalline material, each possessing a characteristic molecular arrangement. These classes are nematic, cholesteric and smectic. A wide range of smectic phases exists, for example smectic A and smectic C. Some liquid crystal materials possess a number of liquid crystal phases on varying the temperature, others have just one phase. For example, a liquid crystal material may show the following phases on being cooled from the isotropic phase:—isotropic—nematic—smectic A—smectic C—solid. If a material is described as being smectic A then it means that the material possesses a smectic A phase over a useful working temperature range.

Materials possessing a smectic A° ($S_A°$) phase may exhibit an electroclinic effect. The electroclinic effect was first described by S. Garoff and R. Meyer, Phys. Rev. Lett., 38, 848 (1977). An electroclinic device has also been described in UK patent application GB 2 244 566 A. This particular device helps to overcome the poor alignment problems of electroclinic (EC) devices using a surface alignment that gives a surface tilt within a small range of angles.

When a smectic A phase is composed of chiral molecules, it may exhibit an electroclinic effect, ie a direct coupling of molecular tilt to applied field. The origin of the electroclinic effect is a smectic A° phase composed of chiral polar molecules has been described by Garoff and Meyer as follows. The application of an electric field parallel to the smectic layers of such a smectic A° phase biases the free rotation of the transverse molecular dipoles and therefore produces a non-zero average of the transverse component of the molecular polarization. When such a dipole moment is present and coupled to the molecular chirality, a tilt of the long molecular axis (the director) is induced in a plane perpendicular to the dipole moment.

In thin samples for example 1–3 µm and with the smectic layers tilted or perpendicular with respect to the glass plates the electroclinic effect is detectable at low applied fields.

In an aligned smectic A sample a tilt of the director is directly related to a tilt of the optic axis. The electroclinic effect results in a linear electro-optic response. The electro-optic effect can manifest itself as a modulation of the effective birefringence of the device.

Electroclinic devices are useful, for example, in spatial light modulators having an output that varies linearly with applied voltage. A further advantage of EC devices is that they have high speed response times, much faster than nematic based devices, including twisted nematic based devices. Unlike ferroelectric devices the EC device is not bistable.

The electroclinic effect is sometimes referred to as the soft-mode effect see G. Andersson et al in Appl. Phys. Lett., 51, 9, (1987).

In general terms, regarding the electroclinic effect, it is advantageous if on applying a small voltage there results a large induced tilt.

An increase in induced tilt may result in an increase in contrast ratio or in phase modulation depth.

It is also advantageous if a large induced tilt can be obtained at as low a voltage as possible.

It is also advantageous if the relationship between molecular induced tilt and applied voltage is temperature independent. When an increase in applied voltage results in little or no change in induced tilt then the material being tested is generally referred to as exhibiting a saturation voltage effect.

Wand et al in Abstracts of the 4$^{th}$ International Conference of Ferroelectric Liquid Crystals Sep. 28–Oct. 1, 1993 in Tokyo, Japan: Paper P90, pages 257–58 and see references therein, report on novel electroclinic materials. They suggest that the reason for the materials they report exhibiting a large and temperature insensitive electroclinic tilt is due to the absence of a C° phase underlying the A° phase and that it is usual for materials possessing a C° phase below the A° phase to exhibit a relatively steep temperature dependence of induced tilt.

By $S_A°$ meant a $S_A$ phase which contains some proportion of chiral molecules.

According to this invention an electroclinic device comprises two spaced cell walls each bearing electrode structures and treated on at least one facing surface with an alignment layer, a layer of a smectic liquid crystal material enclosed between the cell walls, characterised in that the liquid crystal material contains one or more of the compounds described by formula I:

Formula 1

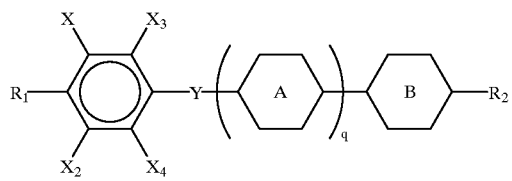

wherein

X may be CN, $NO_2$, $CF_3$, $CF_2H$, $CFH_2$, halogen, hydrogen, alkyl or alkoxy;

$X_2$ may be CN, $NO_2$, $CF_3$, $CF_2H$, $CFH_2$, halogen, hydrogen, alkyl or alkoxy;

$X_3$ may be CN, $NO_2$, $CF_3$, $CF_2H$, $CFH_2$, halogen, alkyl, alkoxy or hydrogen;

$X_4$ may be CN, $NO_2$, $CF_3$, $CF_2H$, $CFH_2$, halogen, alkyl, alkoxy or hydrogen;

provided that at least one of X or $X_2$ is $CF_3$, $CF_2H$, $CFH_2$, CN, $NO_2$ or halogen;

A and B are independently phenyl, mono-fluorinated phenyl, di-fluorinated phenyl or cyclohexyl;

Y may be single bond, COO, OOC, C=C;

q may be 0 or 1;

$R_1$ may be an end group of the following Formula II:

Formula II

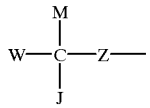

wherein

Z may be a single bond, O, $CO_2$, $(CH_2)_n$ or $(CH_2)_nO$ where n may be 1 or 2;

J and M may be independently H, $C_{1-4}$ alkyl;

W may be $C_1$–$C_{12}$ straight or branched alkyl chain;

$R_2$ may contain 1–14 carbon atoms wherein one or more non-adjacent $CH_2$ groups may be replaced by $CO_2$ or O.

Preferably:

W is $C_1$–$C_8$ straight chain alkyl, Z is O or $CH_2O$, M or J are independently chosen from H or Me or Et;

$R_2$ contains 5–12 carbon atoms wherein one of the $CH_2$ groups may be replaced by $CO_2$ or O;

q=1;

A and B are both phenyl;

$X_3$ and $X_4$ are both H;

Y is $CO_2$ or a single bond;

X or $X_2$ is $NO_2$ or $CF_3$ or halogen or CN.

According to a second aspect of this invention compounds of the following formula are provided:

Formula 1

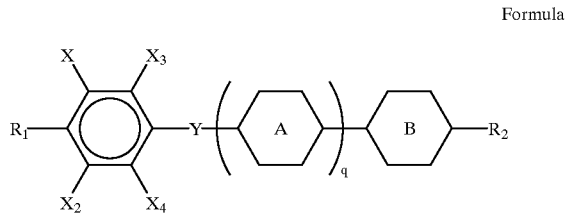

wherein

X may be $CF_3$, $CF_2H$, $CFH_2$, hydrogen, $NO_2$, alkyl or alkoxy;

$X_2$ may be $CF_3$, $CF_2H$, $CFH_2$, hydrogen, $NO_2$, alkyl or alkoxy;

$X_3$ may be $CF_3$, $CF_2H$, $CFH_2$, alkyl, $NO_2$, alkoxy or hydrogen;

$X_4$ may be $CF_3$, $CF_2H$, $CFH_2$, alkyl, $NO_2$, alkoxy or hydrogen;

provided that at least one of X or $X_2$ is $CF_3$, $CF_2H$, $CFH_2$, $NO_2$;

A and B are independently phenyl, mono-fluorinated phenyl, di-fluorinated phenyl or cyclohexyl;

Y may be single bond, COO, OOC, C=C;

q may be 0 or 1;

$R_1$ may be an end group of the following Formula II:

Formula II

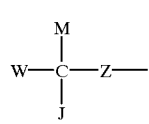

wherein

Z may be a single bond, O, $CO_2$, $(CH_2)_n$ or $(CH_2)_nO$ where n may be 1 or 2;

J and M may be independently H, $C_{1-4}$ alkyl;

W may be $C_1$–$C_{12}$ straight or branched alkyl chain;

$R_2$ may contain 1–14 carbon atoms wherein one or more non-adjacent $CH_2$ groups may be replaced by $CO_2$ or O.

Preferably:

W is $C_1$–$C_8$ straight chain alkyl, Z is O or $CH_2O$, M or J are independently chosen from H or Me or Et;

$R_2$ contains 5–12 carbon atoms wherein one of the $CH_2$ groups may be replaced by $CO_2$ or O;

q=1;

A and B are both phenyl;

$X_3$ and $X_4$ are both H;

Y is $CO_2$ or a single bond;

X or $X_2$ is $CF_3$.

It is believed that these compounds may be characterised by there being intramolecular steric hindrance between the 'X' group(s) and the adjacent terminal groups of formula I. This in turn may induce a large incipient spontaneous polarisation (Ps) in the molecule which in turn gives rise to a large induced tilt when a field is applied. A large induced tilt usually gives rise to an improved contrast ratio.

The invention will now be described, by way of example only, with reference to the following diagrams.

Figure 1:
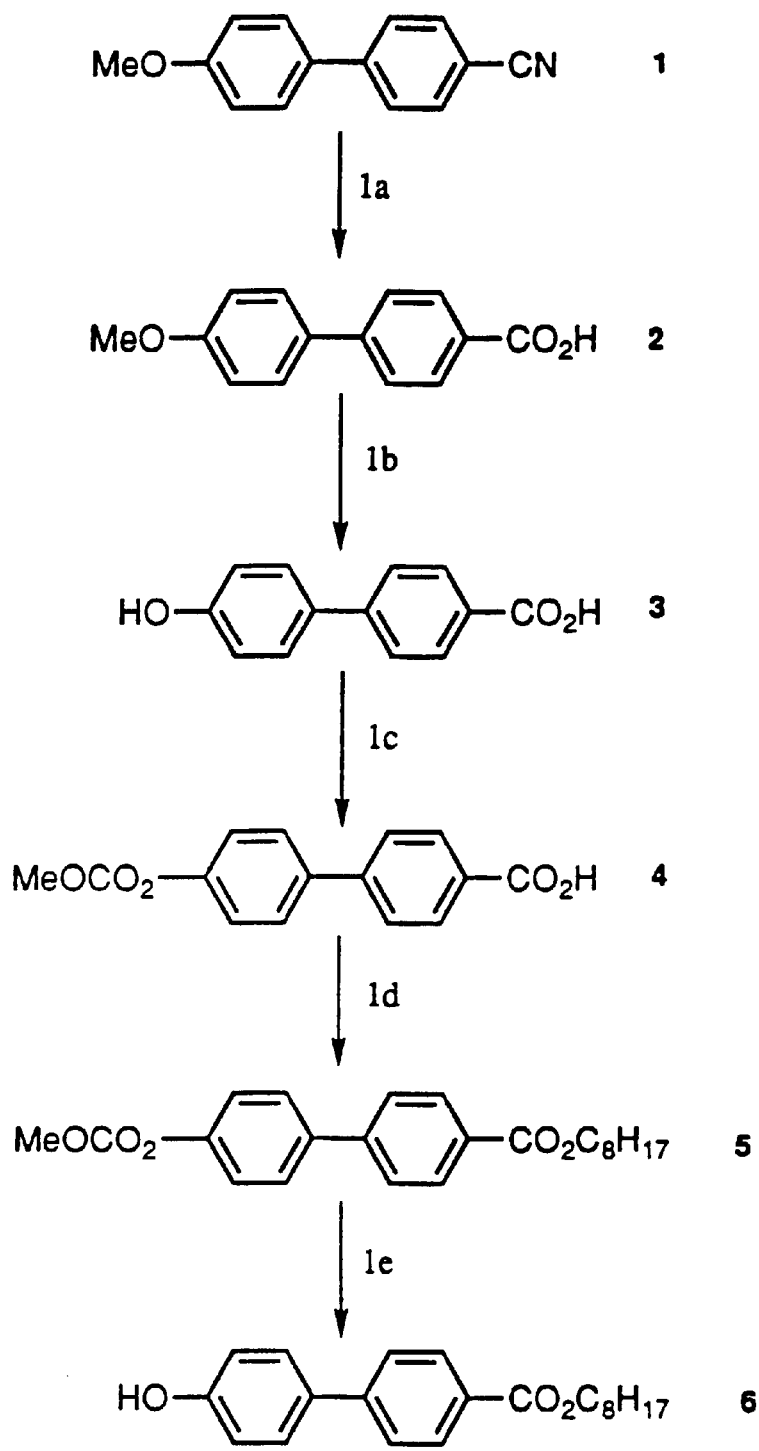
FIGS. 1–18 show synthetic schemes for the preparation of compounds.

Reagents used in the synthetic route of FIG. 1 are shown in the corresponding Scheme 1.

1*a*: $H_2SO_4$, $H_2O$, HOAc

1*b*: HBr, HOAc

1*c*: (i) MeOCOCl, NaOH, $H_2O$; (ii) aq. HCl

1*d*: octan-1-ol, DEAD, $PPh_3$, THF

1*e*: aq $NH_3$, EtOH

Figure 2:
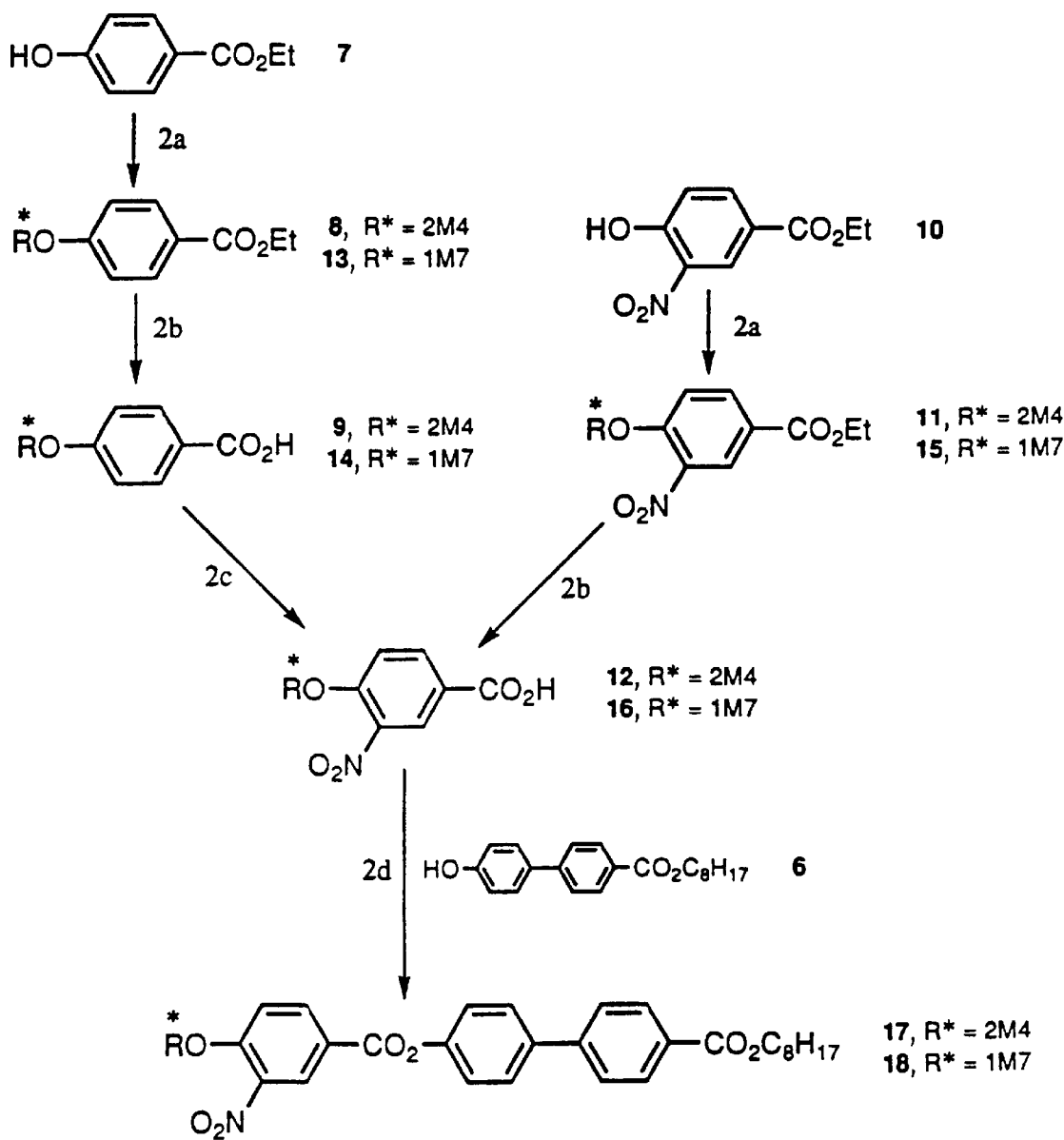

Reagents used in the synthetic route of FIG. 2 are shown in the corresponding Scheme 2.

2*a*: R*OH, DEAD, $PPh_3$, THF

2*b*: (i) NaOH, $H_2O$, EtOH; (ii) aq HCl

2*c*: $HNO_3$, $H_2SO_4$, glacial acetic acid

2*d*: DCC, DMAP, $CH_2Cl_2$

Figure 3:
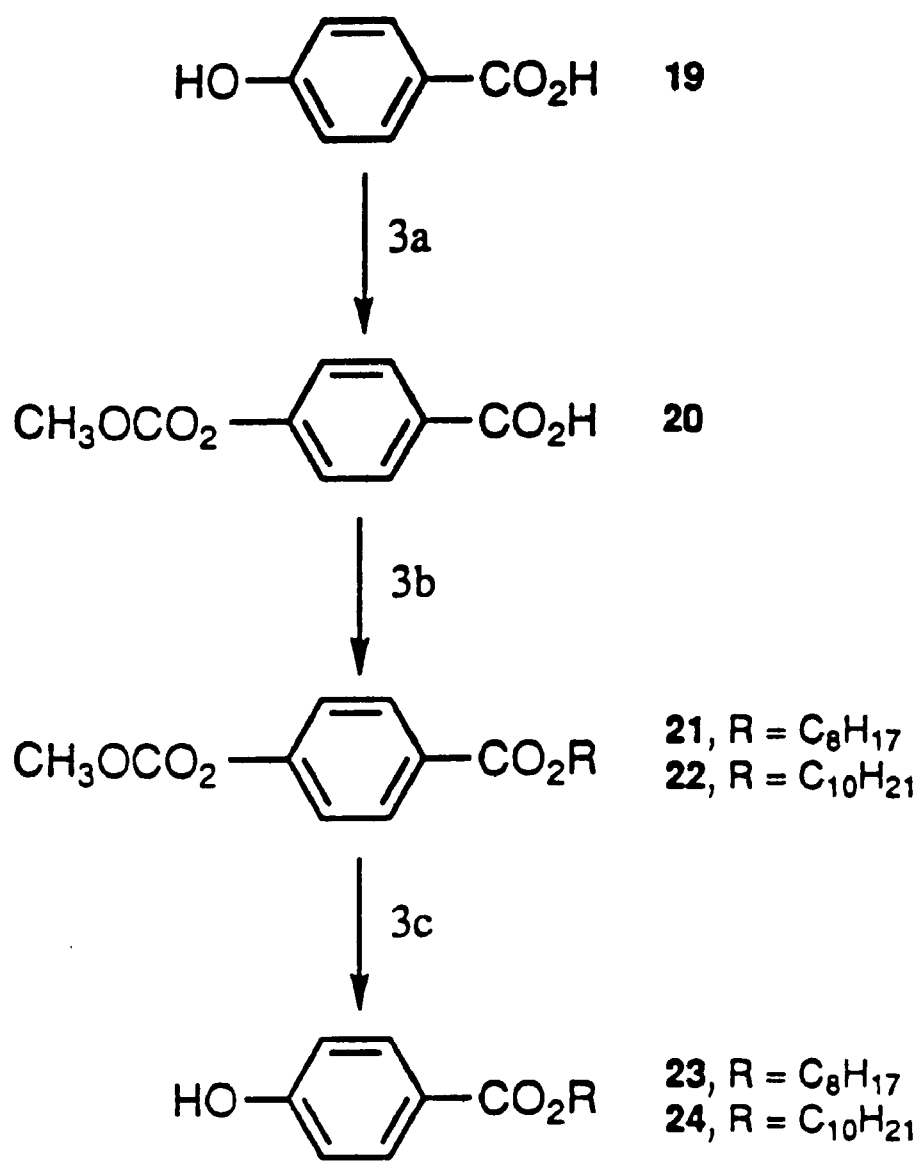

Reagents used in the synthetic route of FIG. 3 are shown in the corresponding Scheme 3.

3*a*: (i) MeOCOCl, NaOH, $H_2O$; (ii) aq. HCl

3*b*: octan-1-ol or decan-1-ol, DEAD, $PPh_3$, THF

3*c*: aq. $NH_3$, EtOH

Figure 4:
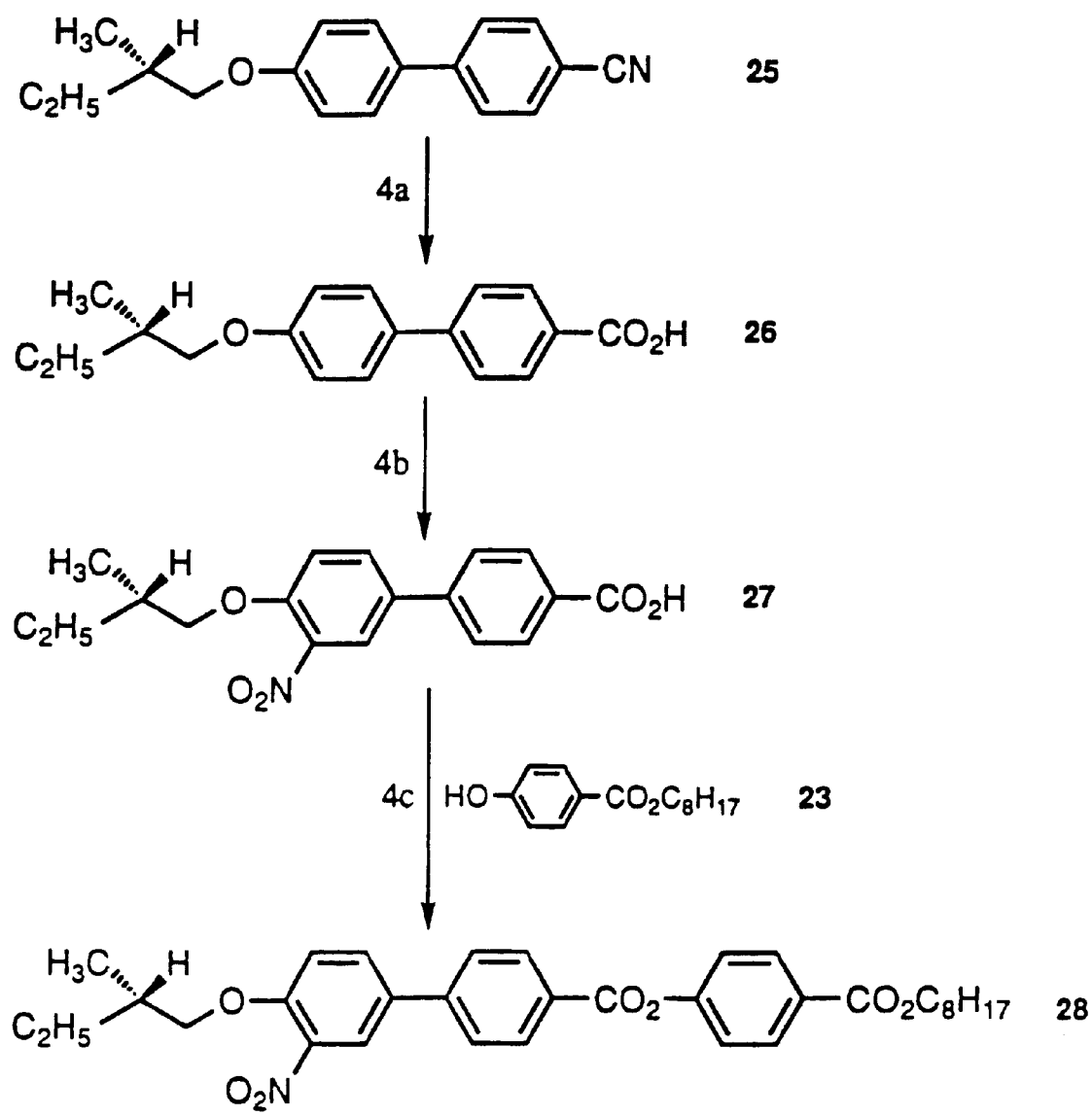

Reagents used in the synthetic route of FIG. 4 are shown in the corresponding Scheme 4.

4*a*: $H_2SO_4$, $H_2O$, glacial acetic acid

4*b*: $H_2SO_4$, $HNO_3$, glacial acetic acid

4*c*: DCC, DMAP, $CH_2Cl_2$

Figure 5:
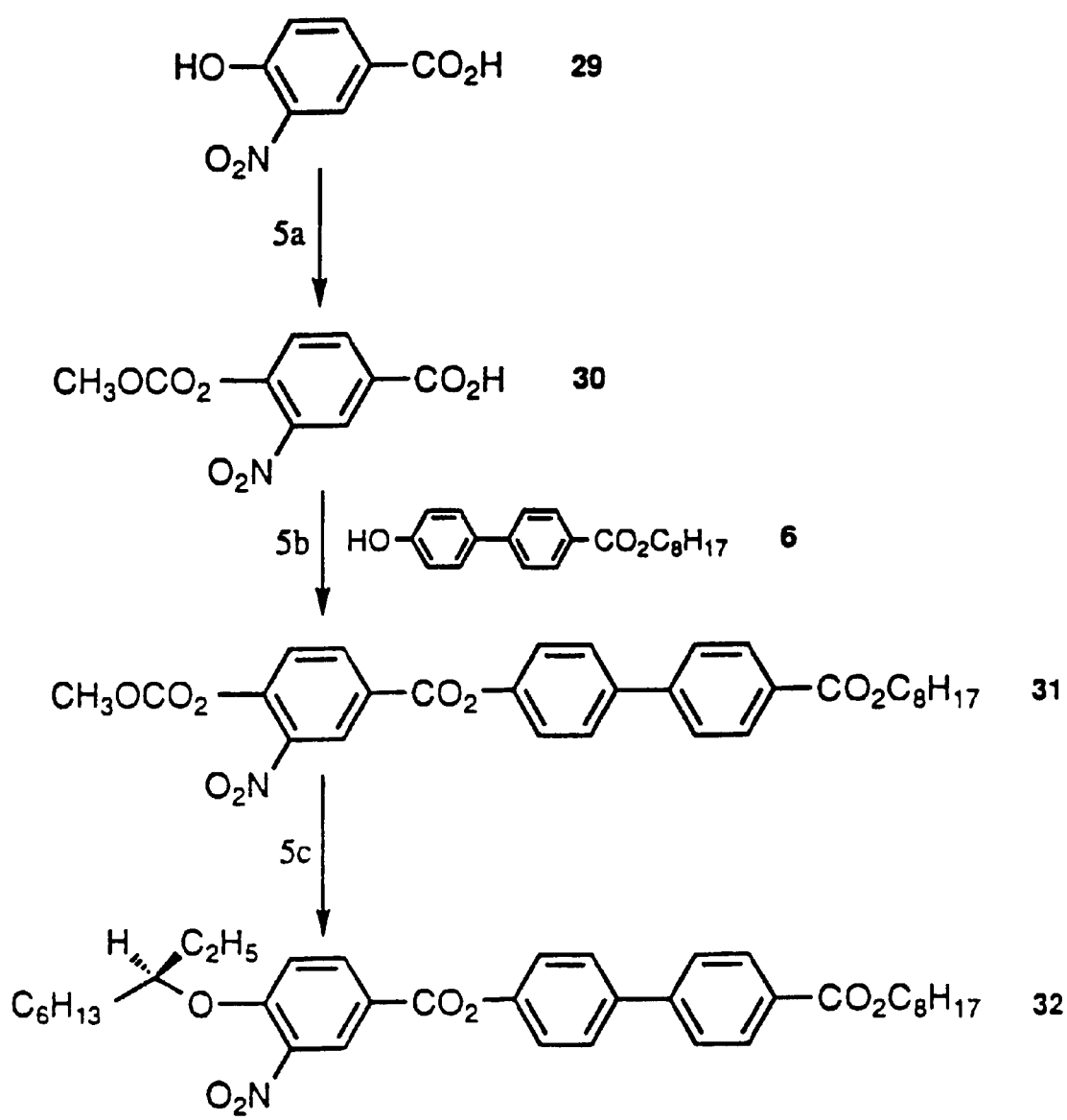

Reagents used in the synthetic route of FIG. 5 are shown in the corresponding Scheme 5.

5*a*: (i) MeOCOCl, NaOH, $H_2O$; (ii) aq. HCl

5*b*: DEAD, $PPh_3$, THF

5*c*: (S)-nonan-3-ol, DEAD/$PPh_3$, THF

Figure 6:
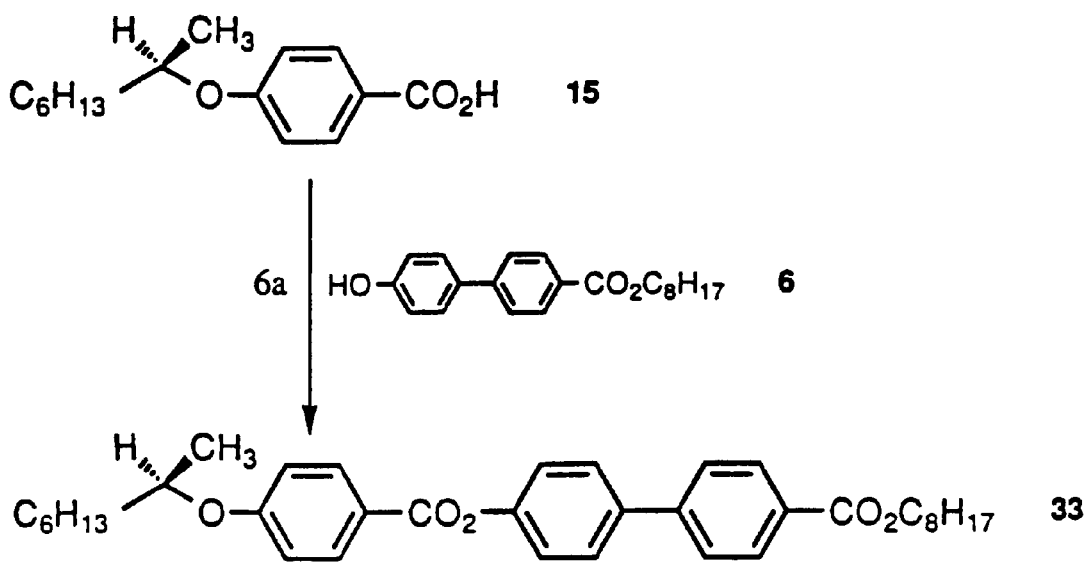

Reagents used in the synthetic route of FIG. 6 are shown in the corresponding Scheme 6.

6*a*: DCC, DMAP, $CH_2Cl_2$

Figure 7:
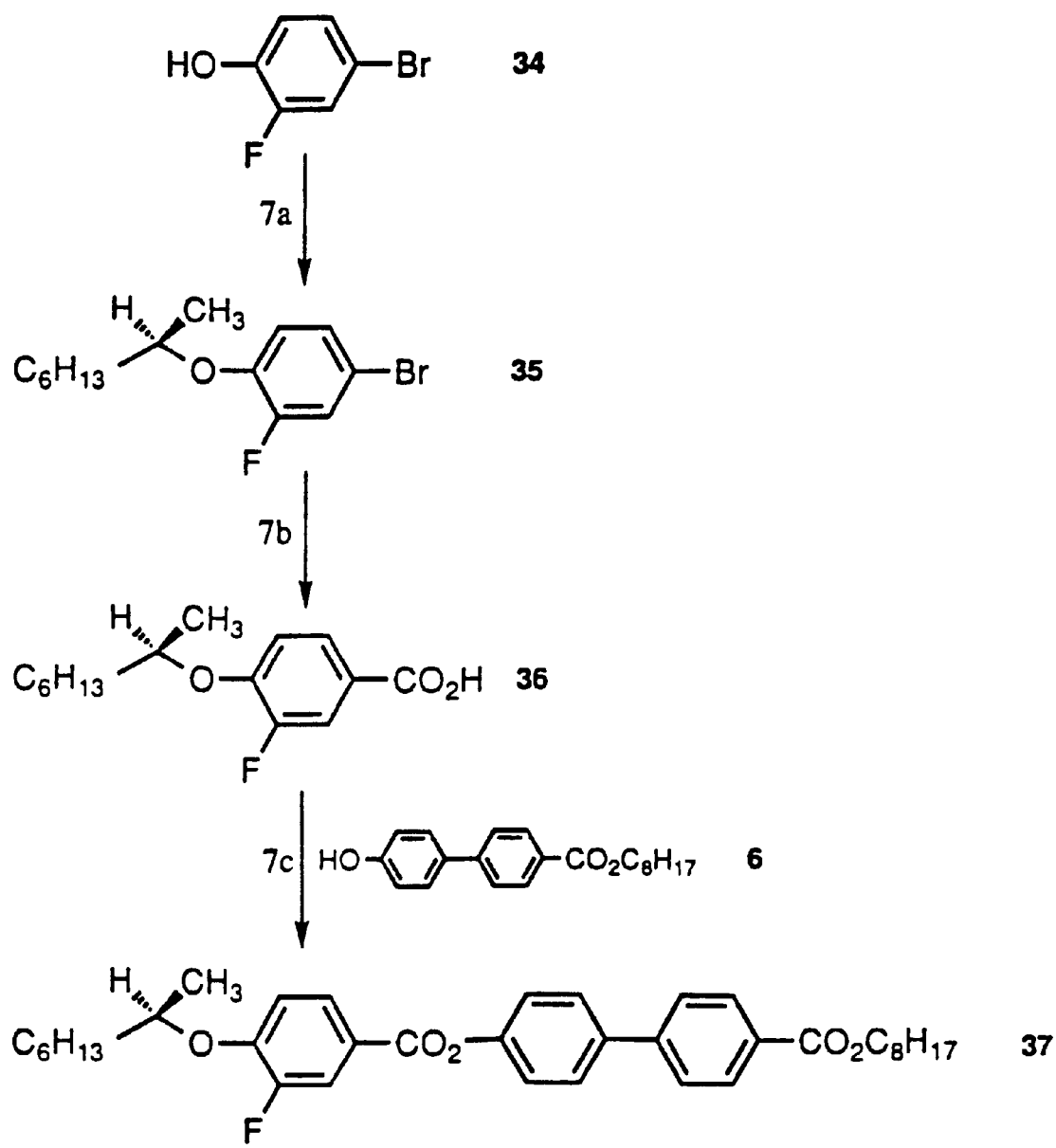

Reagents used in the synthetic route of FIG. 7 are shown in the corresponding Scheme 7.

7*a*: (S)-octan-2-ol, DEAD, $PPh_3$, THF

7*b*: (i) n-butyllithium, THF, (ii) $CO_2$ (solid), THF; (iii) aq. HCl

7c: DMAP, CH$_2$Cl$_2$

Figure 8:
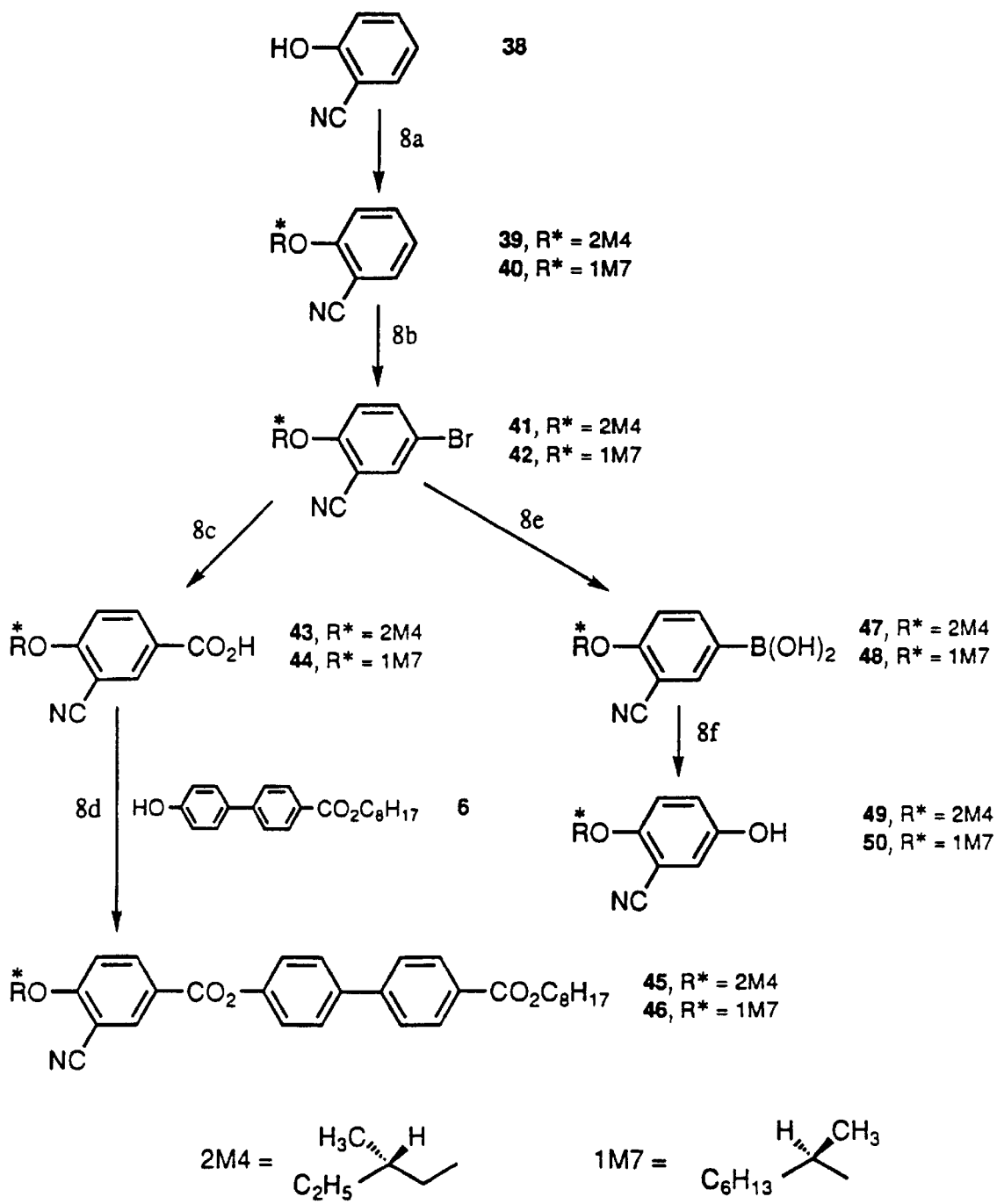

Reagents used in the synthetic route of FIG. 8 are shown in the corresponding Scheme 8.

Figure 9:
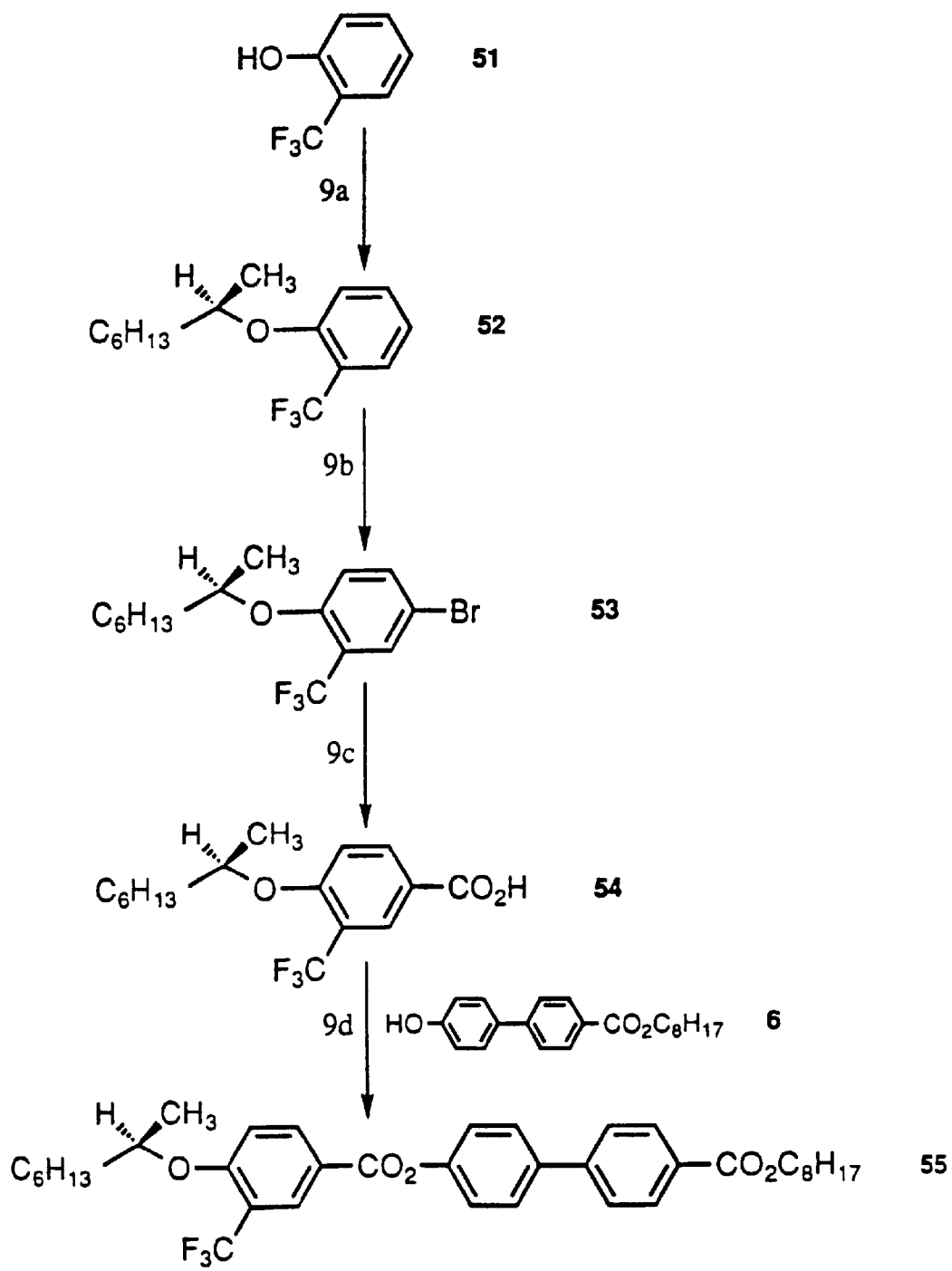

8a: R*OH, DEAD, PPh$_3$, THF
8b: Br$_2$, CHCl$_3$
8c: n-butyllithium, THF, (ii) CO$_2$ (solid), THF; (iii) aq. HCl
8d: DCC, DMAP, CH$_2$Cl$_2$
8e: (i) n-butyllithium, THF, (ii) trimethyl borate, THF; (iii) aq. HCl
8f: H$_2$O$_2$, THF Reagents used in the synthetic route of FIG. 9 are shown in the corresponding Scheme 9.

Figure 10:
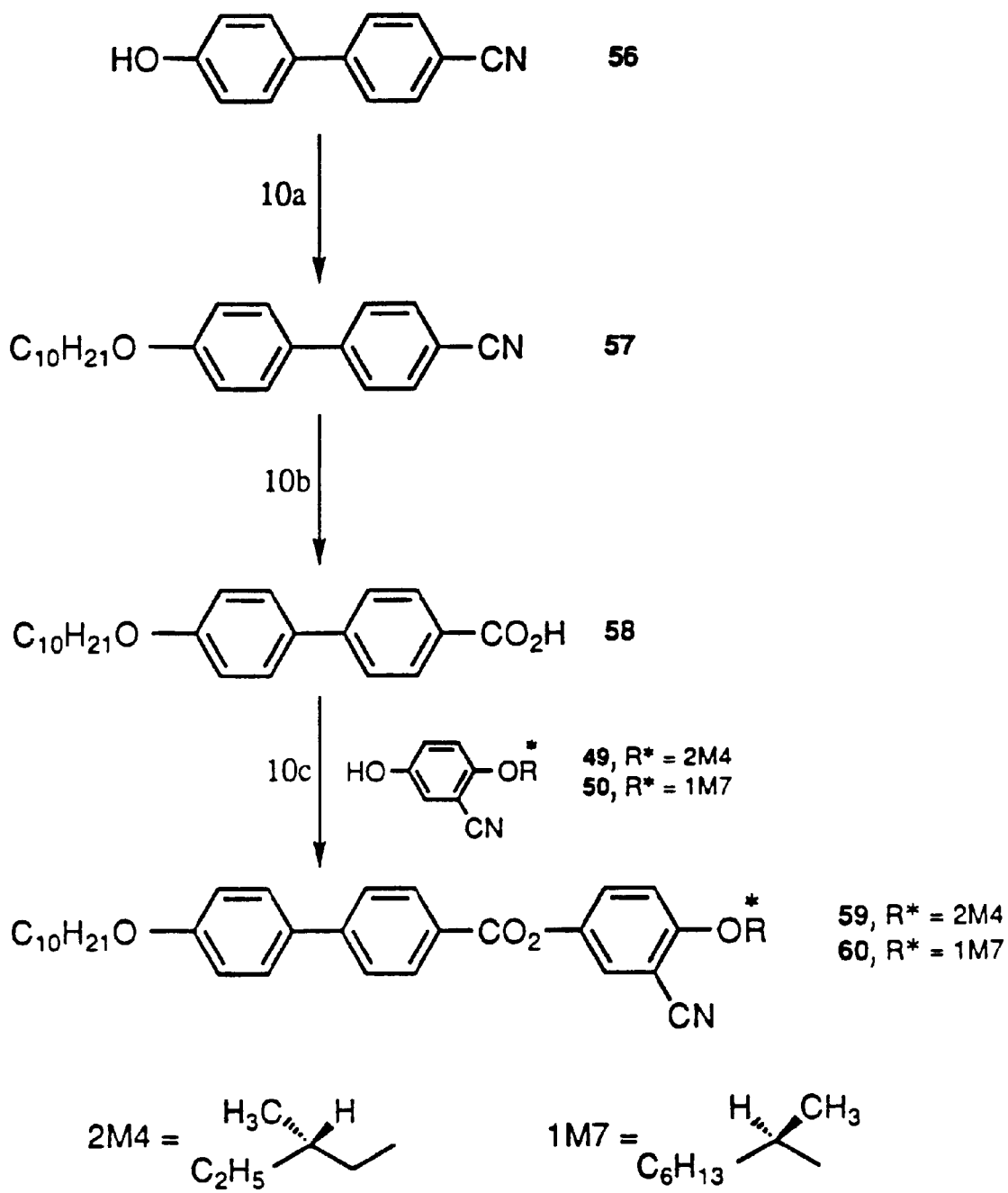

9a: (S)-octan-2-ol, DEAD, PPh$_3$, THF
9b: Br$_2$, CHCl$_3$
9c: (i) n-butyllithium, THF, (ii) CO$_2$ (solid), THF; (iii) aq. HCl
9d: DCC, DMAP, CH$_2$Cl$_2$ Reagents used in the synthetic route of FIG. 10 are shown in the corresponding Scheme 10.

Figure 11:
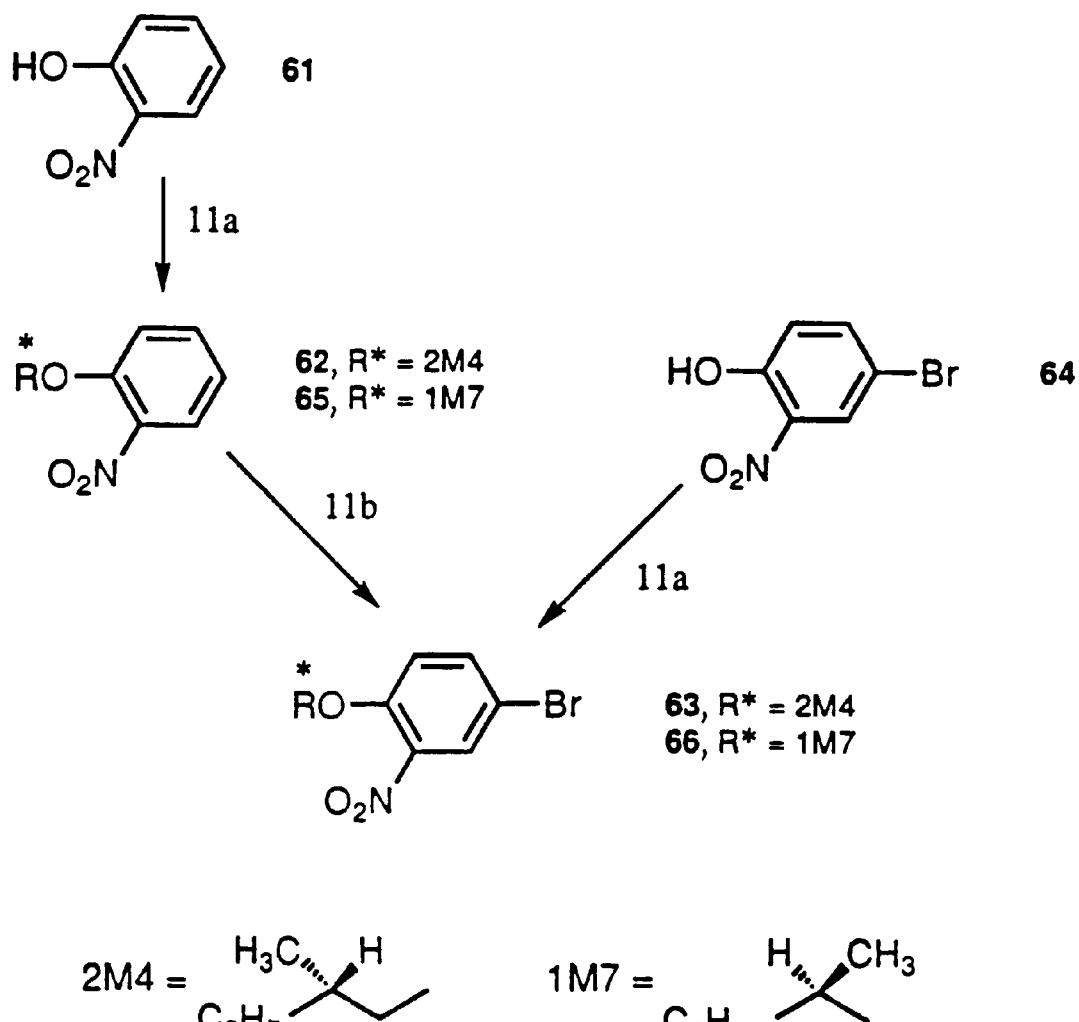

10a: 1-bromodecane, K$_2$CO$_3$, KI, butanone
10b: H$_2$SO$_4$, H$_2$O, glacial acetic acid
10c: DCC, DMAP, CH$_2$Cl$_2$ Reagents used in the synthetic route of FIG. 11 are shown in the corresponding Scheme 11.

Figure 12:
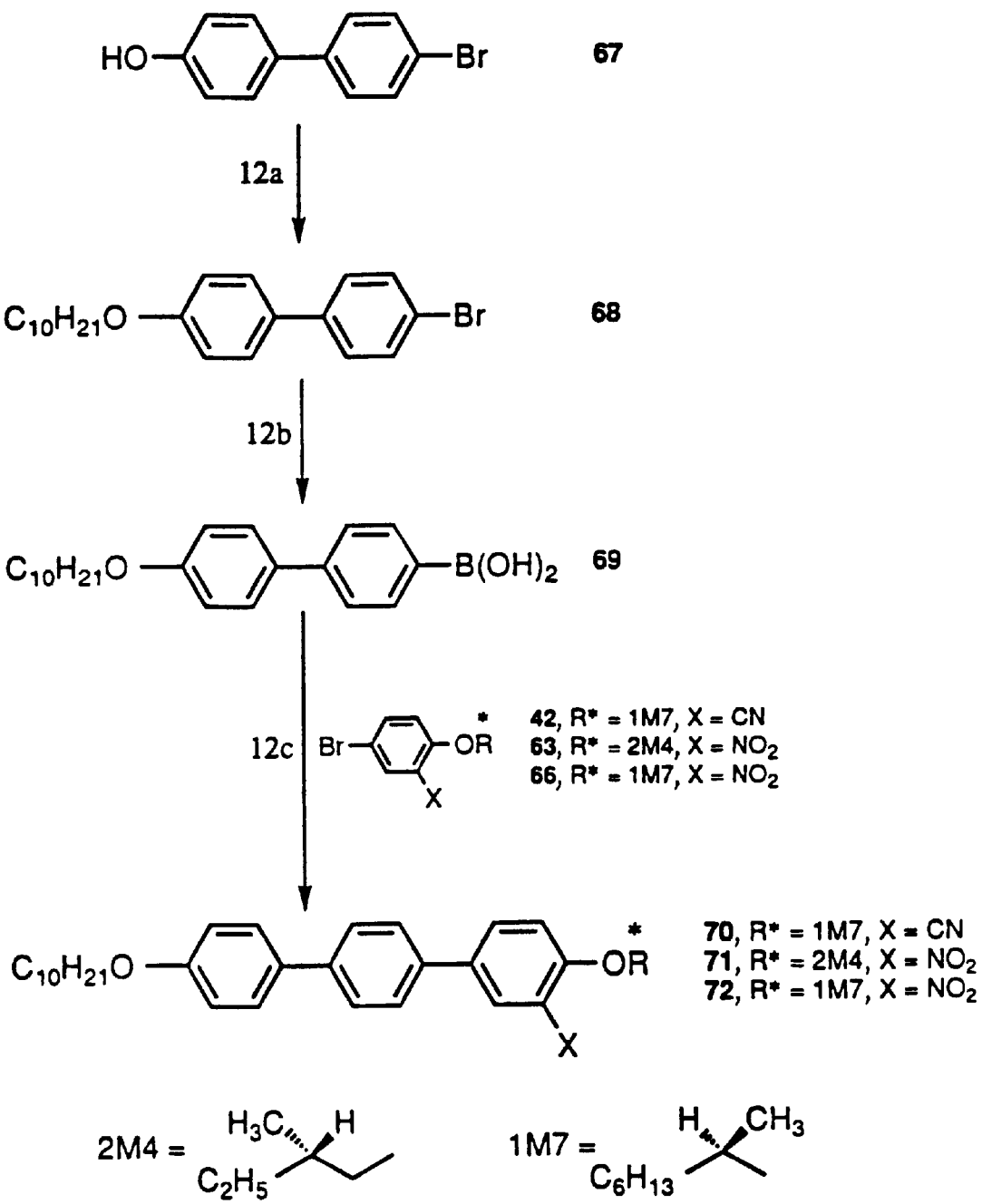

11a: (S)-2-methylbutan-1-ol or (S)-octan-2-ol, DEAD/PPh$_3$, THF
11b: Br$_2$, CHCl$_3$ Reagents used in the synthetic route of FIG. 12 are shown in the corresponding Scheme 12.

Figure 13:
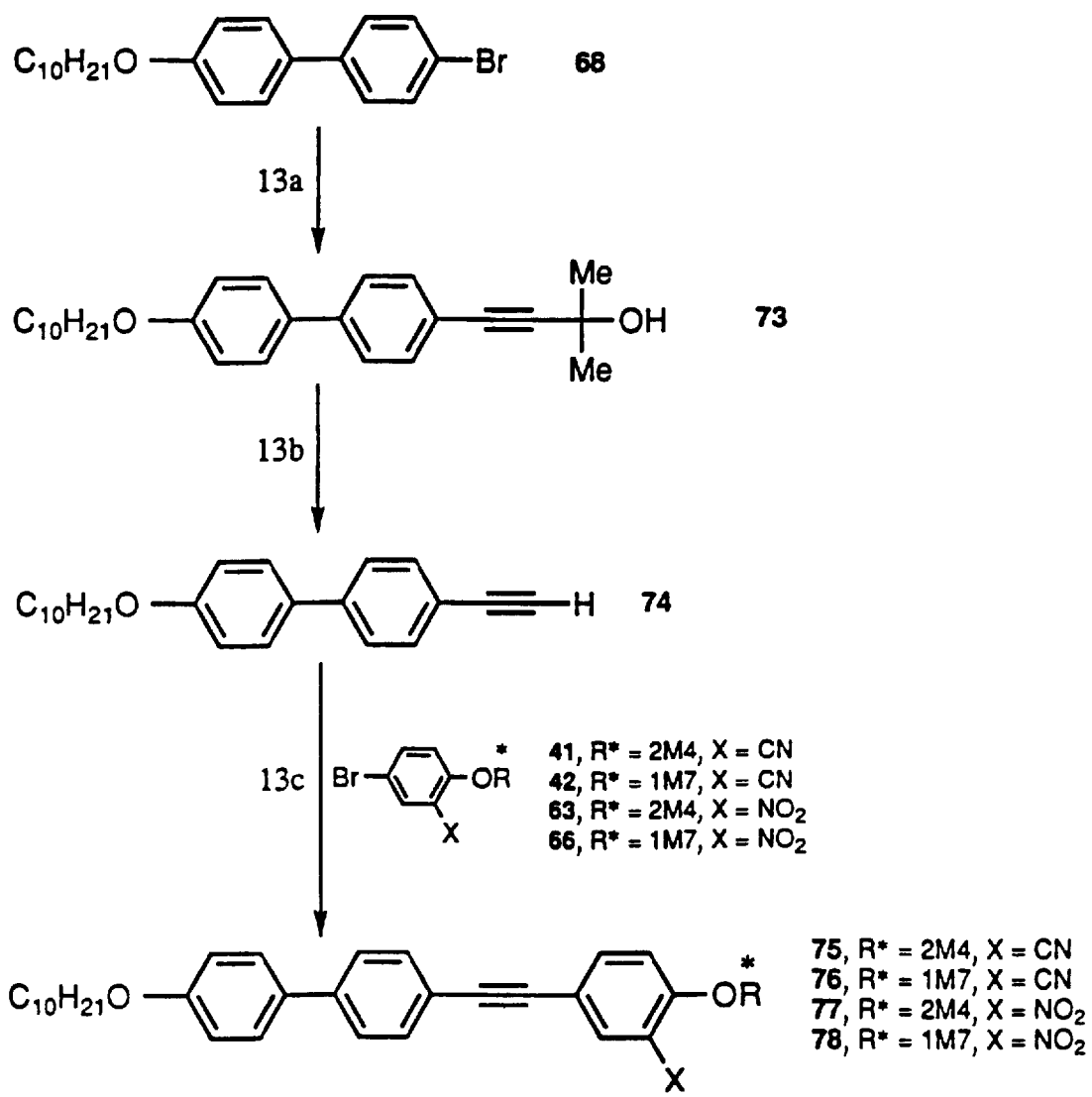
Figure 13:
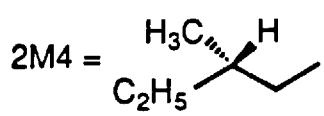
Figure 13:
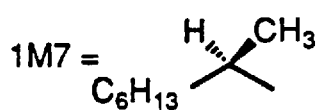

12a: (S)-octan-2-ol, DEAD, PPh$_3$, THF
12b: (i) n-butyllithium, THF or Mg, THF; (ii) CO$_2$ (solid), THF; (iii) aq. HCl
12c: Pd(PPh$_3$)$_4$, 2M NaCO$_3$, 1,2-dimethoxyethane Reagents used in the synthetic route of FIG. 13 are shown in the corresponding Scheme 13.

Figure 14:
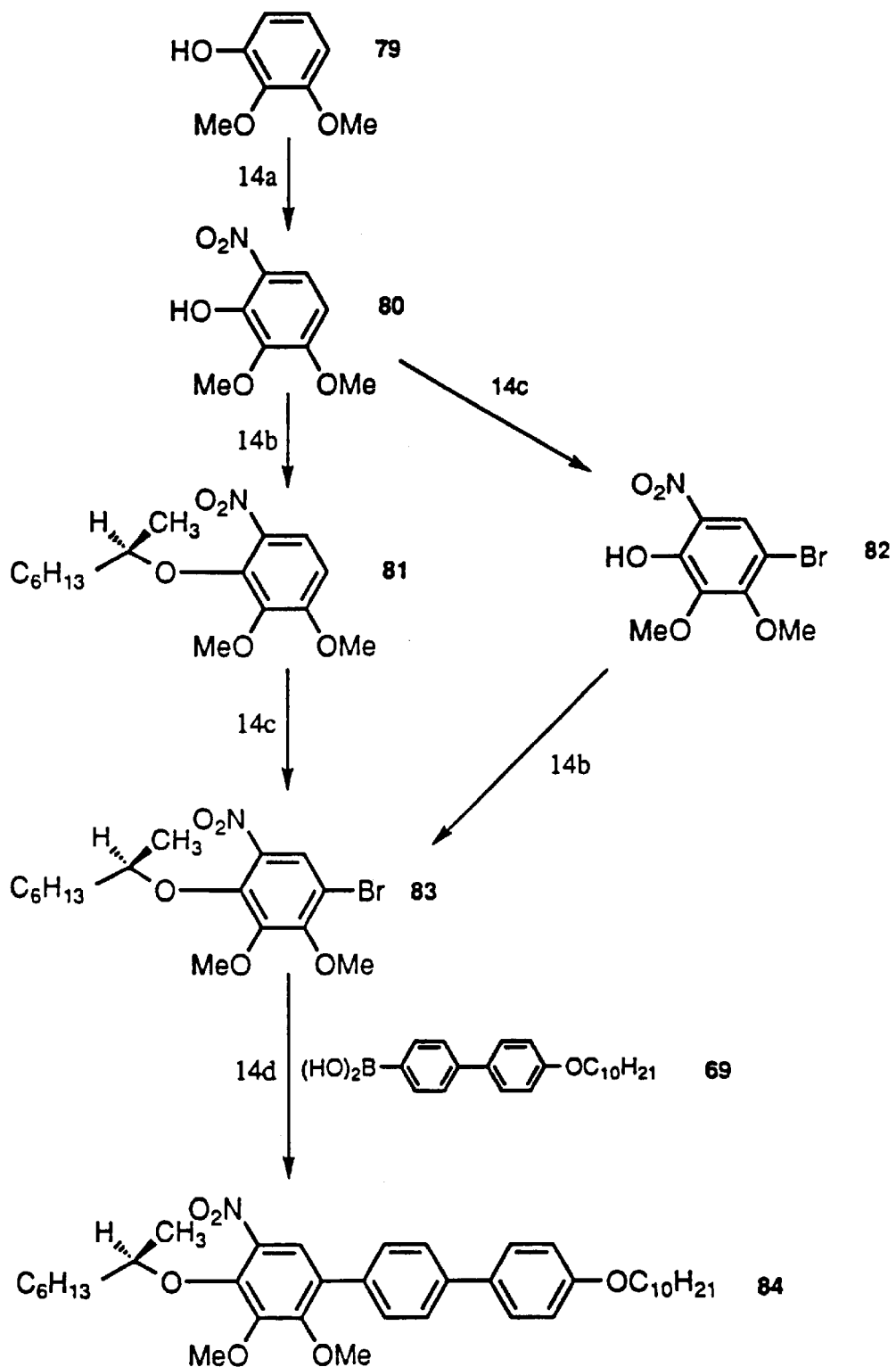

13a: 2-methyl-but-3-yn-2-ol, Pd(PPh$_3$)$_4$, CuI, diisopropylamine
13b: NaOH, toluene
13c: Pd(PPh$_3$)$_4$, CuI, triethylamine Reagents used in the synthetic route of FIG. 14 are shown in the corresponding Scheme 14.

Figure 15:
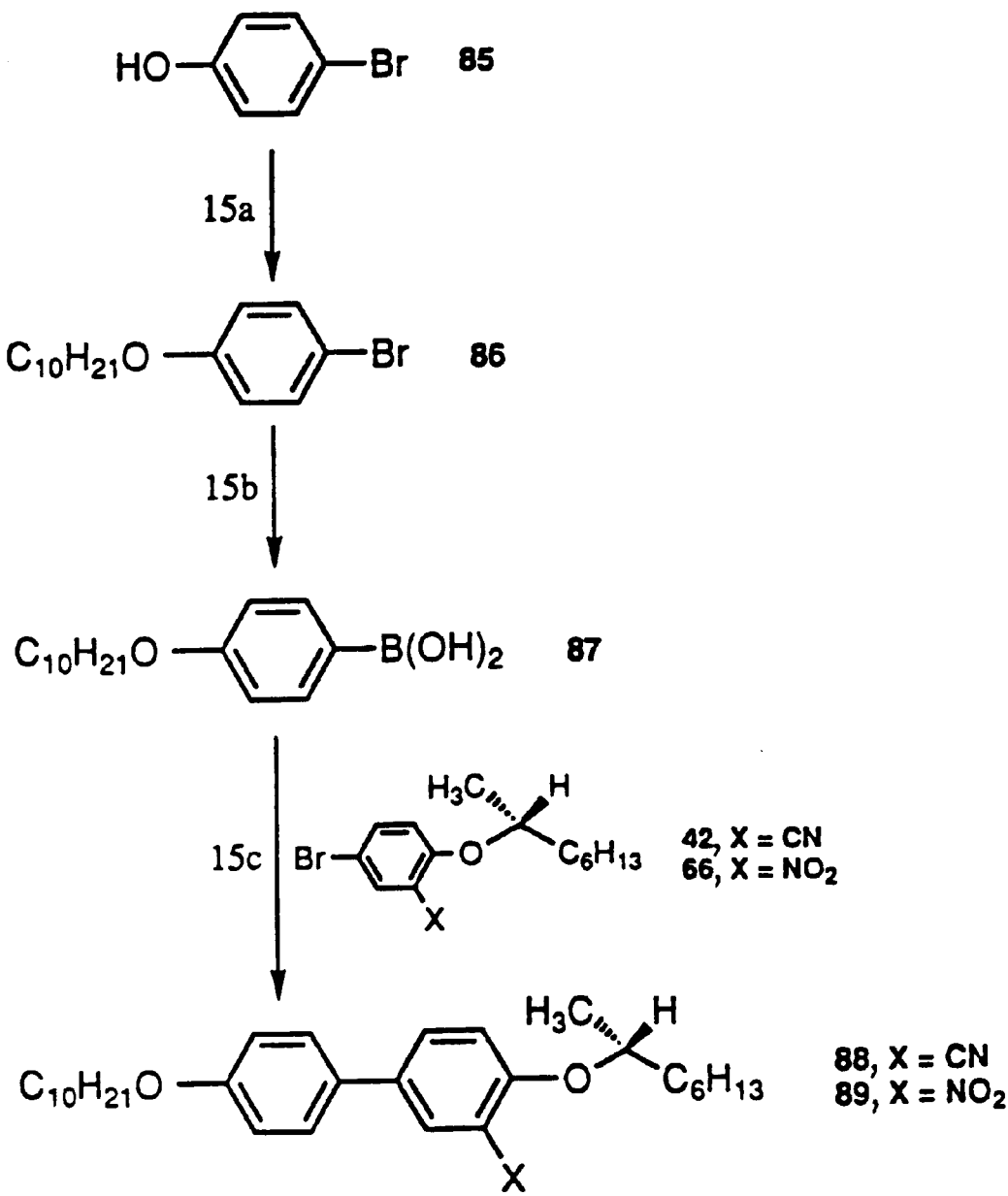

14a: H$_2$O, HNO$_3$, glacial acetic acid
14b: (S)-octan-2-ol, DEAD, PPh$_3$, THF
14c: Br$_2$, CHCl$_3$
14d: Pd(PPh$_3$)$_4$, 2M NaCO$_3$, 1,2-dimethoxyethane Reagents used in the synthetic route of FIG. 15 are shown in the corresponding Scheme 15.

Figure 16:
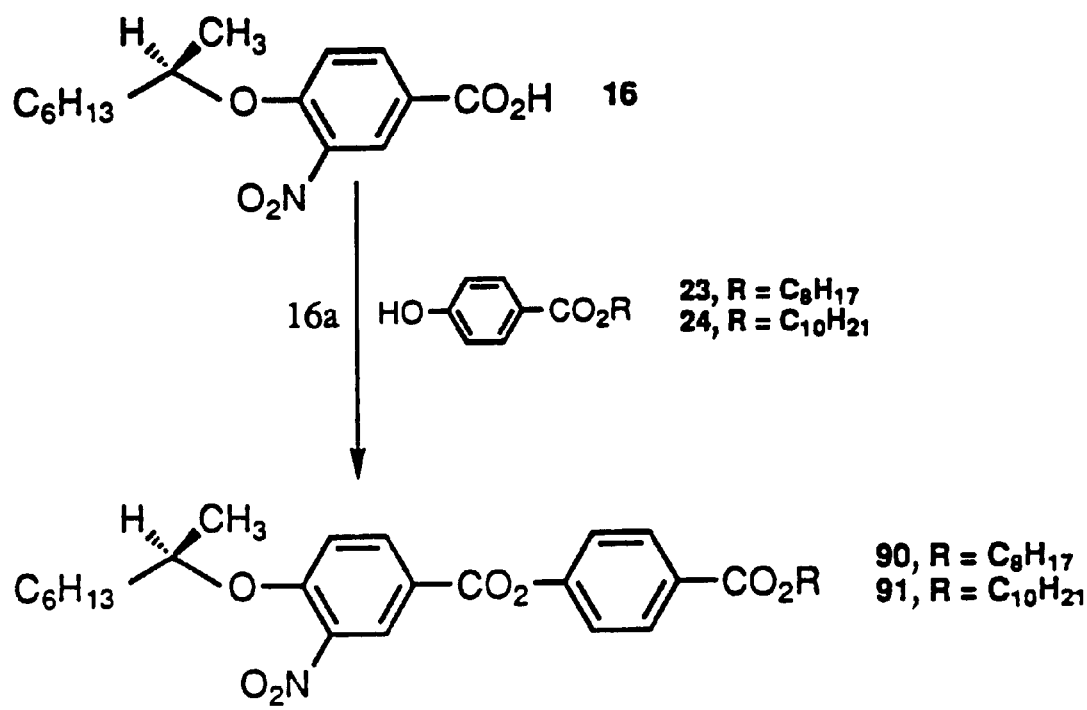

15a: 1-bromooctane, K$_2$CO$_3$, KI, butanone
15b: (i) n-butyllithium, THF, (ii) trimethyl borate, THF; (iii) aq. HCl
15c: Pd(PPh$_3$)$_4$, 2M NaCO$_3$, 1,2-dimethoxyethane Reagents used in the synthetic route of FIG. 16 are shown in the corresponding Scheme 16.

16a: DCC, DMAP, CH$_2$Cl$_2$

Figure 17:
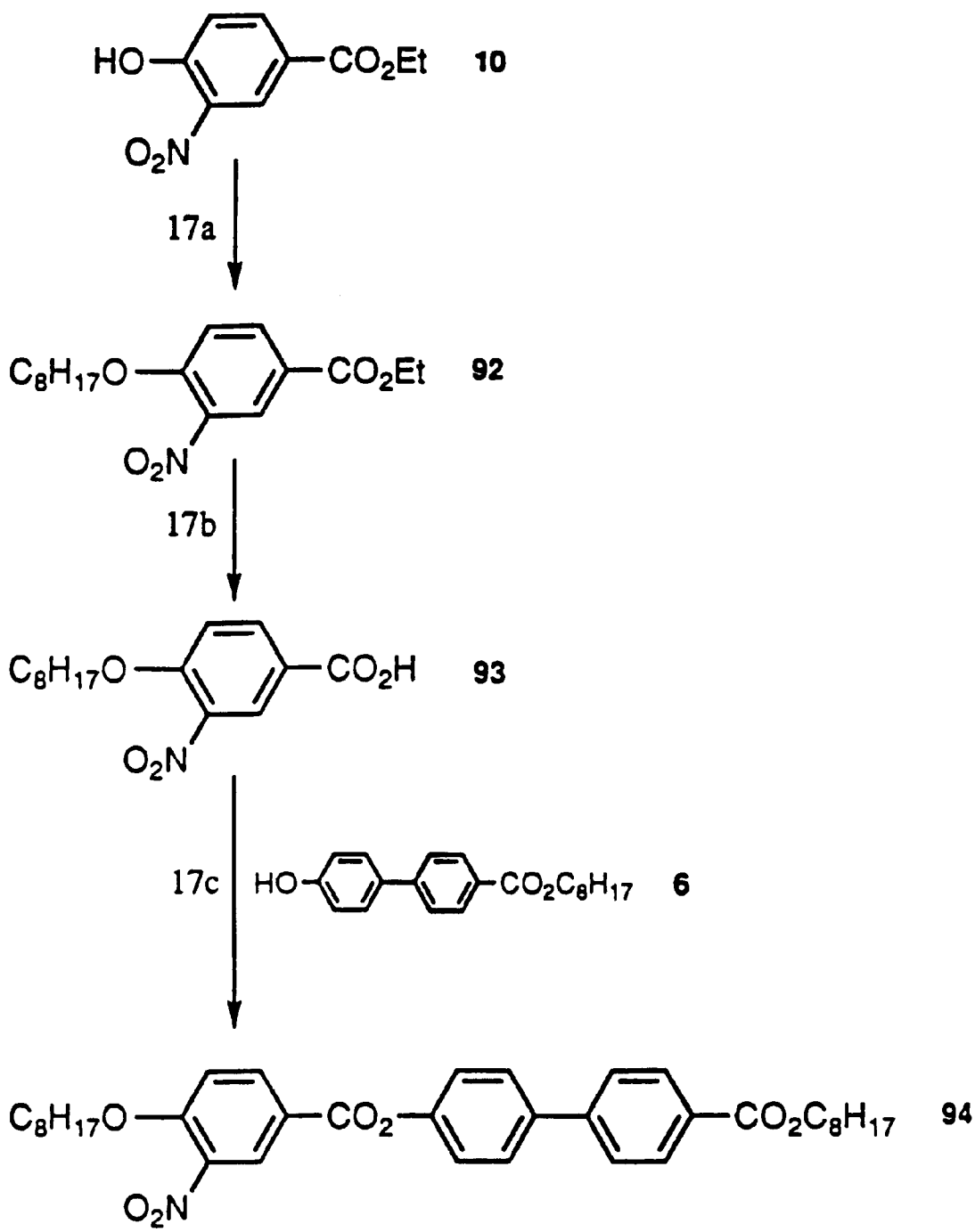

Reagents used in the synthetic route of FIG. 17 are shown in the corresponding Scheme 17.

Figure 18:
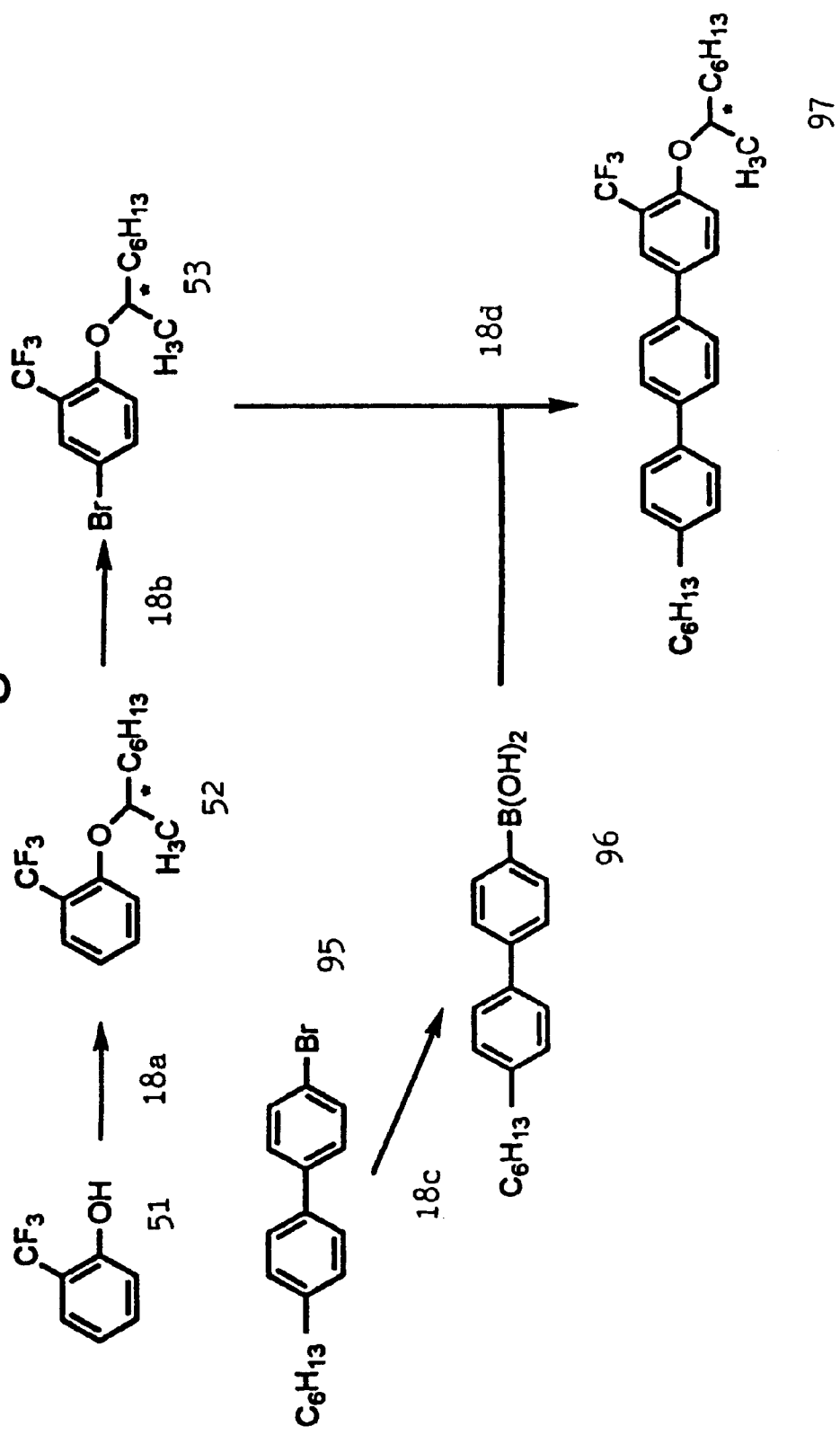

17a: 1-bromooctane, K$_2$CO$_3$, KI, butanone
17b: (i) NaOH, H$_2$O, EtOH (ii) aq HCl
17c: DCC, DMAP, CH$_2$Cl$_2$ Reagents used in the synthetic route of FIG. 18 are shown in the corresponding Scheme 18.

18a: octan-2-ol, DEAD, TPP, THF;
18b: Br$_2$, CHCl$_3$;
18c: (i) Mg, THF; (ii) (MeO)$_3$B, THF; (iii) 10% HCl;
18d: Pd(PPh$_3$)$_4$, DME, Na$_2$CO$_3$, water.

where:

| |
|---|
| DEAD = diethylazodicarboxylate. |
| THF = tetrahydrofuran. |
| DCC = dicyclohexylcarbodiimide. |
| DMAP = N,N-dimethylaminopyridine. |
| TPP = triphenylphosphine. |
| DME = 1,2-dimethoxyethane. |

Experimental details relating to the steps in synthetic schemes described by FIGS. 1–18 are as follows.

4'-Methoxy -4-biphenylcarboxylic acid (2)

A stirred mixture of 4-cyano-4'-methoxybiphenyl (1) (30.00 g, 0.144 mol), concentrated sulphuric add (60 ml), and water (60 ml) in glacial acetic add (600 ml was heated under reflux for 6 h. The mixture was left to cool to room temperature during which time white crystals formed and then poured into an ice/water mixture (21). The resultant white precipitate was filtered off and washed with water until acid-free. The white solid was recrystallized from glacial acetic acid to afford colourless crystals which were dried over potassium hydroxide in vacuo.

TLC analysis (5% methanol/dichloromethane) revealed two spots.

Yield 27.50 g (84%); mesomorphic behaviour (° C) K254.6 N 295 I (lit. K 258 N 300 I).

| | |
|---|---|
| $^1$H NMR (CDCl$_3$ + DMSO) δ | 3.85(3H, s), 7.00(2H, d), 7.60(2H, d), 7.65(2H, d), 8.10(2H, d), no obvious OH absorption; |
| IR (KBr) v$_{max}$/cm$^{-1}$ | 3300–2300, 1680, 1255, 930; |
| MS (m/z) | 228[M$^+$], 213, 185, 139. |

4'-Hydroxy-4-biphenylcarboxylic acid (3)

A stirred mixture of compound 2 (27.00 g, 0.118 mol) and hydrobromic acid (48% w/v, 350 ml) in glacial acetic acid (600 ml) was heated under reflux for 6 h. The cooled solution was poured into an ice/water mixture (11) and the resulting white precipitate was filtered off and washed with water until acid-free. Recrystallization, from glacial acetic acid afforded white crystals which were dried over potassium hydroxide in vacuo.

Yield 20.00 g (79%); mp>300° C.

| | |
|---|---|
| $^1$H NMR (CDCl$_3$ + DMSO) δ | 6.95(2H, d), 7.50(2H, d), 7.60(2H, d), 8.05(2H, d), no obvious OH absorption; |
| IR (KBr) v$_{max}$/cm$^{-1}$ | 3700–2300, 1680, 940; |
| MS (m/z) | 214[M$^+$], 196, 168, 70, 58. |

4'-Methoxycarbonyloxy-4-biphenylcarboxylic acid (4)

Methyl chloroformate (12.90 g, 0.137 mol) was added dropwise, over 10 minutes, to a stirred. cooled (5° C.) solution of compound 3 (10.00 g, 0.047 mol) in sodium hydroxide (5.44 g, 0.136 mol) and water (150 ml). During the addition a white precipitate was formed and this stirred mixture was allowed to warm to room temperature overnight. The resultant mixture was carefully acidified (pH 5) with dilute hydrochloric acid and the resultant voluminous white solid was filtered off, washed with water until acid-free and dried (phosphorus pentoxide) in vacuo.

Yield 11.87 g (93%); mesomorphic behaviour (° C.) K 253 N 300<L

| | |
|---|---|
| $^1$H NMR (CDCl$_3$ + DMSO) δ | 3.95(3H, s), 7.30(2H, d), 7.65(2H, d), 7.65(2H, d), 8.10(2H, d), no obvious OH absorption; |
| IR (KBr) $v_{max}$/cm$^{-1}$ | 3300–2300, 1760, 1670, 1260, 930; |
| MS (m/z) | 272[M$^+$], 228, 213, 185, 139, 59. |

Octyl 4'-Methoxycarbonyloxy-4-biphenylcarboxylate (5)

A solution of triphenylphosphine (3.78 g, 0.014 mol) in dry tetrahydrofuran (50 ml) was added to a stirred solution of compound 4 (3.92 g, 0.014 mol), octan-1-ol (1.88 g 0.014 mol) and diethyl azodicarboxylate (DEAD) (2.51 g 0.014 mol) in dry tetrahydrofuran (100 ml) under an atmosphere of dry nitrogen. The addition was such that the triphenylphosphine was added over 30 seconds in which time the solution became hot and the white solid (4) and orange colour (DEAD) disappeared. The resultant solution was stirred overnight, the solvent was removed in vacuo and the viscous, oily residue was purified by column chromatography (10% petrol/dichloromethane) to give a colourless solid which was recrystallised from ethanol to leave colourless plates.

Yield 5.30 g (99%); mp 46–47° C.

| | |
|---|---|
| $^1$H NMR (CDCl$_3$) δ | 0.90(3H, t), 1.20–1.55(10H, m), 1.70–1.85(2H, m), 3.95(3H, s), 4.35(2H, t), 7.30(2H, d), 7.65(2H, d), 7.65(2H, d), 7,65(2H, d), 8.10(2H, d); |
| IR (KBr) $v_{max}$/cm$^{-1}$ | 1760, 1710, 1230; |
| MS (m/z) | 384[M$^+$], 272, 228, 139, 69, 57. |

Octyl 4'-hydroxy-4-biphenylcarboxylate (6)

A solution of compound 5 (5.25 g, 0.014 mol) and aqueous ammonia (35% w/v, 100 ml) in ethanol (200 ml) was stirred for 1 h at room temperature TLC analysis (dichloromethane) revealed a complete reaction. The solvent was removed in vacuo and the white solid was recrystallised from, ethanol to give colourless crystals.

Yield 4.48 g (99%); mp 98.5–100° C.

| | |
|---|---|
| $^1$H NMR (CDCl$_3$) δ | 0.90(3H, t), 1.20–1.55(10H, m), 1.80(2H, m), 4.35(2H, t), 5.05–5.25(1H, s), 6.95(2H, d), 7.55(2H, d), 7.65(2H, d), 8.05(2H, d); |
| IR (KBr) $v_{max}$/cm$^{-1}$ | 3600–3100, 1675; |
| MS (m/z) | 326[M$^+$], 214, 197, 147, 82, 69. |

(S)-(+)-Ethyl 4-(2-(methylbutyloxy)benzoate (8)

Quantities: (S)-(–)-2-(methylbutan-1-ol (5.00 g, 0.057 mol), ethyl-4-hydroxybenzoate (7) (9.47 g, 0.057 mol), DEAD (9.93 g, 0.057 mol), triphenylphosphine (14.95 g 0.057 mol). The experimental procedure was as described for the preparation of compound 5. The crude product was purified by column chromatography (10% petrol/dichloromethane) to give a colourless oil.

Yield 12.64 g (94%).

| | |
|---|---|
| $^1$H NMR (CDCl$_3$) δ | 0.95(3H, t), 1.00(3H, d), 1.30(1H, m), 1.40(3H, t), 1.50–1.65(1H, m), 1.80–2.00(1H, m), 4.35(2H, m), 4.35(2H, q), 6.90(2H, d), 8.00(2H, d); |
| IR (neat) $v_{max}$/cm$^{-1}$ | 1715, 1255; |
| MS (m/z) | 236[M$^+$], 166, 138, 121; |
| OR | $[\alpha]_D^{23°}$ +10.3° (c = 0.04, CHCl$_3$). |

(S)-(+)-4-(2-(Methylbutyloxy)benzoic acid (9)

A mixture of compound 8 (10.40 g, 0.04 mol), sodium hydroxide (11.67 g 0.208 mol), water (23 ml) and ethanol (225 ml) was heated under reflux for 2 h. The solution was allowed to cool, to room temperature, and then acidified with dilute hydrochloric acid. The solvent was removed to leave a white solid which was dissolved in ether and washed successively with saturated sodium hydrogen carbonate solution (until no more effervescence was observed) and water. After drying the ether (MgSO4), the solvent was removed in vacuo and the white solid was recrystallised from ethanol to yield colourless crystals.

Yield 7.70 g (84%); mp 108–109° C.

| | |
|---|---|
| $^1$H NMR (CDCl$_3$) δ | 0.95(3H, t), 1.05(3H, d), 1.30(1H, m), 1.60(1H, m), 1.90(1H, m), 4.85(2H, m), 6.95(2H, d), 7.60(2H, d), no obvious OH absorption; |
| IR (KBr) vmax/cm$^{-1}$ | 3300–2300, 1675, 1260, 960; |
| MS (m/z) | 208[M$^+$], 138, 121, 70, 65, 55; |
| OR | $[\alpha]_D^{22.5°}$ +11.9° (c = 0.02, CHCl$_3$). |

(S)-(+)-Ethyl 4-(2-(methylbutyloxy)-3-(nitrobenzoate (11)

Quantities (S)-(–)-2-(methylbutan (1.94 g 0.002 mol), ethyl 4-(hydroxy-3-nitrobenzoate (10) (4.64 g, 0.022 mol), DEAD (3.83 g, 0.022 mol), triphenylphosphine (5.77 g, 0.022 mol).

The experimental procedure was as described for the preparation of compound 5. The crude product was purified by column chromatography (10% petrol/dichloromethane), to leave a pale yellow solid.

Yield 5.75 g (93%); mp 66–68° C.

| | |
|---|---|
| $^1$H NMR (CDCl$_3$) δ | 0.95(3H, t), 1.10(3H, d), 1.35(1H, m), 1.40(3H, t), 1.60(1H, m), 1.95(1H, m), 4.00(2H, m), 4.40(2H, q), 7.10(1H, d), 8.20(1H, dd), 8.50(1H, d); |
| IR (KBr) $v_{max}$/cm$^{-1}$ | 1700, 1530, 1350, 1245; |
| MS (m/z) | 281[M$^+$], 212, 183, 166, 70; |
| OR | $[\alpha]_D^{23°}$ +4.1° (c = 0.02, CHCl$_3$). |

S-(+)-4-(2-(Methylbutyloxy)-3-(nitrobenzoic acid (12)

Method 1

Compound 9 (4.00 g, 0.02 mol) was dissolved in hot glacial acetic acid (20 ml) and the resultant stirred solution was cooled to 5° C. A solution of concentrated sulphuric acid (12 ml) in glacial acetic acid (20 ml) was added, followed by the careful addition of a cooled (5° C.) solution of concentrated nitric acid (12 ml) and concentrated sulphuric acid (12 ml) in glacial acetic acid (20 ml). The mixture was then allowed to warm to 20° C. for 1 h and the resultant yellow solution was poured into an ice-water mixture (300 ml). The pale-yellow solid was filtered off, washed with water until acid-free and recrystallised from ethanol to give pale-yellow crystals.

Yield 3.45 g (72%); mp 177–178° C.

| | |
|---|---|
| $^1$H NMR (CDCl$_3$ + DMSO) δ | 0.95(3H, t), 1.05(3H, d), 1.35(1H, m), 1.60(1H, m), 1.95(1H, m), 4.00(2H, m), 7.15(1H, d), 8.20(1H, dd), 8.50(1H, d), no obvious OH absorption; |
| IR (KBr) $v_{max}/cm^{-1}$ | 3300–2400, 1705, 1530, 1350, 1250, 915; |
| MS (m/z) | 253[M$^+$], 183, 166, 138, 70; |
| OR | $[α]_D^{20°}$ +10.6° (c = 0.02, DMF). |

(S)-(+)4-(2-(Methylbutyloxy)-3-nitrobenzoic acid (12)

Method 2

Quantities: compound 11 (2.00 g, 7.12 mmol), sodium hydroxide (0.6 g, 0.015 mol), ethanol (80 ml), water (20 ml). The experimental procedure was as described for the preparation of compound 9.

Yield 1.77 g (98%).

Spectra, as for method 1.

(R)-(−)-Ethyl 4-(1-methylpheptyloxy)benzoate (13)

Quantities: Ethyl 4-(hydroxybenzoate (7) (3.83 g, 0.023 mol), (S)-(+)-octan-2-ol (3.00 g, 0.023 mol), DEAD (4.01 g. 0.023 mol). triphenylphosphine (6.04 g, 0.0023 mol). The experimental procedure was as described for the preparation of compound 5. The crude product was purified by column chromatography (10% petrol/dichloromethane) to give a colourless oil.

Yield 5.81 g (91%).

| | |
|---|---|
| $^1$H NMR (CDCl$_3$) δ | 0.90(3H, t), 1.30(3H, d), 1.35(3H, t), 1.2–1.50(8H, m), 1.50–1.85(2H, m), 4.35(2H, q), 4.45(1H, m), 6.90(2H, d), 8.00(2H, d); |
| IR (neat) $v_{max}/cm^{-1}$ | 1710, 1250; |
| MS (m/z) | 278[M$^+$], 166, 138, 121; |
| OR | $[α]_D^{23°}$ −10.2° (c = 0.03, CHCl$_3$). |

(R)-(−)-4-(1-Methylpheptyloxy)benzoic acid (14)

Quantities: compound 13 (4.00 g 0.014 mol), sodium hydroxide (115 g, 0.029 mol), ethanol (80 ml), water (20 ml). The experimental procedure was as described for the preparation of compound 9. The product was recrystallised from ethanol to give colourless crystals.

Yield 3.36 g (96%); mp 61–63° C.

| | |
|---|---|
| $^1$H NMR (CDCl$_3$) δ | 0.90(3H, t), 1.30(3H, d), 1.15–1.50(8H, m), 1.50–1.65(1H, m), 1.65–1.85(1H, m), 4.45(1H, m), 6.90(2H, d), 8.05(2H, d), no obvious OH absorption; |
| IR (KBr) $v_{max}/cm^{-1}$ | 3200–2300, 1650, 1260, 945; |
| MS (m/z) | 250[M$^+$], 138, 121; |
| OR | $[α]_D^{23°}$ −9.6° (c = 0.06, CHCl$_3$). |

(R)-(−)-Ethyl 4-(1-methylpheptyloxy)-3-nitrobenzoate (15)

Quantities: Ethyl 4-(hydroxy-3-nitrobenzoate (10) (4.85 g, 0.023 mol), (S)-(+)-octan-2-ol (3.00 g, 0.023 mol), DEAD (4.01 g, 0.023 mol), triphenylphosphine (6.03 g, 0.023 mol), The experimental procedure was as described for the preparation of compound 5 but the reaction mixture was left stirring for 4 days. The crude product was purified by column, chromatography (10% petrol/dichloromethane) to give a pale yellow oil.

Yield 6.06 g (82%).

| | |
|---|---|
| $^1$H NMR (CDCl$_3$) δ | 0.90(3H, t), 1.00–1.20(8H, m), 1.40(3H, d), 1.40(3H, t), 1.65(1H, m), 1.80(1H, m), 4.40(2H, q), 4.60(1H, m), 7.10(1H, d), 8.15(1H, dd), 8.45(1H, d); |
| IR (neat) $v_{max}/cm^{-1}$ | 1725, 1540, 1370, 1245, 940; |
| MS (m/z) | 323[M$^+$], 212, 183, 166, 112, 83, 70, 57; |
| OR | $[α]_D^{23°}$ −16.1° (c = 0.05, CHCl$_3$). |

(R)-(−)-4-(1-Methylheptyloxy)-3-(nitrobenzoic acid (16)

Quantities: compound 15 (5.00 g 0.015 mol), sodium hydroxide (1.24 g, 0.031 mol), ethanol (160 ml), water (40 ml). The experimental procedure was as described for the preparation of compound 9. The resultant solid was recrystallised from ethanol to give a pale yellow solid.

Yield 4.38 g (99%); mp 64–66° C.

| | |
|---|---|
| $^1$H NMR (CDCl$_3$) δ | 0.90(3H, t), 1.40(3H,d), 1.20–1.60(8H, m), 1.70(1H, m), 1.85(1H, m), 4.65(1H, m), 7.15(1H, d), 8.25(1H, dd), 8.50(1H, d); |
| IR (KBr) $v_{max}/cm^{-1}$ | 3400–2300, 1700, 1540, 1355, 1260, 940; |
| MS (m/z) | 295[M$^+$], 183, 166, 112, 83, 70, 57; |
| OR | $[α]_D^{23°}$ −13.9° (c = 0.05, CHCl$_3$). |

(S)-(+)-Octyl 4'-[4-(2-methylbutyloxy)-3-nitrobenzoyloxy]-4-biphenylcarboxylate (17)

A solution of DCC (1.47 g, 7.12 mmol) and DMAP (0.08 g, 0.66 mmol) in dichloromethane (30 ml was added to a stirred solution of compound 10 (1.50 g, 5.93 mmol) and compound 6 (1.93 g, 5.93 mmol) in dichloromethane (30 ml). The resultant solution was stirred, overnight under dry conditions (CaCl$_2$) after which time the white precipitate (DCU) was filtered off and the solvent removed in vacuo. The residue was purified by column chromatography (10% petrol/dichloromethane) and recrystallised from ethanol to yield pale yellow crystals.

Yield 1.82 g (55%); mesomorphic behaviour (° C.) K 85.0) S$_C^*$ 71.7) S$_A^*$ 126.8 I.

| | |
|---|---|
| $^1$H NMR (CDCl$_3$) δ | 0.90(3H, t), 0,95(3H, t), 1.05(3H, d), 1.15–1.60(11H, m), 1.60(1H, m), 1.80(2H,m), 2.00(1H, m), 4.05(2H, m), 4.35(2H, t), 7.20(1H, d), 7.30(2H, d), 7.70(2H, d), 7.70(2H, d), 8.10(2H, d), 8.35(1H, dd), 8.70(1H, d); |
| IR (KBr) $v_{max}/cm^{-1}$ | 1740, 1725, 1540, 1355, 1235; |
| MS (m/z) | 561[M$^+$], 326, 236, 166; |
| OR | $[α]_D^{23°}$ +2.2° (c = 0.03, CHCl$_3$). |

(R)-(−)-Octyl 4'-[4-(1-methylheptyloxy)-3-(nitrobenzoyloxy]-4-biphenylcarboxylate (18)

Quantities: compound 16 (2.00 g, 6.80 mmol), compound 6 (2.22 g, 6.80 mmol), DCC (1.68 g 8.16 mmol), DMAP (0.10 g, 0.76 mmol). The experimental procedure was as described- for the preparation of compound 17. The crude product was purified by column chromatography (10% petrol/dichloromethane) and recrystallised from ethanol. The ethanol solution was cooled rapidly from boiling (78° C.) with liquid nitrogen and then left at −20° C. overnight to give a sticky, pale yellow solid.

Yield 1.49 g (36%); mesomorphic behaviour (° C.) K 37.0 S$_C^*$ 56.4 S$_A^*$ 62.5 I.

| | |
|---|---|
| ¹H NMR (CDCl₃) δ | 0.90(3H, t), 0.90(3H, t), 1.40(3H, d), 1.20–1.60(18H, m) 1.60–1.95(4H, m), 4.35(2H, t), 4.65(1H, m), 7.20(1H, d), 7.30(2H, d), 7.65(2H, d), 7.70(2H, d), 8.10(2H, d), 8.35(1H, dd), 8.65(1H, m); |
| IR (KBr) $v_{max}/cm^{-1}$ | 1760, 1715, 1540, 1355, 1240; |
| Ms (m/z) | 603[M⁺], 326, 166; |
| OR | $[\alpha]_D^{23°}$ −5.4° (c = 0.05, CHCl₃). |

4-(Methoxycarbonyloxybenzoic acid (20)

Quantities: 4-(hydroxybenzoic acid (19) (10.00 g, 0.07 mol), methyl chloroformate (11.34 g, 0.12 mol), sodium hydroxide (8.32 g, 0.208 mol), water (240 ml). The experimental procedure was as described for the preparation of compound 4. The product was recrystallised from ethanol to yield white crystals.

Yield 12.00 g (82%); mp 177–178° C.

| | |
|---|---|
| ¹H NMR (CDCl₃) δ | 3.95(3H, s), 7.30(2H, d), 8.15(2H, d), no obvious OH absorption; |
| IR (KBr) $v_{max}/-1$ | 3300–2300, 1750, 1680, 1265, 940; |
| MS (m/z) | 196[M⁺], 152, 135, 59. |

Octyl 4-(methoxycarbonyloxybenzoate (21)

Quantities compound 20 (10.00 g, 0.049 mol), octan-1-ol (6.38 g, 0.049 mol), DEAD (8.53 g, 0.049 mol), triphenylphosphine (12.85 g, 0.049 mol). The experimental procedure was as described for the preparation of compound 5. The crude product was purified by column chromatography (10% petrol/dichloromethane) to give a colourless oil which solidified on standing.

Yield 13.76 g (89%); mp 28–30° C.

| | |
|---|---|
| ¹H NMR (CDCl₃) δ | 0.90(3H, t), 1.20–1.50(10H, m), 1.70–1.85(2H, m), 3.95(3H, s), 4.30(2H, t), 7.25(2H, d), 8.10(2H, d); |
| IR (KBr) $v_{max}/-1$ | 1765, 1720, 1250; |
| MS (m/z) | 308[M⁺], 196, 179, 152, 135. |

Decyl 4-(methoxycarbonyloxybenzoate (22)

Quantities: compound 20 (10.00 g, 0.051 mol), decan-1-ol (8.08g, 0.051 mol). DEAD (8.89 g, 0.051 mol), triphenylphosphine (13.38 g, 0.051 mol), THF (100 ml). The experimental procedure was as described for the preparation of compound 5. The crude product was purified by column chromatography (20% petrol/dichloromethane) to give a colourless oil.

Yield 16.53 g (96%).

| | |
|---|---|
| ¹H NMR (CDCl₃) δ | 0.85(3H, t), 1.15–1.55(14H, m), 1.75(2H, m), 3.90(3H, s), 4.30(2H, t), 7.25(2H, d), 8.10(2H, d); |
| IR (neat) $v_{max}/cm^{-1}$ | 1770, 1720, 1260, 1220; |
| MS (m/z) | 336[M⁺], 197, 179, 152, 135. |

Octyl 4-(hydroxybenzoate (23)

Quantities: compound 21 (13.76 g, 0.045 mol), ethanol (150 ml), aqueous ammonia (35% w/v, 150 ml). The experimental procedure was as described for the preparation of compound 6.

Yield 9.56 g (85%, mp 46–49° C.

| | |
|---|---|
| ¹H NMR (CDCl₃) δ | 0.90(3H, t), 1.20–1.55(10H, m), 1.75–1.90(2H, m), 4.05(2H, t), 6.95(2H, d), 8.05(2H, d), no obvious OH absorption; |
| IR (KBr) $v_{max}/cm^{-1}$ | 3600–3100, 1670; |
| MS (m/z) | 250[M⁺], 138, 121. |

Decyl 4-(hydroxybenzoate (24)

Quantities: compound 22 (16.53 g, 0.049 mol), ethanol (200 ml), aqueous ammonia (35% w/v 100 ml). The experimental procedure was as described for the preparation of compound 6. After removing the solvent in vacuo the crude product was purified by column chromatography (4% ethanol/dichloromethane) to yield a colourless solid.

Yield 12.07 g (88%); mp 44–45° C.

| | |
|---|---|
| ¹H NMR (CDCl₃) δ | 0.90(3H, t), 1.20–1.60(14H, m), 4.05(2H, t), 7.00(2H, d), 8.45(2H, d), 8.95(1H, s); |
| IR (KBr) $v_{max}cm^{-1}$ | 3600–3100, 1675, 1280; |
| MS (m/z) | 278[M⁺], 138, 121, 93, 65, 55. |

(S)-(+)-4'-(2-(Methylbutyloxy)-4-(biphenylcarboxylic acid (26)

Quantities: (S)-4-cyano-4-(2-methylbutyloxy) cyanobiphenyl (25) (5.00 g, 0.02 mol), concentrated sulphuric acid (10 ml), water (10 ml), glacial acetic acid (100 ml). The experimental procedure was as described for the preparation of compound 2 to give a white solid which was heated under reflux with a further, fresh acid mixture. The final white solid was recrystallised from glacial acetic acid to yield a white, crystalline solid.

Yield 3.00 g (83%); mesomorphic behaviour (° C.) K 240 N 2512 I (lit. K 239 N 249 I).

| | |
|---|---|
| ¹H NMR (CDCl₃ + DMSO) δ | 0.95(3H, t), 1.05(3H, d), 1.30(1H, m), 1.60(1H, m), 1.90(1H, m), 4.85(2H, m), 7.00(2H, d), 7.55(2H, d), 7.65(2H, d), 8.10(2H, d), no obvious OH absorption; |
| IR (KBr) $v_{max}/cm^{-1}$ | 3300–2300, 1680, 1250, 950; |
| MS (m/z) | 284[M⁺], 214, 197, 94; |
| OR | $[\alpha]_D^{22°}$ +15.0° (c = 0.02, DMF). |

(S)-(+)4-(2-(Methylbutyloxy)-3-(nitro-4'-biphenylcarboxylic acid (27)

Quantities: compound 26 (3.00 g, 0.01 mol), concentrated sulphuric acid (18 ml), concentrated nitric acid (9 ml), glacial acetic acid (40 ml). The experimental procedure was as described for the preparation of compound 12 to give a pale yellow solid which was recrystallised from ethanol.

Yield 3.00 g (83%); mesomorphic behaviour (° C. ) K 145.2 $S_X$ 150.2 $S_C^*$ 174

| | |
|---|---|
| ¹H NMR (CDCl₃) δ | 1.00(3H, t), 1.10(3H, d), 1.35(1H, m), 1.60(1H, m), 1.95(1H, m), 4.00(2H, m), 7.20(1H, d), 7.65(2H, d), 7.80(1H, dd), 8.10(1H, d), 8.20(1H, d), no obvious OH absorption; |
| IR (KBr) $v_{max}/cm^{-1}$ | 3700–3300, 3300–2300, 1690, 1540, 1350, 1260, 960; |

MS (m/z)   329[M+], 284, 259, 214, 71;
OR   [α]$_D$ $^{22°}$ +6.8° (c = 0.03, CHCl$_3$).

(S)-(+)-Octyl 4-[4-(2-methylbutyloxy)-3-nitro-4'-biphenylcarbonyloxy]benzoate (28)

Quantities: compound 27 (1.50 g, 4.56 mmol), compound 23 (1.14 g, 4.56 mmol), DCC (1.13 g, 5.47 mmol), DMAP (0.06 g, 0.51 mmol), dichloromethane (50 ml). The experimental procedure was as described for the preparation of compound 17. The product was purified by column chromatography (10% petrol/dichloromethane) and recrystallized from acetonitrile to give pale yellow crystals.

Yield 0.80 g (31%); mesomorphic behaviour (° C.) K 67.0 (S$_C^*$ 62.0) S$_A^*$ 132.9 I.

$^1$H NMR   0.90(3H, t), 0.95(3H, t), 1.10(3H, d), 1.20–1.55(11H, m),
(CDCl$_3$) δ   1.60(1H, m), 1.80(2H, m), 2.00(1H, m), 4.00(2H, m),
   4.35(2H, t), 7.20(1H, d), 7.35(2H, d), 7.70(2H, d), 7.80(1H,
   dd), 8.15(1H, d), 8.15(2H, d), 8.30(2H, d);
IR (KBr)   1740, 1705, 1535, 1355, 1265, 1070;
v$_{max}$cm$^{-1}$
MS (m/z)   561[M+], 326, 166;
OR   [α]$_D$ $^{23°}$ +3.8 (c = 0.03, CHCl$_3$).

4-(Methoxycarbonyloxy-3-(nitrobenzoic acid (30)

Quantities: 4-(hydroxy-3-(nitrobenzoic acid (29) (25.00 g, 0.137 mol), methyl chloroformate (21.20 g, 0.224 mol), sodium hydroxide (15.90 g. 0.397 mol), water (425 ml). The experimental procedure was as described for the preparation of compound 4. The product was recrystallised from ethanol to give pale yellow crystals.

Yield 28.42 g (86%); mp 152–154° C.

$^1$H NMR   4.00(3H, s), 7.45(1H, d), 8.35(1H, d), 8.80(1H, d), no
(CDCl$_3$) δ   obvious OH absorption
IR (KBr)   3300–2300, 1780, 1700, 1540, 1350, 1245, 940;
v$_{max}$/cm$^{-1}$
MS (m/z)   241[M+], 166, 150, 136, 119, 90, 73.

Octyl 4'-[4-(methoxycarbonyloxy)-3-(nitrobenzoylozy]-4-biphenylcarboxylate ) (31)

Quantities compound 30 (2.41 g, 0.01 mol), compound 6 (3.26 g, 0.01 mol), DEAD (1.74 g, 0.01 mol), triphenylphosphine (2.62 g, 0.01 mol). The experimental procedure was as described for the preparation of compound 9. The product was purified by column chromatography (10% petrol/dichloromethane) and finally recrystallised from ethanol to give a pale yellow solid.

Yield 1.75 g; mp 125–126° C.

$^1$H NMR   0.90(3H, t), 1.20–1.55(10H, m), 1.80(2H, m), 4.00(3H, s),
(CDCl$_3$) δ   4.35(2H, t), 7.35(1H, d), 7.50(2H, d), 7.70(2H, d), 7.70(2H,
   d), 8.00(2H, d), 8.50(1H, dd), 9.00(1H, d);
IR (KBr)   1735, 1720, 1705, 1540, 1345, 1260;
v$_{max}$/cm$^{-1}$
MS (m/z)   549[M+], 491, 327, 214, 166, 120.

(R)-(−)-Octyl 4'-[4-(1-ethylheptyloxy)-3-nitrobenzoyloxy]-4-biphenylcarboxylate (32)

Quantities: compound 31 (1.20 g, 2.44 mmol), (S)-(+)-nonan-3-ol (0.35 g, 2.44 mmol), DEAD (43 g, 2.44 mmol), triphenylphosphine (0.64 g, 2.44 mmol). The experimental procedure was as described for the preparation of compound 5. The product was purified by column chromatography (10% petrol/dichloromethane) and recrystallised from ethanol to give pale yellow crystals.

Yield 0.50 g (33%); mp 39–40° C.

$^1$H NMR   0.90(6H, 2t), 1.00(3H, t), 1.15–1.60(18H, m), 1.80(6H, m),
(CDCl$_3$) δ   4.35(2H, t), 4.50(1H, m), 7.15(1H, d), 7.30(2H, d), 7.65(2H,
   d), 7.70(2H, d), 8.10(2H, d), 8.30(1H, dd), 8.65(1H, d) ;
IR (KBr)   1720, 1705, 1530, 1355, 1240;
v$_{max}$/cm$^{-1}$
MS (m/z)   617[M+], 326, 292, 214, 166;
OR   [α]$_D$ $^{21°}$ −1.26° (c = 0.02, CHCl$_3$).

(R)-(−)-Octyl 4'-[4-(1-methylheptyloxy)benzoyloxy]-4-biphenylcarboxylate (33)

Quantities: compound 15(1.40 g, 5.60 mmol), compound 6 (1.83 g 5.60 mmol), DCC (1.39 g, 6.72 mmol), DMAP (0.08 g, 0.62 mmol). The experimental Procedure was as described for the preparation of compound 17. The compound was purified by column chromatography [(i) 10% petrol/dichloromethane, (ii) 50% petrol/dichloromethane, (iii) dichloromethane] and recrystallised from ethanol to give colourless crystals.

Yield 3.01 g (96%); mesomorphic behaviour (° C.) K 57.4 S$_C^*$ 64.4 N$^*$ 69.7 I.

$^1$H NMR   0.90(6H, 2t), 1.20–1.65(20H, m), 1.35(3H, d), 1.80(2H, m),
(CDCl$_3$) δ   4.35(2H, t), 4.50(1H, m), 6.95(2H, d), 7.30(2H, d), 7.65(4H,
   2d), 8.10(2H, d), 8.15(2H, d);
IR (KBr)   1720, 1255;
v$_{max}$/cm$^{-1}$
MS (m/z)   558[M+], 430, 325, 233, 121;
OR   [α]$_D$ $^{19°}$ −4.5° (c = 0.005, CHCl$_3$).

(R)-(−)-1-Bromo-3-fluoro-4-(1-methylheptyloxy)benzene (35)

Quantities: 4-(bromo-3-fluorophenol (34) (7.33 g, 0.038 mol), (S)-(+)-octan-2-ol (5.00 g, 0.038 mol), DEAD (6.69 g, 0.038 mol), triphenylphosphine (10.07 g, 0.038 mol). The experimental procedure was as described for the preparation of compound 5. The product was purified by column chromatography (70% petrol/dichloromethane) to give a colourless oil.

Yield 10.62 g (92%).

$^1$H NMR   0.85(3H, t), 1.20–1.85(13H, m), 4.30(1H, m), 6.85(1H, t),
(CDCl$_3$) δ   7.15(1H, ddd), 7.20(1H, dd);
IR (neat)   1265;
v$_{max}$/cm$^{-1}$
MS (m/z)   304[M+], 302[M+], 192, 190;
OR   [α]$_D$ $^{26°}$ −1.7° (c = 0.04, CHCl$_3$).

(R)-(−)-3-(Fluoro-4-(1-methylheptyloxy)benzoic acid (36)

A solution of n-butyllithium (2.5 M, 17.2 ml, 0.043 mol) in hexanes was added, dropwise, to a cooled (−78° C.), stirred solution of compound 35 (10.00 g, 0.033 mol) in dry THF (100 ml) under a dry nitrogen atmosphere and left to stir for 20 min. The resultant solution was poured into a slush of solid carbon dioxide and dry THF. This was left overnight at room temperature and then acidified with dilute hydrochloric acid. The THF/water azeotrope was evaporated off in vacuo and the residue was dissolved in diethyl ether, washed with water and then extracted with 5% sodium hydroxide solution which was acidified with dilute hydrochloric acid. The product was extracted with diethyl ether and the ethereal solution was wished with water until acid-free dried (MgSO$_4$) and evaporated in vacuo to leave an off-white, semi-solid.

Yield 4.15 g (47%).

| $^1$H NMR (CDCl$_3$) δ | 0.85(3H, t), 1.35(3H, d), 1.15–1.90(10H, m), 4.50(1H, m), 7.00(1H, t), 7.80(1H, d), 7.85(1H, d), 10.5–11.5(1H, s); |
|---|---|
| IR (KBr) ν$_{max}$/cm$^{-1}$ | 3500–2400, 1690, 1280; |
| MS (m/z) | 268[M$^+$], 156, 139, 112, 83; |
| OR | [α]$_D$ $^{18°}$ −7.0° (c = 0.04, CHCl$_3$). |

(R)-(−)-Octyl 4'-[4-(1-methylheptyloxy)-3-(fluorobenzoyloxy]-4-biphenylcarboxylate (37)

Quantities: compound 36 (2.00 g, 7.46 mmol), compound 6 (2.43 g, 7.46 mmol), DCC (1.85 g, 8.96 mmol), DMAP (0.10 g, 0.82 mmol). The experimental procedure was as described for the preparation of compound 17. The crude product was purified by column chromatography (10% petrol/dichloromethane) and recrystallised from ethanol to give a white, crystalline solid.

Yield 1.50 g (35%), mesomorphic behaviour (° C.) K 61.2 S$_C^*$ 71.7 I.

| $^1$H NMR (CDCl$_3$) δ | 0.90(6H, 2t), 1.40(3H, d), 1.20–1.95(22H, m), 4.35(2H, t), 4.55(1H, m), 7.05(1H, t), 7.30(2H, d), 7.05(1H, t), 7.65(4H, 2d), 7.90(1H, d), 8.00(1H, m), 8.10(2H, d). |
|---|---|
| IR (KBr) ν$_{max}$/cm$^{-1}$ | 1725, 1705, 1280. |
| MS (m/z) | 504[M$^+$], 251, 139. |
| OR | [α]$_D$ $^{26°}$ −2.3° (c = 0.01, CHCl$_3$). |

(S)-(+)-2-(2-Methylbutyloxy)benzonitrile (39)

Quantities: 2-(hydroxybenzonitrile) (38) (5.00 g, 0.042 mol), (S)-(−)-2-(methylbutan-1-(3.70 g, 0.042 mol), DEAD (7.31 g, 0.042 mol), triphenylphosphine (11.01 g, 0.042 mol), THF (100 ml). The experimental procedure was as described for the preparation of compound 5. The crude product was first washed with a 5% sodium hydroxide solution and then purified by column chromatography (10% petrol/dichloromethane) to yield a fawn coloured oil.

Yield 4.88 g (61%).

| $^1$H NMR (CDCl$_3$) δ | 0.95(3H, t), 1.05(3H, d), 1.35(1H, m), 1.60(1H, m), 1.95(1H, m), 3.90(2H, m), 7.00(1H, t), 7.00(1H, dd), 7.50(1H, t), 7.50(1H, dd); |
|---|---|
| IR (neat) ν$_{max}$/cm$^{-1}$ | 2215, 1260; |
| MS (m/z) | 189[M$^+$], 119; |
| OR | [α]$_D$ $^{26°}$ +8.5° (c = 0.03, CDCl$_3$). |

(R)-(−)-2-(1Methylheptyloxy)benzonitrile (40)

Quantities: 2-(hydroxybenzonitrile) (38) (9.17 g, 0.077 mol), (S)-(+)-octan-2-ol (10.00 g, 0.077 mol), DEAD (13.41 g, 0.077 mol), triphenylphosphine (20.20 g, 0.077 mol). The experimental procedure was as described for the preparation of compound 5. The crude product was purified by column chromatography (20% petrol/dichloromethane) to give a colourless oil.

Yield 17.70 g (100%).

| $^1$H NMR (CDCl$_3$) δ | 0.90(3H, t), 1.35(3H, d), 1.15–1.90(10H, m), 4.50(1H, m), 6.90–7.00(2H, m), 745–7.55(2H, d); |
|---|---|
| IR (neat) ν$_{max}$/cm$^{-1}$ | 2215, 1260; |
| MS (m/z) | 231[M$^+$], 119, 111, 84, 69; |
| OR | [α]$_D$ $^{23°}$ −55.6° (c = 0.14, CHCl$_3$). |

(S)-(+)-5-Bromo-2-(2-methylbutyloxy)benzonitrile (41)

A mixture of compound 39 (4.25 g, 0.-22 mol), bromine (12.31 g, 0.077 mol was then added and heating continued for another 24 h. The resultant solution was washed with a saturated solution of sodium thiosulphate and finally with water. The dichloromethane solution was dried (MgSO$_4$) and evaporated in vacuo and the crude oil was purified by column chromatography (10% petrol/dichloromethane) to yield a fawn oil.

Yield 5.56 g (94%).

| $^1$H NMR (CDCl$_3$) δ | 0.95(3H, t), 1.05(3H, d), 1.35(1H, m), 1.60(1H, m), 1.95(1H, ,), 3.85(2H, m), 6.85(1H, d), 7.60(1H, dd), 7.65(1H, d); |
|---|---|
| IR (neat) ν$_{max}$/cm$^{-1}$ | 2215, 1260; |
| MS (m/z) | 269[M$^+$], 267[M$^+$], 199, 197, 70, 54; |
| OR | [α]$_D$ $^{21.5°}$ +7.1 (c = 0.04, CHCl$_3$). |

(R)-(−)-5-Bromo-2-(1-methylheptyloxy)benzonitrile (42)

Quantities: compound 40 (12.34 g, 0.054 mol), bromine (17.15 g, 0.0107 mol), chloroform (100 ml). The experimental procedure was as described for the preparation of compound 41. The crude product was purified by column chromatography (20% petrol/dichloromethane) to give a fawn oil.

Yield 15.50 g (93%).

| $^1$H NMR (CDCl$_3$) δ | 0.85(3H, t), 1.45(3H, d), 1.15–1.55(8H, m), 1.60(1H, m) 1.80(1H, m), 4.45(1H, m), 6.85(1H, d), 7.60(1H, dd), 7.65(1H, d); |
|---|---|
| IR (neat) ν$_{max}$/cm$^{-1}$ | 2220, 1255; |
| MS (m/z) | 311[M$^+$], 309[M$^+$], 199, 197, 112, 83, 70, 57; |
| OR | [α]$_D$ $^{28°}$ −28.3° (c = 0.03, CHCl$_3$). |

(S)-(+)-3-Cyano-4-(2-methylbutyloxy)benzoic acid (43)

Quantities: compound 41 (5.00 g, 0.016 mol), n-butyllithium (2.5 M, 7.2 ml, 0.018 mol), THF (100 ml). The experimental procedure was as described for compound 36 except that the n-butyllithium was added between −90° C. and −100° C. Acidification of the resultant benzoic acid lithium salt was achieved by boiling with glacial acetic acid. The benzoic acid was crashed out of solution by diluting with a large volume of water, the resultant product was washed with water (until acid-free) and then purified as described for compound 36 to leave an off-white semi-solid.

Yield 4.04 g (91%).

| $^1$H NMR (CDCl$_3$) δ | 0.95(3H, t), 1.10(3H, d), 1.35(1H, m), 1.60(1H, m), 2.00(1H, m), 4.00(2H, m), 7.05(1H, d), 8.25(1H, dd), 8.30(1H, d), no obvious OH absorption; |
|---|---|
| IR (KBr) ν$_{max}$/cm$^{-1}$ | 3400–2400, 2220, 1710, 1260, 920; |

| | |
|---|---|
| MS (m/z) | 233[M⁺], 163, 119, 71; |
| OR | $[\alpha]_D^{28.5°}$ +9.9° (c = 0.04, CHCl₃). |

(R)-(−)-3-Cyano-4-(1-methylheptyloxy)benzoic acid (44)

Quantities: compound 42 (5.00 g, 0.016 mol), n-butyllithium (2.5 M, 7.2 ml, 0.018 mol), THF (100 ml).

The experimental procedure was as described for the preparation of compound 36 to give a fawn solid.

Yield 3.23 g (73%); mp 78–80° C.

| | |
|---|---|
| ¹H NMR (CDCl₃) δ | 0.90(3H, t), 1.35(3H, d), 1.15–1.95(10H, m), 4.60(1H, m), 7.00(1H, d), 8.25(1H, dd), 8.30(1H, d), no obvious OH absorption; |
| IR (KBr) $v_{max}$/cm-1 | 3400–2500, 2215, 1695, 1260; |
| MS (m/z) | 275[M⁺], 163, 146, 112, 83, 71; |
| OR | $[\alpha]_D^{22°}$ −9.7° (c = 0.04, CHCl₃). |

(S)-(+)-Octyl 4'-[3-cyano-4-(2-methylbutyloxy)benzoyloxy]-4-biphenylcarboxylate (45)

Quantities: compound 43 (1.42 g, 6.13 mmol), compound 6 (2.00 g, 6.13 mmol), DCC (1.52 g, 7.36 mmol), DMAP (0.08 g, 0.67 mmol).

The experimental procedure was as described for the preparation of compound 17. The product was purified by column chromatography (20% petrol/dichloromethane) and recrystallised from ethanol to give white crystals.

Yield 1.00 g (30%); mesomorphic behaviour (° C.) K126.5S$_A$*133.3I.

| | |
|---|---|
| ¹H NMR (CDCl₃) δ | 0.90(3H, t), 0.95(3H, t), 1.10(3H, d), 1.20–2.10(15H, m), 4.00(2H, m), 4.35(2H, t), 7.10(1H, d), 7.30(2H, d), 7.65(2H, d), 7.70(2H, d), 8.10(2H, d), 8.35(1H, dd), 8.45(1H, d); |
| IR (KBr) $v_{max}$/cm⁻¹ | 2220, 1735, 1725, 1245; |
| MS (m/z) | 541[M⁺],286, 216, 146, 71; |
| OR | $[\alpha]_D^{25°}$ +3.9° (c = 0.01, acetone). |

(R)-(−)-Octyl 4'-[3-cyano-4-(1-methylheptyloxy)benzoyloxy]-4-biphenylcarboxylate (46)

Quantities: compound 44 (1.50 g, 5.45 mmol), compound 6 (1.78 g, 5.45 mmol), DCC (1.35 g, 6.54 mmol), DMAP (0.07 g, 0.57 mmol).

The experimental procedure was as described for the preparation of compound 17. Purification was by column chromatography with the following solvent systems: (i) 30% petrol/dichloromethane, (ii) 20% diethyl ether/petrol, (iii) 30% diethyl ether/petrol. Attempted recrystallisation with the following solvents, ethanol, ethanol and ethyl acetate, methanol and acetonitrile, in each case gave a jelly-like mass. The removal of all solvents in vacuo left a colourless, sticky solid.

Yield 1.41 g (44%); mesomorphic behaviour (° C.) K?S$_C$*52.1S$_A$*64.5I.

| | |
|---|---|
| ¹H NMR (CDCl₃) δ | 0.90(6H, 2t), 1.45(3H, d), 1.20–1.95(22H, m), 4.35(2H, t), 4.65(1H, m), 7.05(1H, d), 7.30(2H, d), 7.65(2H, d), 7.70(2H, d), 8.10(2H, d), 8.35(1H, dd), 8.45(1H, d); |
| IR (KBr) $v_{max}$/cm⁻¹ | 2215, 1730, 1710, 1245; |

| | |
|---|---|
| MS (m/z) | 583[M⁺], 258, 146; |
| OR | $[\alpha]_D^{20°}$ −14.6° (c = 0.03, CHCl₃). |

(S)-(+)-3-Cyano-4-(2-methylbutyloxy)phenylboronic acid (47)

Quantities: compound 41 (3.00 g, 0.012 mol), n-butyllithium (2.5 M, 5.28 ml, 0.013 mol), trimethyl borate (2.70 g, 0.024 mol).

The experimental procedure for the preparation of the lithium salt was as described in the preparation of compound 43. A solution of trimethyl borate (2.70 g, 0.024 mol) in dry THF (10 ml) was added dropwise to the lithium salt solution. The resultant mixture was allowed to warm to room temperature overnight whilst stirring and dilute hydrochloric acid was then added. The THF/water azeotrope was removed in vacuo and the remaining residue was dissolved in diethyl ether and washed with water until acid-free. The ether was dried (MgSO₄) and removed in vacuo to leave a fawn solid.

Yield 2.54 g (95%); mp. 186–188° C.

| | |
|---|---|
| ¹H NMR (CDCl₃) δ | 0.95(3H, t), 1.10(3H, d), 1.40(1H, m), 1.65(1H, m), 2.00(1H, m), 4.00(2H, m), 7.10(1H, d), 8.30(1H, dd), 8.35(1H, d), no obvious OH absorption; |
| IR (KBr) $v_{max}$/cm⁻¹ | 3700–3100, 2215, 1265; |
| MS (m/z) | 305[M⁺], 135; |
| OR | $[\alpha]_D^{21°}$ +6.2° (c = 0.006, CHCl₃). |

(R)-(−)-3-Cyano-4-(1-methylheptyloxy)phenylboronic acid (48)

Quantities: compound 42 (5.00 g, 0.016 mol), n-butyllithium (2.5 M, 7.2 ml, 0.018 mol), trimethyl borate (3.33 g, 0.032 mol), THF (100 ml).

The procedure was described for the preparation of compounds 47.

Yield 3.90 g (87%); mp 67–70° C.

| | |
|---|---|
| ¹H NMR (CDCl₃) δ | 0.90(3H, t), 1.35(3H, d), 1.15–1.95(10H, m), 4.60(1H, m), 7.05(1H, d), 8.30(1H, dd), 8.35(1H, d); |
| IR (KBr) $v_{max}$/cm⁻¹ | 3700–3100, 2215, 1260; |
| MS (m/z) | 275[M⁺], 236, 119, 69; |
| OR | $[\alpha]_D^{25°}$ −47.1° (c = 0.01, CHCl₃). |

(S)-(+)-5-Hydroxy-2-(2-methylbutyloxy)benzonitrile (49)

A mixture of compound 47 (3.00 g, 0.014 mol), hydrogen peroxide (30% w/v, 150 ml) and THF (200 ml) was heated under reflux for 3 h. The water/THF mixture was removed in vacuo and the oily residue was dissolved in diethyl ether and washed with water. The ether was dried (MgSO₄) and evaporated in vacuo to give a viscous, fawn oil.

Yield 2.01 g(70%).

| | |
|---|---|
| ¹H NMR (CDCl₃) δ | 0.90(3H, t), 1.05(3H, d), 1.35(1H, m), 1.60(1H, m), 1.90(1H, m), 3.80(2H, m), 6.25–6.50(1H, s), 6.85(1H, dd), 7.05(1H, d), no obvious OH absorption; |
| IR (neat) $v_{max}$/cm⁻¹ | 3700–3100, 2220, 1230; |

| | |
|---|---|
| MS (m/z) | 205[M⁺], 135; |
| OR | $[\alpha]_D^{22°}$ +8.5 (c = 0.02, CHCl₃). |

(R)-(−)-5-Hydroxy-2-(1-methylheptyloxy)benzonitrile (50)

Quantities: compound 48 (5.32 g, 0.019 mol), hydrogen peroxide (30% w/v, 50 ml), THF (100 ml).

The experimental procedure was as described for the preparation of compound 49 to yield a viscous, fawn oil which solidified on standing.

Yield 2.92 g (62%); mp 34–36° C.

| | |
|---|---|
| ¹H NMR (CDCl₃) δ | 0.85(3H, t), 1.30(3H, d), 1.20–1.85(10H, m), 4.35(1H, m), 6.85(1H, d), 7.05(1H, dd), 7.05(1H, d), no obvious OH absorption; |
| IR (KBr) $v_{max}/cm^{-1}$ | 3700–3000, 2215, 1230; |
| MS (m/z) | 247[M⁺], 135, 55; |
| OR | $[\alpha]_D^{21°}$ −46.0° (c = 0.04, CHCl₃). |

(R)-(−)-2-(1-Methylheptyloxy)benzotrifluoride (52)

Quantities: 2-hydroxybenzotrifluoride (51) (5.00 g, 0.031 mol), (S)-(+)-octan-2-ol (4.00 g, 0.031 mol), DEAD (5.37 g, 0.031 mol), triphenylphosphine (8.09 g, 0.031 mol).

The experimental procedure was as described for the preparation of compound 5. The product was purified by column chromatography (50% petrol/dichloromethane) to yield a colourless oil.

Yield 5.00 g(59%).

| | |
|---|---|
| ¹H NMR (CDCl₃) δ | 0.90(3H, t), 1.15–1.85(13H, m), 4.45(1H, m), 6.95(2H, 2m), 7.45(1H, m), 7.55(1H, m); |
| IR (neat) $v_{max}/cm^{-1}$ | 1255; |
| MS (m/z) | 274[M⁺], 183, 162, 142, 112; |
| OR | $[\alpha]_D^{20°}$ −23.3° (c = 0.02, CHCl₃). |

(R)-(−)-5-Bromo-2-(1-methylheptyloxy)benzotrifluoride (53)

Quantities: compound (52) (4.87 g, 0.018 mol), bromine (5.68 g, 0.036 mol), chloroform 100 mol).

The experimental procedure was as described for the preparation of compound 41 except only one portion of bromine was used. The product was purified by column chromatography (50%) petrol/dichloromethane to give a colourless oil.

Yield 6.02 g (95%).

| | |
|---|---|
| ¹H NMR (CDCl₃) δ | 0.85(3H, t), 1.20–1.80(10H, m), 1.40(3H, d), 4.40(1H, m), 6.85(1H, d), 7.35(1H, dd), 7.60(1H, d); |
| IR (neat) $v_{max}/cm^{-1}$ | 1250; |
| MS (m/z) | 304[M⁺], 302[M⁺], 192; |
| OR | $[\alpha]_D^{26°}$ −12.0° (c = 0.03, CHCl₃). |

(R)-(−)-3- α,α,α-Trifluoromethyl-4-(1-methylheptyloxy)benzoic acid (54)

Quantities: compound 53 (4.00 g, 0.011 mol),n-butyllithium (2.5 M, 5.44 ml, 0.014 mol), THF (100 ml).

The experimental procedure was as described for the preparation of compound 36 to give an off-white solid.

Yield 2.82 g (81%); mp 92–95° C.

| | |
|---|---|
| ¹H NMR (CDCl₃) δ | 0.90(3H, t), 1.40(3H, d), 1.20–1.95(10H, m), 4.60(1H, m), 7.00(1H, d), 8.25(1H, dd), 8.30(1H, d), no obvious OH absorption; |
| IR $v_{max}/cm^{-1}$ | 3300–2300, 1700, 1260, 940; |
| MS (m/z) | 318[M⁺],276, 164, 146, 121, 83, 71, 56; |
| OR | $[\alpha]_D^{21°}$ −45.5° (c = 0.03, CHCl₃). |

(R)-(−)-Octyl 4'-[4-(1-methylheptyloxy)-3-ααα-trifluoromethylbenzoyloxy]-4-biphenylcarboxylate (55)

Quantities: compound 54 (1.50 g, 4.72 mmol), compound 6 (1.54 g, 4.72 mmol), DCC (1.17 g, 5.66 mmol), DMAP (0.06 g, 0.52 mmol).

The experimental procedure was as described for the preparation of compound 17. The product was purified by column chromatography [(i) dichloromethane, (ii) 1% ethanol/dichloromethane, (iii) 2% ethanol/dichloromethane] and recrystallised from ethanol to give a sticky, colourless solid.

Yield 1.34 g (50%); mesomorphic behaviour (° C.)K60.5 (S$_C$*58.7)S$_A$*68.1I.

| | |
|---|---|
| ¹H NMR (CDCl₃) δ | 0.90(6H, 2t), 1.40(3H, d), 1.60–1.95(22H, m), 4.35(2H, t), 4.60(1H, m), 7.05(1H, d), 7.30(2H, d), 7.65(2H, d), 7.70(2H, d), 8.10(2H, d), 8.35(1H, dd), 8.45(1H, d); |
| IR (KBr) $v_{max}/cm^{-1}$ | 1730, 1710, 1240; |
| MS (m/z) | 626[M⁺], 584, 454, 326, 146; |
| OR | $[\alpha]_D^{18°}$ −22.4° (c = 0.01, CHCl₃). |

4-Cyano-4'-decyloxybiphenyl (57)

A mixture of 4-cyano-4'-hydroxybiphenyl (56) (10.10 g, 0.052 mol), 1-bromodecane (14.38 g, 0.065 mol), anhydrous potassium carbonate (37.32 g, 0.27 mol), butanone (300 ml) and a trace of potassium iodide was heated under reflux overnight. The cooled solution was filtered to remove inorganic salts and the solvent was removed in vacuo. The residual oil was distilled (to remove excess bromide) and finally purified by column chromatography (dichloromethane) to yield a colourless, low melting solid.

Yield 17.00 g(98%);mesomorphic behaviour(° C.) K42.3N50.8I(lit.K44N51.5I).

| | |
|---|---|
| ¹H NMR (CDCl₃) δ | 0.90(3H, t), 1.15–1.60(14H, m), 1.80(2H, m), 4.00(2H, t), 7.00(2H, d), 7.50(2H, d), 7.60(2H, d), 7.70(2H, d); |
| IR (KBr) $v_{max}/cm^{-1}$ | 2215,1255; |
| MS (m/z) | 335 [M⁺], 195, 69. |

4'-Decyloxy-4-biphenylcarboxylic acid (58)

Quantities: compound 57 (17.00 g, 0.051 mol), concentrated sulphuric acid (40 ml), water (40 ml), glacial acetic acid (200 ml).

The experimental procedure was as described for the preparation of compound 26 to yield a colourless, crystalline solid.

Yield 16.06 (89%); mesomorphic behaviour (° C.)K171S$_C$N253.5I(lit.K172.5S$_C$256.5N257I).

| | |
|---|---|
| ¹H NMR (CDCl₃ + DMSO) δ | 0.85(3H, t), 1.15–1.55(14H, m), 1.80(2H, m)1 4.00(2H, t), 6.95(2H, d), 7.55(2H, d), 7.60(2H, d), 8.05(2H, d), no obvious OH absorption; |
| IR (KBr) $\nu_{max}$/cm$^{-1}$ | 3300–2400, 1680, 1255; |
| Ms (m/z) | 354[M⁺], 214, 197, 69. |

(S)-(+)-3-Cyano-4-(2-methylbutyloxy)phenyl 4'-decyloxy-4-biphenylcarboxylate (59)

Quantities: compound 49 (1.42 g, 6.13 mmol), compound 59 (2.00 g, 6.13 mmol), DCC (1.52 g, 7.36 mmol), DMAP (0.08 g, 0.67 mmol).

The experimental procedure was as described for the preparation of compound 17. The product was purified by column chromatography (20% petrol/dichloromethane) and recrystallised from ethanol to give a white solid.

Yield 1.00 g (30%); mesomorphic behaviour (° C.) K94.2S$_C$*112.7S$_A$*168.7I.

| | |
|---|---|
| ¹H NMR (CDCl₃) δ | 0.90(3H, t), 1.00(3H, t), 1.10(3H, d), 1.15–2.05(19H, m), 3.90(2H, m), 4.00(2H, t), 7.00(1H, d), 7.00(2H, d), 7.40(1H, dd), 7.45(1H, d), 7.60(2H, d), 7.70(2H, d), 8.20(2H, d); |
| IR (KBr) $\nu_{max}$/cm$^{-1}$ | 2215, 1730, 1265; |
| MS (m/z) | 541[M⁺], 337, 197, 55; |
| OR | [α]$_D$ $^{25°}$ +2.9° (c = 0.01, CHCl₃). |

(R)-(−)-3-Cyano-4-(1-methylheptyloxy)phenyl 4'-decyloxy-4-biphenylcarboxylate (60)

Quantities: compound 50 (1.50 g, 6.07 mmol), compound 58 (2.15 g, 6.07 mmol), DCC (1.50 g, 7.29 mmol), DMAP (0.08 g, 0.67 mmol), dichloromethane/THF (100 ml).

The experimental procedure was as described for the preparation of compound 17. The product was purified by column chromatography [(i) 30% petrol/dichloromethane, (ii) 40% petrol/dichloromethane] and recrystallised from ethanol to give a white solid.

Yield 0.90 g (25%); mesomorphic behaviour (° C.) K64.9S$_C$*100.2S$_A$*118.8I.

| | |
|---|---|
| ¹H NMR (CDCl₃) δ | 0.90(3H, t), 1.20–1.95(32H, m), 4.05(2H, t), 4.50(1H, m), 7.00(1H, d), 7.00(2H, d), 7.40(1H, dd), 7.45(1H, d), 7.60(2H, d), 7.70(2H, d), 8.20(2H, d); |
| IR (KBr) $\nu_{max}$/cm$^{-1}$ | 2220, 1730, 1280, 1255; |
| MS (m/z) | 583[M⁺], 197, 57; |
| OR | [α]$_D$ $^{25°}$ −16.7° (c = 0.02, CHCl₃). |

(S)-(+)-1-(2-Methylbutyloxy)-2-nitrobenzene (62)

Quantities: 2-nitrophenol (61) (5.00 g, 0.036 mol), (S)-(−)-2-methylbutan-1-ol (3.17 g, 0.036 mol), DEAD (6.27 g, 0.036 mol), triphenylphosphine (9.44 g, 0.036 mol).

The experimental procedure was as described for the preparaton of compound 5. The product was purified by column chromatography (10% petrol/dichloromethane) to give a pale yellow oil.

Yield 6.32 g (84%).

| | |
|---|---|
| ¹H NMR (CDCl₃) δ | 0.95(3H, t), 1.05(3H, d), 1.35(1H, m), 1.60(1H, m), 1.95(1H, m), 3.90(2H, m), 7.00(1H, t), 7.05(1H, dd), 7.50(1H, t), 7.80(1H, dd); |
| IR (neat) | 1520, 1350, 1255; |
| $\nu_{max}$/cm$^{-1}$ | |
| MS (m/z) | 209[M⁺], 139, 70, 55, 43; |
| OR | [α]$_D$ $^{21.5°}$ +2.7° (c = 0.04, CHCl₃). |

(S)-(+)-1-Bromo-4-(2-Methylbutyloxy)-3-nitrobenzene (63)

Method 1

Quantities: compound 62 (2.46 g, 0.012 mol), bromine (7.67 g, 0.048 mol), chloroform (100 ml).

The experimental procedure was as described for the preparation of compound 41. The product was purified by column chromatography (10% petrol/dichloromethane) to give a pale yellow oil.

Yield 1.75 g (51%).

| | |
|---|---|
| ¹H NMR (CDCl₃) δ | 0.90(3H, t), 1.00(3H, d), 1,30(1H, m), 1.55(1H, m), 1.90(1H, m), 3.90(2H, m), 6.95(1H, d), 7.60(1H, dd), 7.95(1H, d); |
| IR (neat) $\nu_{max}$/cm$^{-1}$ | 1525, 1350, 1255; |
| MS (m/z) | 289 [M⁺], 287[M⁺], 219, 217, 70, 63, 55; |
| OR | [α]$_D$ $^{26°}$ +4.7° (c = 0.04, CHCl₃). |

Method 2

Quantities: 4-bromo-2-nitrophenol (64) (5.00 g,0.023 mol), (S)-(−)-2-methylbutan-1-ol (2.03 g, 0.023 mol), DEAD (4.01 g, 0.023 mol), triphenylphosphine (6.03 g, 0.023 mol).

The experimental procedure was as described for the preparation of compound 5. The product was purified by column chromatography (10% petrol/dichloromethane) to give a pale yellow oil.

Yield 6.10 g (92%).

Spectra as for method 1.

(R)-(−)-1-(1-Methylheptyloxy)-2-nitrobenzene (65)

Quantities: 2-nitrophenol (61) (3.34 g, 0.024 mol), (S)-(+)-octan-2-ol (3.13 g, 0.024 mol), DEAD(4.01 g, 0.024 mol), triphenylphosphine (6.29 g, 0.024 mol).

The experimental procedure was as described for the preparation of compound 5. The product was purified by column chromatography (50% petrol/dichloromethane) to give a pale yellow oil.

Yield 4.59 g (76%).

| | |
|---|---|
| ¹H NMR (CDCl₃) δ | 0.85(3H, t), 1.35(3H, d), 1.15–1.80(10H, m), 4.50(1H, m), 6.90–7.00(2H, m), 7.70–7.80(2H, m); |
| IR (neat) $\nu_{max}$/cm$^{-1}$ | 1525, 1355, 1255; |
| MS (m/z) | 251[M⁺], 139, 111, 84, 69; |
| OR | [α]$_D$ $^{23°}$ −51.3° (c = 0.04, CHCl₃). |

(R)-(−)-1-Bromo-4-(1-Methylheptyloxy)-3-nitrobenzene (66)

Method 1

Quantities: compound 65 (6.25 g, 0.025 mol), bromine (11.99 g, 0.075 mol), chloroform (100 ml).

The experimental procedure was as described for the preparation of compound 41. The crude product was purified by column chromatography (20% petrol/dichloromethane) to give a pale yellow oil.

Yield 5.22 g(63%).

| | |
|---|---|
| $^1$H NMR (CDCl$_3$) δ | 0.90(3H, t), 1.40(3H, d), 1.20–1.55(8H, m), 1.60(1H, m), 1.75(1H, m), 4.45(1H, m), 6.95(1H, d), 7.60(1H, dd), 7.90(1H, d); |
| IR (neat) $v_{max}$/cm$^{-1}$ | 1525, 1350, 1280; |
| MS (m/z) | 331[M$^+$], 329[M$^+$], 219, 217, 112, 83, 70; |
| OR | [α]$_D$ $^{22°}$ –43.7° (c = 0.03, CHCl$_3$). |

Method 2

Quantities: 4-bromo-2-nitrophenol (64) (3.00 g,0.014 mol), (S)-(+)-octan-2-ol (1.79 g, 0.014 mol), DEAD (2.40 g, 0.014 mol), triphenylphosphine (3.61 g,0.014 mol).

The experimental procedure was as described for the preparation of compound 41 and purification was carried out by column chromatography (30% petrol/dichloromethane).

Yield 2.67 g (58%).

Spectra as for method 1.

4-Bromo-4'-decyloxybiphenyl (68)

Quantities: 4-bromo-4'-hydroxybiphenyl (67) (20.00 g, 0.08 mol), 1-bromodecane (22.12 g, 0.10 mol), anhydrous potassium carbonate (57.10 g, 0.413 mol), potassium iodide (trace), butanone (500 ml). The experimental procedure was as described for the preparation of compound 57. The cooled mixture of product and inorganic salts was filtered off and washed carefully with dilute hydrochloric acid to remove the potassium carbonate. The white product was then washed with water until acid-free and heated under reflux with a minimum volume of ethanol to remove traces of 1-bromodecane. The product was filtered off, washed with cold ethanol and dried in vacuo to yield colourless crystals.

Yield 29.00 g (93%); mp 117–119° C.

| | |
|---|---|
| $^1$H NMR (CDCl$_3$) δ | 0.90(3H, t), 1.15–1.55(14H, m), 1.80(2H, m), 4.00(2H, t), 6.95(2H, d), 7.40(2H, d), 7.50(2H, d), 7.55(2H, d); |
| IR (KBr) $v_{max}$/cm$^{-1}$ | 1255; |
| MS (m/z) | 390[M$^+$], 388 [M$^+$], 250, 248, 162, 138, 99, 83, 69. |

4'-Decyloxybiphenyl-4-ylboronic acid (69)

Method 1

Quantities: compound 68 (8.00 g, 0.021 mol), n-butyllithium (2.5 M, 9.2 ml, 0.023 mol), trimethyl borate (4.36 g, 0.042 mol), THF (800 ml).

The procedure was as described for the preparaton of compound 43 but the addition of the butyllithium was started when the solution was at –60° C. and cooled further, to –70° C., during the addition such that the bromide (68) remained in solution. The blue-white solid was filtered off and washed with water until acid-free and dried in vacuo.

Yield mp

| | |
|---|---|
| $^1$H NMR (CDCl$_3$ + DMSO) δ | 0.35(3H, t), 0.65–1.05(10H, m), 1.30(2H, m), 2.25(2H, s), 3.45(2H, t), 6.90(2H, d), 7.05(4H, 2d), 7.40(2H, d), no obvious OH absorption; |
| IR (KBr) $v_{max}$/cm$^{-1}$ | 3600–3100, 1255; |
| MS (m/z) | 354[M$^+$], 326, 310, 186, 170. |

Method 2

A stirred mixture of magnesium turnings (0.62 g, 0.026 mol), compound 68 (10.11 g, 0.026 mol) and dry THF (100 ml) was heated under reflux in an atmosphere of dry nitrogen. A few drops of 1,2-dibromoethane were added and the resultant mixture heated under reflux for 3 h. TLC analysis (dichloromethane) revealed a complete reaction. The Grignard reagent was cooled to 0° C. and trimethyl borate (5.34 g, 0.051 mol) in dry THF (20 ml) was added and the resultant mixture left to stir overnight. The mixture was acidified with dilute hydrochloric acid and left for a further 1 h. The solvent was removed in vacuo and the remaining aqueous mixture was filtered off. The blue-white solid was washed with water until acid-free and dried (P$_2$O$_5$) in vacuo.

Yield 8.77 g (95%).

Spectra as for method 1.

(R)-(–)-4"-Decyloxy-4-(1-methylheptyloxy)-3-cyanoterphenyl (70)

A vigorously stirred mixture of compound 42 (1.50 g, 4.84 mmol), compound 69 (2.05 g, 5.81 mmol), aqueous sodium carbonate (2 M, 20 ml), tetrakis (triphenylphosphine palladium(0) (0.28 g, 0.24 mmol) and dimethoxyethane (100 ml) was heated under reflux, overnight, in a dry nitrogen atmosphere. The cooled mixture was washed with a large volume of water, dried (MgSO$_4$) and filtered over hyflo filter aid. The solvent was evaporated in vacuo and the residue was purified by column chromatography (70% petrol/dichloromethane) and recrystallised from ethanol to give white crystals.

Yield 1.20 g (46%); mesomorphic behaviour (° C.)K65.3 (S$_C$*60.0) S$_A$*100.1 I).

| | |
|---|---|
| $^1$H NMR (CDCl$_3$) δ | 0.90(6H, 2t), 1.20–1.60(23H, m), 1.40(3H, d), 1.75–1.95(3H, m), 4.00(2H, t), 4.50(1H, m), 7.00(2H, d), 7.05(1H, d), 7.55(4H, 2d), 7.65(2H, d), 7.75(1H, dd), 7.80(1H, d); |
| IR (KBr) $v_{max}$/cm$^{-1}$ | 2215, 1260, 1250; |
| MS (m/z) | 539[M$^+$], 447, 427, 287, 71; |
| OR | [α]$_D$ $^{27°}$ –16.2° (c = 0.03, CHCl$_3$). |

(S)-(+)-4"-Decyloxy-4-(2-methylbutyloxy)-3-nitroterphenyl (71)

Quantities: compound 63 (1.50 g, 5.21 mmol), compound 69 (2.21 g, 6.25 mmol), aqueous sodium carbonate (2 M, 20 ml), tetrakis (triphenylphosphine)palladium(0) (0.30 g, 0.26 mmol), dimethoxyethane (100 ml).

The experimental procedure was as described for the preparation of compound 70. The product was purified by column chromatography [(i) 50% petrol/dichloromethane; (ii) 80% petrol/dichloromethane)] and recrystallised from ethanol to yield a pale yellow solid.

Yield 1.14 g (42%); mesomorphic behaviour (° C.)K71.8S$_A$*153.8 I.

| | |
|---|---|
| $^1$H NMR (CDCl$_3$) δ | 0.90(3H, t), 1.00(3H, t), 1.10(3H, d), 1.15–2.05(19H, m), 3.95(2H, m), 4.00(2H, t), 7.00(2H, d), 7.15(1H, d), 7.55(2H, d), 7.60(2H, d), 7.65(2H, d), 7.75(1H, dd), 8.10(1H, d); |
| IR (KBr) $v_{max}$/cm$^{-1}$ | 1540, 1340, 1280, 1250; |
| MS (m/z) | 517[M$^+$], 447, 307, 261, 71, 55; |
| OR | [α]$_D$ $^{20°}$ +2.4° (c = 0.01, CHCl$_3$). |

(R)-(–)-4"-Decyloxy-4-(1-methylheptyloxy)-3-nitroterphenyl (72)

Quantities: compound 66 (1.50 g, 4.55 mmol), compound 69 (1.93 g, 5.46 mmol), sodium carbonate (2 M, 20 ml), tetrakis (triphenylphosphine) palladium(0) (0.27 g, 0.23 mmol), dimethoxyethane (100 ml).

The experimental procedure was as described for the preparation of compound 70. The crude product was purified by column chromatography (70% petrol/dichloromethane) and recrystallised from ethanol to give a bright yellow solid.

Yield 0.78 g (31%); mesomorphic behaviour (° C.)K46.7S$_C$*53.5S$_A$*96.0 I.

| $^1$H NMR (CDCl$_3$) δ | 0.90(6H, 2t), 1.40(3H, d), 1.20–1.90(26H, m), 4.00(2H, t), 4.55(1H, m), 7.00(2H, d), 7.15(1H, d), 7.55(2H, d), 7.60(2H, d), 7.65(2H, d), 7.75(1H, dd), 8.05(1H, d); |
|---|---|
| IR (KBr) vmax/cm$^{-1}$ | 1535, 1360, 1250; |
| MS (m/z) | 559[M$^+$], 447, 307, 121, 71; |
| OR | [α]$_D$ $^{21°}$ −4.2° (c = 0.03, CHCl$_3$). |

1-(4'-Decyloxybiphenyl-4-yl)-2-(1-hydroxy-1-methylethyl) ethyne (73)

A stirred mixture of compound 68 (15.00 g, 0.039 mol), 2-methylbut-3-yn-2-ol (7.15 g, 0.085 mol), copper(I) iodide (0.34 g, 1.80 mmol), tetrakis (triphenylphosphine) palladium(0) (2.89 g, 2.50 mmol) and diisopropylamine (150 ml) was heated under reflux in a dry nitrogen atmosphere for 24 h. The resultant mass was dissolved in THF and filtered over hyflo filter aid to remove inorganic materials. Volatile materials were removed in vacuo and the brown solid was recrystallised from ethanol to give a white, fluffy solid.

Yield 12.92 g (85%); mp 126–127° C.

| $^1$H NMR (CDCl$_3$) δ | 0.90(3H, t), 1.20–1.60(14H, m), 1.60(6H, 2s), 1.80(2H, m), 2.00(1H, s), 4.00(2H, t), 6.95(2H, d), 7.45(2H , d), 7.50(4H, 2d); |
|---|---|
| IR (KBr) v$_{max}$/cm$^{-1}$ | 3700–3100, 1255; |
| MS (m/z) | 392[M$^+$], 377, 252, 237. |

4'-Decyloxybiphenyl-4-ylethyne (74)

Compound 73 (12.90 g, 0.033 mol) and sodium hydroxide ( ) was boiled for 1 h in toluene (100 ml) under a dry nitrogen atmosphere and the resultant toluene/acetone mixture removed in a Dean-Stark apparatus. As the toluene mixture was removed fresh toluene was added to the reaction mixture. TLC analysis (dichloromethane) revealed a complete reaction. The sodium hydroxide was filtered off and the toluene washed with water, dried (MgSO$_4$) and removed in vacuo to leave a metallic-beige solid.

Yield 10.74 g (97%); mp 82–84° C.

| 1H NMR (CDCl$_3$) δ | 0.90(3H, t), 1.20–1.55(14H, m), 1.80(2H, m), 3.10(1H, s), 4.00(2H, t), 6.95(2H, d), 7.50(6H, 3d); |
|---|---|
| IR (KBr) v$_{max}$/cm$^{-1}$ | 3290, 1255; |
| MS (m/z) | 334[M$^+$], 194, 165. |

(S)-(+)-1-[3-Cyano-4-(2-methylbutyloxy)phenyl]-2-(4'-decyloxybiphenyl-4-yl) ethyne (75)

Quantities: compound 41 (2.00 g, 7.46 mmol), compound 74 (2.99 g, 8.95 mmol), copper(I) iodide (0.29 g, 1.53 mmol), tetrakis (triphenylphosphine) palladium(0) (0.43 g, 0.37 mmol), triethylamine (100 ml).

The experimental procedure was as described for the preparation of compound 73. The crude product was purified by column chromatography, [(i) 20% petrol/dichloromethane, (ii) 40% petrol/dichloromethane] and recrystallised from ethanol to give a white solid.

Yield 0.80 g (21%); mesomorphic behaviour (° C.) K 63.5 S$_C$* 104.1 S$_A$* 152.6 L.

| $^1$H NMR (CDCl$_3$) δ | 0.90(3H, t), 1.00(3H, t), 1.10(3H, d), 1.20–1.70(16H, m), 1.75–2.05(3H, m), 3.90(2H, m), 4.00(2H, t), 6.95(1H, d). 7.00(2H, d), 7.55(6H, 3d), 7.65(1H, dd), 7.75(1H, d),; |
|---|---|
| IR (KBr) v$_{max}$/cm$^{-1}$ | 2215, 1255; |
| MS (m/z) | 521[M$^+$], 451, 427, 311, 57, 43; |
| OR | [α]$_D$ $^{24°}$ +12.8° (c = 0.01, CHCl$_3$). |

(R)-(−)-1-[3-Cyano-4-(1-methylheptyloxy)phenyl]-2-(4'-decyloxybiphenyl-4-yl) ethyne (76)

Quantities: compound 42 (2.00 g, 6.45 mmol), compound 74 (2.59 g, 7.74 mmol), copper (I) iodide (0.12 g, 0.65 mmol), tetrakis(triphenylphosphine)palladium(0) (1.49 g, 1.29 mmol), triphenylphosphine (60 ml).

The experimental procedure was as described for the preparation of compound 73. The crude product was purified by column chromatography (50% petrol/dichloromethane) and recrystallised from ethanol to give a pale-yellow solid.

Yield 1.44 g (40%); mesomorphic behaviour (° C.) K 60.3 S$_A$* 105.6 L.

| $^1$H NMR (CDCl$_3$) δ | 0.90(3H, t), 1.35(3H, d), 1.20–1.55(26H , m), 1.55(1H, m), 1.80(2H, m), 4.00(2H, t), 4.50(1H, m), 6.95(1H, d), 7.00(2H, d), 7.55(6H, 3d), 7.65(1H, dd), 7.75(1H, d); |
|---|---|
| IR (KBr) v$_{max}$/cm$^{-1}$ | 2260, 1270; |
| MS (m/z) | 563[M$^+$], 451, 427, 311, 71; |
| OR | [α]$_D$ $^{28°}$ −11.4 (c = 0.02, CHCl$_3$). |

(S)-(+)-1-[4-(2-Methylbutyloxy)-3-nitrophenyl]-2-(4'-decyloxybiphenyl-4-yl) ethyne (77)

Quantities: compound 63 (2 g, 6.94 mmol), compound 74 (2.78 g, 8.32 mmol), copper(I) iodide (0.26 g, 1.37 mmol), tetrakis(triphenylphosphine)palladium(0) (0.40 g, 0.35 mmol), triethylamine (100 ml).

The experimental procedure was as described for the preparation of compound 73. The crude material was purified by column chromatography [(i) 70% petrol/dichloromethane, (ii) 50% petrol/dichloromethane] and recrystallised from ethanol and ethyl acetate to give a yellow, crystalline solid.

Yield 0.75 g (20%); mesomorphic behaviour (° C.) K 60.0 S$_C$* 90.1 S$_A$* 144.2 L.

| $^1$H NMR (CDCl$_3$) δ | 0.85(3H, t), 0.95(3H, t), 1.05(3H, d), 120–1.70(16H, m), 1.80(2H, m), 1.95(1H, m), 3.95(2H, m), 4.00(2H, t), 6.95(2H, d), 7.05(1H, d), 7.55(6H, 3d), 7.65(1H, dd), 8.00(1H, d); |
|---|---|
| IR (KBr) v$_{max}$/cm$^{-1}$ | 1535, 1350, 1265; |
| MS (m/z) | 541[M$^+$], 471, 331, 71, 55; |
| OR | [α]$_D$ $^{28.5°}$ +4.2 (c = 0.02, CHCl$_3$). |

(R)-(−)-1-[4-(1-Methylheptyloxy)-3-nitrophenyl]-2-(4'-decyloxybiphenyl-4-yl) ethyne (78)

Quantities: compound 66 (2.00 g, 6.06 mmol), compound 74 (2.43 g, 7.27 mmol), tetrakis(triphenylphosphine) palladium(0) (0.35 g, 0.30 mmol), copper(I) iodide (0.23 g, 1.21 mmol), triethylamine (100 ml).

The experimental procedure was as described for the preparation of compound 73. The crude product was purified by column chromatography [(i) 80% petrol/dichloromethane (twice), (ii) 60% petrol/dichloromethane, (iii) 80% petrol/dichloromethane] and recrystallised from ethanol to give yellow crystals.

Yield 0.90 g (24%); mesomorphic behaviour (° C.) K 77.8 S$_A$* 99.6 I.

| | |
|---|---|
| 1H NMR (CDCl$_3$) δ | 0.90(6H, 2t), 1.15–1.55(23H, m), 1.40(3H, d), 1.55–1.75(1H, m), 1.75–1.90(2H, m), 4.00(2H, t), 4.55(1H, m), 7.00(2H, d), 7.05(1H, d), 7.55(6H, 3d), 7.65(1H, dd), 7.95(1H, d); |
| IR (KBr) v$_{max}$/cm$^{-1}$ | 1535, 1360, 1250; |
| Ms (m/z) | 583[M$^+$], 471, 331, 71; |
| OR | [α]$_D$$^{22°}$ −1.2° (c = 0.01, CHCl$_3$). |

2,3-dimethoxy-6-nitrophenol (80)

2,3-Dimethoxyphenol (79) (5.00 g, 0.032 mol) was dissolved in glacial acetic acid (50 ml) and the resultant, stirred solution was cooled to 5° C. A cooled (5° C.) mixture of concentrated nitric acid (10 ml) and water (10 ml) was added in one portion to the phenol solution which immediately turned dark red-brown. The mixture was stirred for a further minute and poured into water (200 ml), this solution was neutralised with saturated sodium bicarbonate solution until all effervescense had ceased. The resultant yellow solution was extracted with several portions of diethyl ether until the ether remained almost colourless. The combined extracts were washed with water until the water remained almost colourless, dried (MgSO$_4$) and the ether evaporated off in vacuo to leave a brown oil. This was purified by column chromatography (10% petrol/dichloromethane) to give a bright yellow solid.

Yield 2.50 g (66%); mp 94–97° C.

| | |
|---|---|
| $^1$H NMR (CDCl$_3$) δ | 3.95(3H, s), 4.00(3H, s), 6.60(1H, d), 7.95(1H, d), no obvious OH absorption; |
| IR (KBr) v$_{max}$/cm$^{-1}$ | 3700–3000, 1530, 1360, 1240; |
| MS (m/z) | 199[M$^+$], 182, 139, 109, 95, 80. |

(R)-(−)-1,2-Dimethoxy-3-(1-methylheptyloxy)-4-nitrobenzene (81)

Quantities: compound 80 (1.39 g, 6.98 mmol), (S)-(+)-octan-2-ol (0.91 g, 6.98 mmol), DEAD (1.22 g, 6.98 mmol), triphenylphosphine (1.83 g, 6.98 mmol).

The experimental procedure was as described for the preparation of compound 5. The crude product was purified by column chromatography (10% petrol/dichloromethane) to give a pale yellow oil.

Yield 1.99 g (92%).

| | |
|---|---|
| $^1$H NMR (CDCl$_3$) δ | 0.85(3H, t), 1.15–1.50(11H, m), 1.25(3H, d), 1.50–1.70(1H, m), 1.70–1.85(1H, m), 3.85(3H, s), 3.95(3H, s), 4.50(1H, m), 6.70(2H, d), 7.65(2H, d); |
| IR (neat) v$_{max}$/cm$^{-1}$ | 1520, 1345, 1290; |
| MS (m/z) | 311[M$^+$], 199, 182, 43; |
| OR | [α]$_D$$^{25°}$ +34.1° (c = 0.01, CHCl$_3$). |

4-Bromo-2,3-dimethoxy-6-nitrophenol (82)

Quantities: compound 80 (1.00 g, 5.03 mmol), bromine (0.80 g, 5.03 mmol), chloroform (20 ml).

The experimental procedure was as described for the preparation of compound 41 except only one portion of bromine was used. The crude, oily product was purified by column chromatography (10% petrol/dichloromethane) to give a bright yellow solid.

Yield 1.49 g (100 %); mp 77–80° C.

| | |
|---|---|
| $^1$H NMR (CDCl$_3$) δ | 3.95(3H, s), 4.10(3H, s), 8.15(1H, s), 10.8(1H, s); |
| IR (KBr) v$_{max}$/cm$^{-1}$ | 1525, 1330; |
| MS (m/z) | 279[M$^+$], 277[M$^+$], 262, 260, 219, 217, 53. |

(R)-(−)-1-Bromo-2,3-dimethoxy-4-(1-methylheptyloxy)-5-nitrobenzene (83)

Quantities: compound 82 (2.00 g, 7.19 mmol), (S)-(+)-octan-2-ol (0.94 g, 7.19 mmol), DEAD (1.25 g, 7.19 mmol), triphenylphosphine (1.89 g, 7.19 mmol).

The experimental procedure was as described for the preparation of compound 5. Purification by column chromatography (10% petrol/dichloromethane) gave a pale yellow oil.

Yield 2.74 g (98%).

| | |
|---|---|
| $^1$H NMR (CDCl$_3$) δ | 0.90(3H, t), 1.25(3H, d), 1.10–1.50(8H, m), 1.50–1.85(2H, 2m), 3.90(3H, s), 4.00(3H, s), 4.50(1H, m), 7.80(1H, s); |
| IR (neat) v$_{max}$/cm$^{-1}$ | 1535, 1350, 1265; |
| MS (m/z) | 391[M$^+$], 389[M$^+$], 279, 277, 261, 259; |
| OR | [α]$_D$$^{22°}$ +6.9° (c = 0.05, CHCl$_3$). |

(R)-(−)-4″-Decyloxy-2,3-dimethoxy-4-(1-methylheptyloxy)-5-nitroterphenyl (84)

Quantities: compound 83 (1.50 g, 3.85 mmol), compound 69 (2.20 g, 6.21 mmol), aqueous sodium carbonate (2 M, 20 ml), tetrakis(triphenylphosphine)palladium(0) (0.30 g, 0.26 mmol), dimethoxyethane (100 ml).

The experimental procedure was as described for the preparation of compound 70. Purification was by column chromatography (50% petrol/dichloromethane) and recrystallisation from ethanol and ethyl acetate to give a pale yellow powder.

Yield 0.5 g (21%); mp 39–40° C.

| | |
|---|---|
| $^1$H NMR (CDCl$_3$) δ | 0.90(6H, 2t), 1.15–1.90(29H, m), 3.80(3H, s), 3.95(3H, s), 4.00(2H, t), 4.55(1H, m), 7.00(2H, d), 7.50–7.65(6H, 3d), 7.65(1H, s); |
| IR (KBr) v$_{max}$/cm$^{-1}$ | 1520, 1340, 1255; |
| MS (m/z) | 619[M$^+$], 507, 367, 71; |
| OR | [α]$_D$$^{25°}$ +13.2° (c = 0.01, CHCl$_3$). |

1-Bromo-4-decyloxybenzene (86)

Quantities: 4-bromophenol 85 (10.00 g, 0.058 mol), 1-bromooctane (15.98 g, 0.072 mol), anhydrous potassium carbonate (39.94 g, 0.289 mol), potassium iodide (trace), butanone (250 ml).

The experimental procedure was as described for the preparation of compound 57. The crude product was distilled in vacuo (0.01 mmHg) to remove excess 1-bromooctane and purified by column chromatography (50% petrol/dichloromethane) to yield a colourless oil.

Yield 13.59 g (75%).

| | |
|---|---|
| $^1$H NMR (CDCl$_3$) δ | 0.90(3H, t), 1.20–1.55(14H, m), 1.75(2H, m), 3.90(2H, t), 6.75(2H, d), 7.35(2H, d); |

-continued

| | |
|---|---|
| IR (neat) $v_{max}/cm^{-1}$ | 1240; |
| MS (m/z) | 314[M⁺], 312[M⁺]. |

4-Decyloxyphenylboronic acid (87)

Quantities: compound 86 (10.00 g, 0.032 mol), n-butyllithium (2.5 M, 15.3 ml, 0.038 mol), trimethyl borate (6.64 g, 0.064 mol).

The experimental procedure was as described for the preparation of compound 47 to give a white solid.

Yield 7.68 g (86%); mp 61–63° C.

| | |
|---|---|
| $^1$H NMR (CDCl$_3$) δ | 0.85(3H, t), 1.15–1.50(14H, m), 1.70(2H, m), 3.95(2H, t), 6.85(2H, d), 7.70(2H, d), 7.80(2H, s); |
| IR (KBr) $v_{max}/cm^{-1}$ | 3700–3100, 1250; |
| MS (m/z) | 278[M⁺], 110, 94. |

(R)-(−)-3-Cyano-4'-Decyloxy-4-(1-methylheptyloxy) biphenyl (88)

Quantities: compound 42 (1.50 g, 4.84 mmol), compound 87 (1.61 g, 5.81 mmol), aqueous sodium carbonate (2 M, 20 ml), tetrakis(triphenylphosphine)palladium(0) (0.28 g, 0.24 mmol), 1,2-dimethoxyethane (100 ml).

The experimental procedure was as described for the preparation of compound 70. The crude product was purified by column chromatography (40% petrol/dichloromethane) to give a viscous, colourless oil which was heated (150° C.) in vacuo (0.01 mmHg) until no more starting material distilled off.

Yield 0.86 g (50%).

| | |
|---|---|
| $^1$H NMR (CDCl$_3$) δ | 0.90(6H, 2t), 1.35(3H, d), 1.15–1.95(26H, m), 4.00(2H, t), 4.50(1H, m), 6.85(1H, d), 6.95(2H, d), 7.40(2H, d), 7.60(1H, dd), 7.70(1H, d); |
| IR (neat) $v_{max}/cm^{-1}$ | 2215, 1245; |
| MS (m/z) | 463[M⁺], 351, 211, 71; |
| OR | $[\alpha]_D^{22°}$ −24.4° (c = 0.05, CHCl$_3$). |

(R)-(−)-4'-Decyloxy-4-(1-methylheptyloxy)-3-nitrobiphenyl (89)

Quantities: compound 66 (1.50 g, 4.55 mmol), compound 87 (1.52 g, 5.45 mmol), aqueous sodium carbonate (2 M, 20 ml), tetrakis(triphenylphosphine)palladium(0) (0.26 g, 0.23 mmol), dimethoxyethane (100 ml).

The experimental procedure was as described for the preparation of compound 70. The crude product was purified by column chromatography (50% petrol/dichloromethane) to give a viscous, yellow oil which was heated (150° C.) in vacuo (0.01 mmHg) to remove any excess starting material.

Yield 1.12 g (51%).

| | |
|---|---|
| $^1$H NMR (CDCl3) δ | 0.90(6H, 2t), 1.40(3H, d), 1.20–1.90(26H, m), 4.00(2H, t), 4.50(1H, m), 6.95(2H, d), 7.10(1H, d), 7.45(2H, d), 7.65(1H, dd), 7.95(1H, d); |
| IR (neat) $v_{max}/cm^{-1}$ | 1530, 1350, 1260, 1240; |
| MS (m/z) | 483[M⁺], 372, 231, 71, 5; |
| OR | $[\alpha]_D^{22°}$ −9.1° (c = 0.03, CHCl$_3$). |

(R)-(−)-Octyl 4-[4-(1-methylheptyloxy)-3-nitrobenzoyloxy]benzoate (90)

Quantities: compound 16 (1.68 g, 5.69 mmol), compound 23 (1.42 g, 5.69 mmol), DCC (1.41 g, 6.83 mmol), DMAP (0.08 g, 0.63 mmol), dichloromethane (50 ml).

The experimental procedure was as described for the preparation of compound 17. The crude product was purified by column chromatography (50% petrol/dichloromethane) to give a pale yellow oil which was heated (150° C.) in vacuo (0.01 mmHg) to remove any starting material.

Yield 1.50 g (50%).

| | |
|---|---|
| $^1$H NMR (CDCl) δ | 0.90(6H, 2t), 1.15–1.95(22H, m), 1.40(3H, d), 4.35(2H, t), 4.65(1H, m), 7.15(1H, d), 7.30(2H, d), 8.15(2H, d), 8.30(1H, dd), 8.60(1H, d); |
| IR (neat) $v_{max}/cm^{-1}$ | 1740, 1715, 1530, 1355, 1235; |
| MS (m/z) | 527[M⁺], 277, 167; |
| OR | $[\alpha]_D^{21°}$ −6.4° (c = 0.02, CHCl$_3$). |

(R)-(−)-Decyl 4-[4-(1-methylheptyloxy)-3-nitrobenzoyloxy]benzoate (91)

Quantities: compound 16 (1.59 g, 5.41 mmol), compound 24 (1.50 g, 5.41 mmol), DCC (1.34 g, 6.49 mmol), DMAP (0.07 g, 0.59 mmol), dichloromethane (50 ml).

The experimental procedure was as described for the preparation of compound 17 and purified as described for compound 90 to give a viscous, pale yellow oil.

Yield 1.68 g (56%).

| | |
|---|---|
| $^1$H NMR (CDCl) δ | 0.90(6H, 2t), 1.45(3H, d), 1.15–1.95(26H, m), 4.35(2H, t), 4.65(1H, m), 7.15(1H, d), 7.30(2H, d), 8.15(2H, d), 8.30(1H, dd), 8.60(1H, d); |
| IR (neat) $v_{max}/cm^{-1}$ | 1740, 1715, 1530, 1355, 1235; |
| MS (m/z) | 555[M⁺], 278, 166, 120, 57, 43; |
| OR | $[\alpha]_D^{22.5°}$ −7.8° (c = 0.02, CHCl$_3$). |

Ethyl 3-nitro-4-octyloxybenzoate (92)

Quantities: Ethyl 4-hydroxy-3-nitrobenzoate (10) (5.00 g, 0.037 mmol), 1-bromooctane (14.39 g, 0.075 mol), anhydrous potassium carbonate (15.45 g, 0.118 mol) potassium iodide (trace), butanone (200 ml).

The experimental procedure was as described for the preparation of compound 57. The crude product was purified by column chromatography (50% petrol/dichloromethane) to yield a pale yellow oil.

Yield 7.30 g (61%).

| | |
|---|---|
| $^1$H NMR (CDCl$_3$) δ | 0.90(6H, 2t), 1.15–1.55(10H, m), 1.80–1.95(2H, m), 4.15(2H, t), 4.40(2H, q), 7.10(1H,d), 8.20(1H, dd), 8.50(1H, d); |
| IR (neat) $v_{max}/cm^{-1}$ | 1720, 1530, 1360, 1240; |
| MS (m/z) | 323[M⁺], 278, 212, 183, 166, 112. |

3-Nitro-4-octyloxybenzoic acid (93)

Quantities: compound 92 (3.50 g, 0.011 mol), sodium hydroxide (0.88 g, 0.022 mol), ethanol (80 ml), water (20 ml).

The experimental procedure was as described for the preparation of compound 9. During the reaction the solution changed colour from yellow to orange, on acidification a pale yellow solid was formed which was recrystallised from ethanol to give yellow crystals.

Yield 2.04 g (63%); mp 98–100° C.

| | |
|---|---|
| $^1$H NMR (CDCl$_3$) δ | 0.90(3H, t), 1.15–1.55(10H, m), 1.85(2H, m), 4.20(2H, t), 7.15(1H, d), 8.25(1H, dd), 8.55(1H, d), no obvious OH absorption; |
| IR (KBr) ν$_{max}$/cm$^{-1}$ | 3400–2400, 1695, 1530, 1350, 1250, 915, 830, 765; |
| MD (m/z) | 295[M$^+$], 183, 112, 83, 70. |

Octyl 4'-(4-octyloxy-3-nitrobenzoyloxy)-4-biphenylcarboxylate (94)

Quantities: compound 93 (1.60 g, 5.42 mmol), compound 6 (1.77 g, 5.42 mmol), DCC (1.34 g, 6.50 mmol), DMAP (0.07 g, 0.60 mmol).

The experimental procedure was as described for the preparation of compound 17. The crude product was purified by column chromatography (10% petrol/dichloromethane) and recrystallised from ethanol and ethyl acetate to give a pale yellow solid.

Yield 1.72 g (53%); mesomorphic behaviours (° C.) K 54.2 S$_C$ 122.2 S$_A$ 158.2 L.

| | |
|---|---|
| $^1$H NMR (CDCl$_3$) δ | 0.90(6H, 2t), 1.20–1.60(20H, m), 1.70–1.95(4H, 2m), 4.20(2H, t), 4.35(2H, t), 7.20(1H, d), 7.30(2H, d), 7.65(4H, 2d), 8.10(2H, d), 8.35(1H, dd), 8.70(1H, d); |
| IR (KBr) ν$_{max}$/cm$^{-1}$ | 1735, 1690, 1540, 1360, 1240; |
| MS (m/z) | 603[M$^+$], 278, 166. |

Figure 19A:
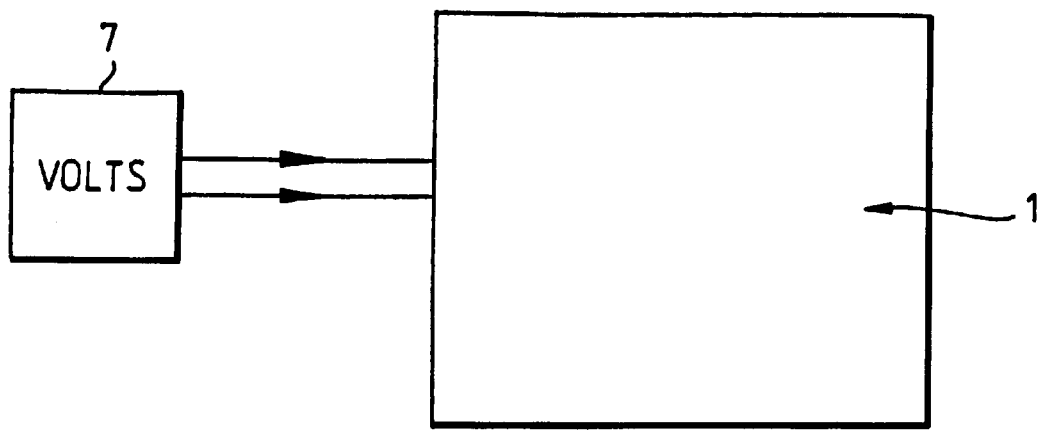
FIGS. 19A and 19B illustrate front and sectional views respectively of a reflective spatial light modulator drawn to different scales, in which the materials of the current invention may be incorporated.
Figure 19B:
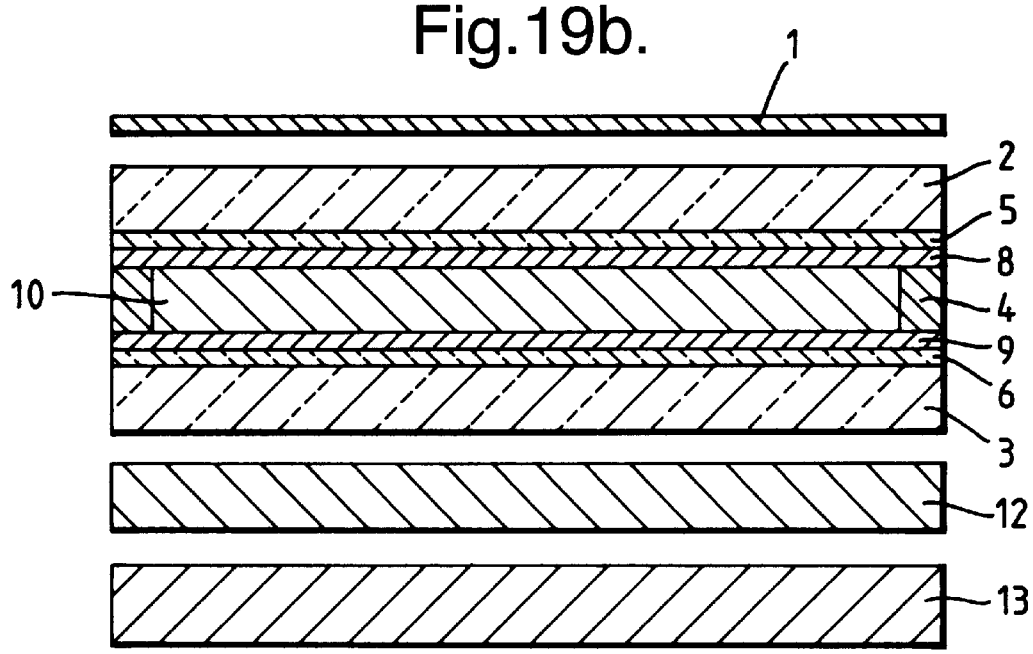

As shown in FIGS. 19A and 19B a spatial light modulator comprises a liquid crystal cell 1 formed by typically two glass walls 2, 3 and a 0.1–10 μm eg 2.5 μm thick spacer 4. The inner faces of the walls carry thin transparent indium tin oxide electrodes 5, 6 connected to a variable voltage source 7. On top of the electrodes 5, 6 are surface alignment layers 8, 9 eg of rubbed polyimide described in more detail later. Other alignment techniques are also suitable eg non-rubbing techniques such as evaporation of SiO$_2$. A layer 10 of liquid crystal material is contained between the walls 2, 3 and spacer 4. In front of the cell 1 is a linear polariser 11; behind the cell 1 is a quarter plate 12 (this may be optional) and a mirror 13. An example of a linear polariser is a polarising beam splitter (not illustrated here).

The alignment layer 8,9 have two functions one to align contacting liquid crystals molecules in a preferred direction and the other to give a tilt to these molecules—a so called surface tilt—of a few degrees typically around 4° or 5°. The alignment layers 8, 9 may be formed by placing a few drops of the polyimide onto the cell wall and spinning the wall unit a uniform thickness is obtained. The polyimide is then cured by heating to a predetermined temperature for a predetermined time followed by unidirectional rubbing with a roller coated with a cloth, eg a nylon cloth.

There are a variety of electroclinic devices in which the compounds of the present invention may be incorporated. For example in the above description of FIGS. 19A and 19B, active back plane driving may be utilised. One of the walls forming the cell may be formed from a silicon substrate eg a wafer which possesses circuitry, which may or may not contain mirrored electrodes, for driving pixels.

For many of these devices there exists an optimum thickness for the cell which is related to the birefringence (Δn) given by:

$$d = \frac{(2m+1)}{4(\Delta n)} \lambda \text{ for a reflective device}$$

$$d = \frac{(2m+1)}{2} \frac{\lambda}{(\Delta n)} \text{ for a transmissive device}$$

wherein:
λ=wavelength of operation
Δn=birefringence of liquid crystalline material
m=integer.

Small arrays of pixels may be driven by applying dc voltages to each individual pixel, where the applied voltage induces a relative tilt, thereby setting the grey level or phase modulation. It is desirable to maintain a substantially zero net dc so the inverse image can be applied for the same time period to neutralise charging effects.

Some suitable methods for driving electroclinic devices containing arrays of pixels described by the present invention may be found in UK patent application GB 2 247 972 A.

Suitable methods for driving electroclinic devices may benefit by including in such devices, materials which possess a high resistivity and a large optical response.

It may also be advantageous that the liquid crystal material possesses a high resistivity, one reason being in order to minimise leakage current through the pixel whilst the pixel is being addressed. Some addressing schemes which incorporate active backplanes rely on this charge storage to maintain their pre-determined level.

The mode of operation of the devices described by the current invention includes either amplitude modulation or phase modulation. Similarly, devices may be used in reflectance or transmissive mode.

The following compounds are example compounds that have been synthesised for the present invention. Inukai et al have described the synthesis of some of these type molecules in Ferroelectrics, 1988, vol. 85, 451–59.

In the synthetic experimental section, materials 1, 25, 56 and 67 were purchased from Merck Ltd. Poole and materials 7, 10, 19, 29, 34, 38, 51, 61, 64, 79 and 85 were purchased from Aldrich.

EXAMPLE 1

Compound 17

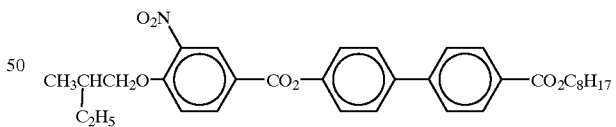

EXAMPLE 2

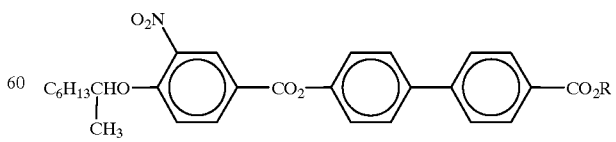

R = C$_8$H$_{17}$: Compound 18
R = C$_6$H$_{13}$: Compound 18a
R = C$_{10}$H$_{21}$: Compound 18b EXAMPLE 3
Compound 28
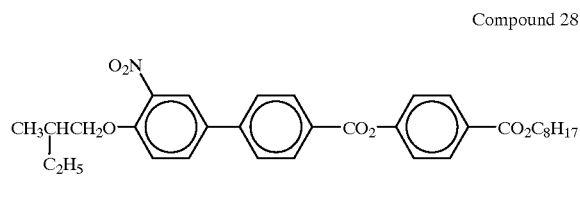
EXAMPLE 4
Compound 32
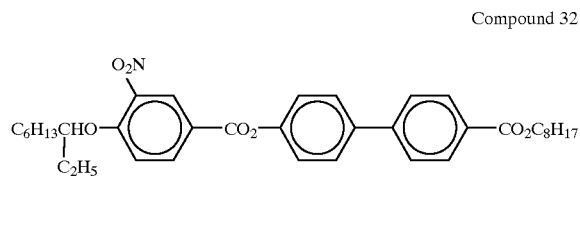
EXAMPLE 5
Compound 33
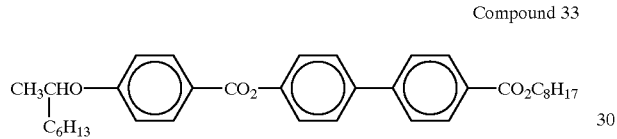
EXAMPLE 6
Compound 37
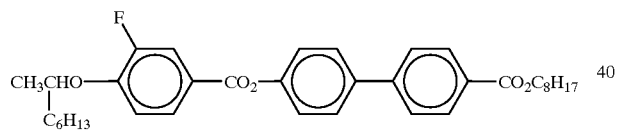
EXAMPLE 7
Compound 45
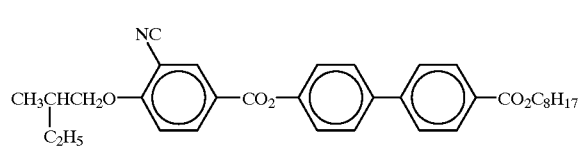
EXAMPLE 8
Compound 46
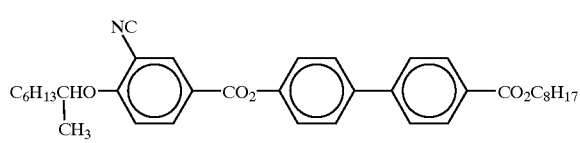
EXAMPLE 9
Compound 55
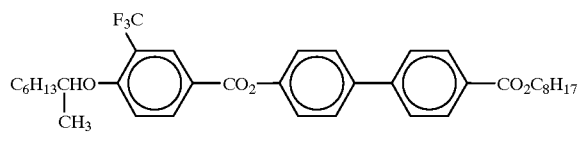
EXAMPLE 10
Compound 59
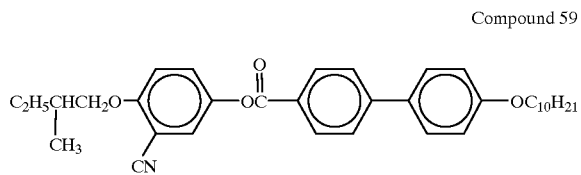
EXAMPLE 11
Compound 60
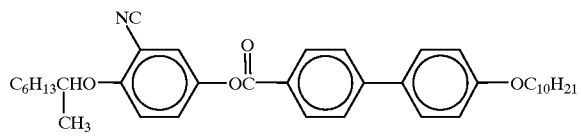
EXAMPLE 12
Compound 70
EXAMPLE 13
Compound 71
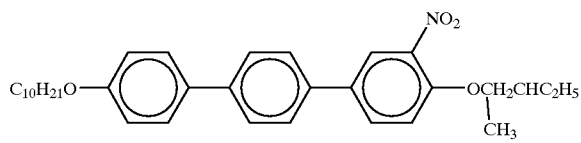

EXAMPLE 14
Compound 72
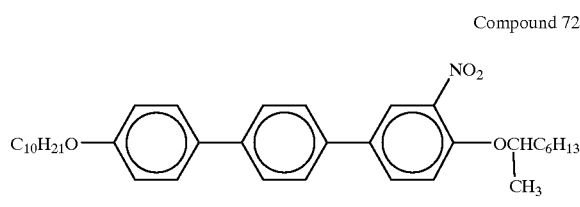
EXAMPLE 15
Compound 75
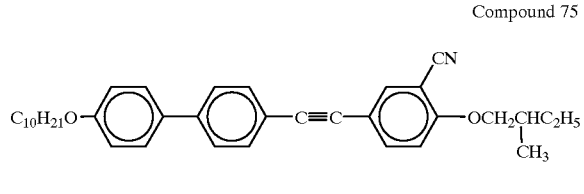
EXAMPLE 16
Compound 76
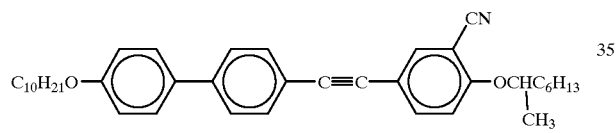
EXAMPLE 17
Compound 77
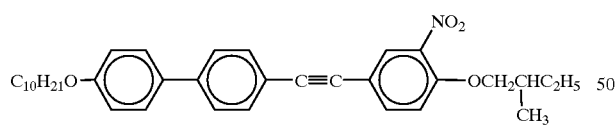
EXAMPLE 18
Compound 78
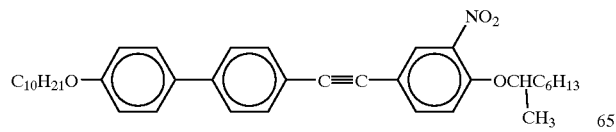
EXAMPLE 19
Compound 84
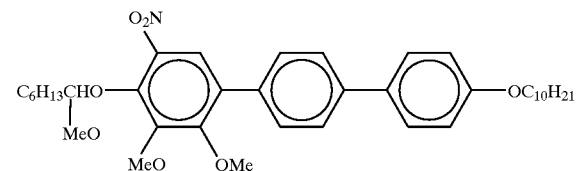
EXAMPLE 20
Compound 88
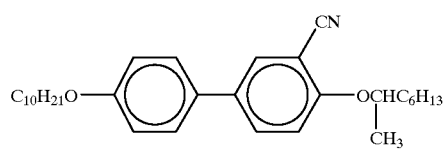
EXAMPLE 21
Compound 89
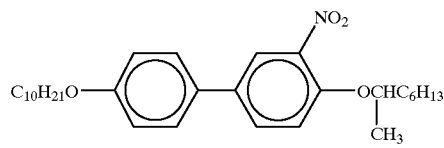
EXAMPLE 22
Compound 90
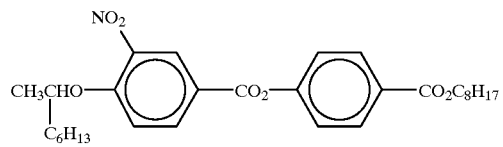
EXAMPLE 23
Compound 91
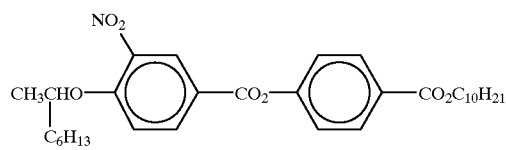

EXAMPLE 24

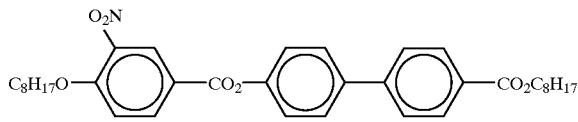
Compound 94

EXAMPLE 25

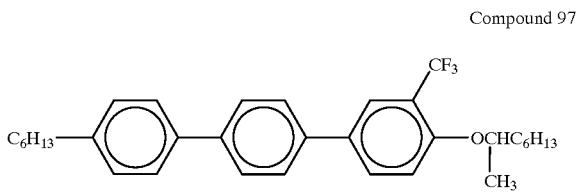
Compound 97

Table 1 illustrates the phase transition temperatures for the compounds of Formula I.

Tables 2–4 show the effect of temperature on spontaneous polarisation (Ps) for example compounds 18, 60 and 46.

TABLE 1

| Compound | Phase Transition Temperature/° C. |
|---|---|
| 17 | K 85.0 ($S_C°$ 71.7) $S_A°$ 126.8 I |
| 18 | K 37.0 $S_C°$ 56.4 $S_A°$ 62.5 I |
| 18a | K 45.1 $S_C°$ 49.5 $S_A°$ 58.7 I |
| 18b | K. 36.2 $S_C°$ 59.2 $S_A°$ 67.6 I |
| 28 | K 67.0 ($S_C°$ 62.0) $S_A°$ 132.9 I |
| 32 | K 39–40 I |
| 33 | K 57.4 $S_C°$ 64.4 N° 69.7 I |
| 37 | K 61.2 $S_C°$ 71.7 I |
| 45 | K 126.5 $S_A°$ 133.3 I |
| 46 | K ? $S_C°$ 52.1 $S_A°$ 64.5 I |
| 55 | K 60.5 ($S_C°$ 58.7) $S_A°$ 68.1 I |
| 59 | K 94.2 $S_C°$ 112.7 $S_A°$ 168.7 I |
| 60 | K 64.9 $S_C°$ 100.2 $S_A°$ 118.8 I |
| 70 | K 65.3 ($S_A°$ 60.0) $S_A°$ 100.1 I |
| 71 | K 71.8 $S_A°$ 153.8 I |
| 72 | K 46.7 $S_C°$ 53.5 $S_A°$ 96.0 I |
| 75 | K 63.5 $S_C°$ 104.1 $S_A°$ 152.6 I |
| 76 | K 60.3 $S_A°$ 105.6 I |
| 77 | K 60.0 $S_C°$ 90.1 $S_A°$ 144.2 I |
| 78 | K 77.8 $S_A°$ 99.6 I |
| 84 | K 39–40 I |
| 94 | K 54.2 $S_C°$ 122.2 $S_A°$ 158.2 I |
| 97 | K 41 I |

It is understood that where the above compounds are optically active, an optically inactive phase can be provided by the same method of synthesis using an optically inactive racemic isomer mixture as starting material. Material 55 has a monotropic $C^*$ phase.

TABLE 2

| Compound 18 | |
|---|---|
| Temp/° C. | Ps nC/cm² |
| 54 | 226 |
| 50 | 336 |
| 44 | 405 |
| 40 | 451 |

TABLE 2-continued

| Compound 18 | |
|---|---|
| Temp/° C. | Ps nC/cm² |
| 34 | 498 |
| 30 | 525 |
| 24 | 550 |

TABLE 3

| Compound 60 | |
|---|---|
| Temp/° C. | Ps nC/cm² |
| 84 | 370 |
| 74 | 440 |
| 64 | 480 |

TABLE 4

| Compound 46 | |
|---|---|
| Temp/° C. | Ps nC/cm² |
| 46 | 65 |
| 45 | 90 |
| 44 | 115 |
| 43 | 135 |
| 42 | 138 |

Ps measurements were made using a Diamant bridge and approximately 6 μm cells that had parallel polyimide alignment.

Compound 70 has a Ps of 230 nC/cm² measured approximately 2° C. into the $S_C^*$ phase.

Compound 45 has a Ps value of approximately 7 nC/cm² at 85° C. This lower value of Ps may be due to the fact that the neighbouring terminal chain results in less steric hindrance with the CN group. It may also be due to the fact that the chiral centre has been moved further away from the core of the molecule.

Compounds 18 and 46 are the same structurally, apart from the fact that there is a CN substituent on compound 46 and a nitro group on compound 18. Replacing the $NO_2$ with the CN group has resulted in a decreased value for Ps and the $S_C^*$ phase stability is less in the CN containing molecule.

Compound 55 has a Ps of 367 nC/cm² at 10° C. below the A–$C^*$ transition.

The $S_C^*$ phase which exists below the $S_A^*$ phase in some of the compounds is advantageous because it allows the formulation of electroclinic mixtures having a $S_C^*$ phase near to this operating temperature range. This $S_C^*$ phase can allow lower voltage operation and/or larger induced tilt angles than could otherwise be attained. A further use of the $S_C^*$ is to provide means for characterising the materials according to the magnitude of their spontaneous polarisation in the $S_C^*$ phase.

It is also possible that the desirable properties outlined earlier in this description can be enhanced at the $S_C^*$–$S_A^*$ transition point thus resulting in a broader working temperature range. Furthermore, devices using materials of Formula I having a $S_C^*$–$S_A^*$ phase sequence may provide both linear or bistable response eg modulation of the temperature of the device.

Figure 20:
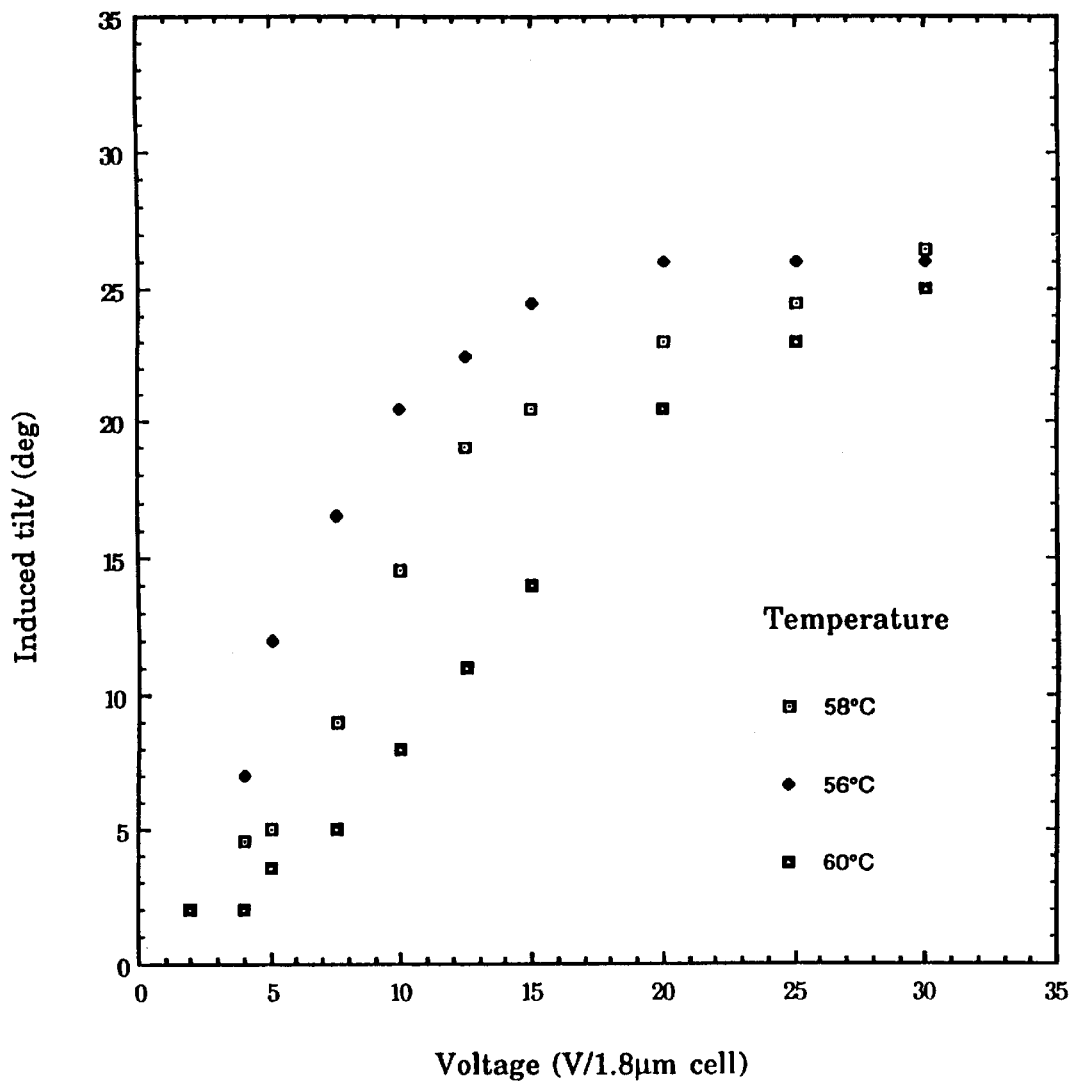
FIG. 20 is a graph of tilt angle/° versus applied voltage/V over a range of temperatures for compound 18.
Figure 21:
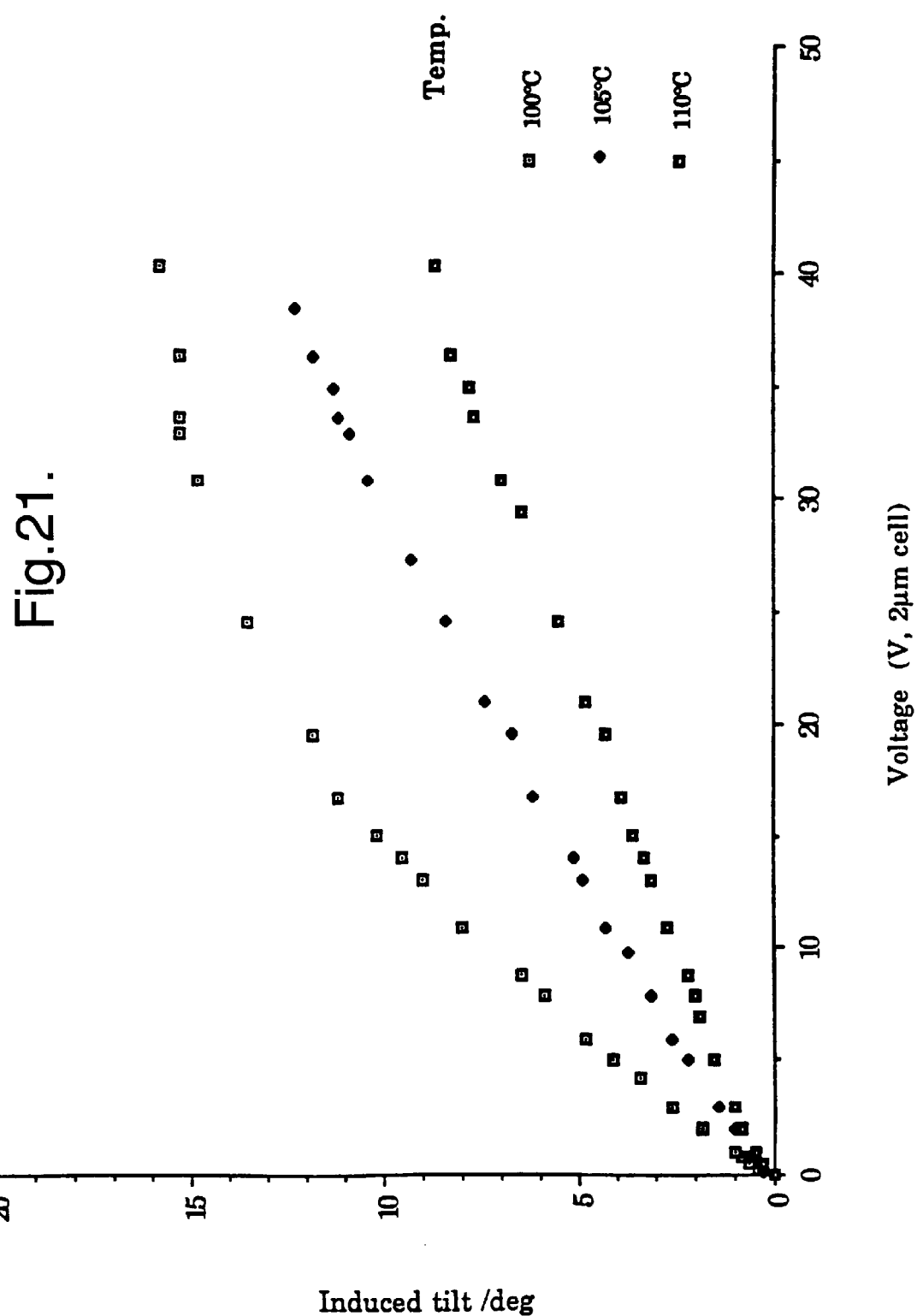
FIG. 21 is a graph of tilt angle/° versus applied voltage/V over a range of temperatures for compound 60.
Figure 22:
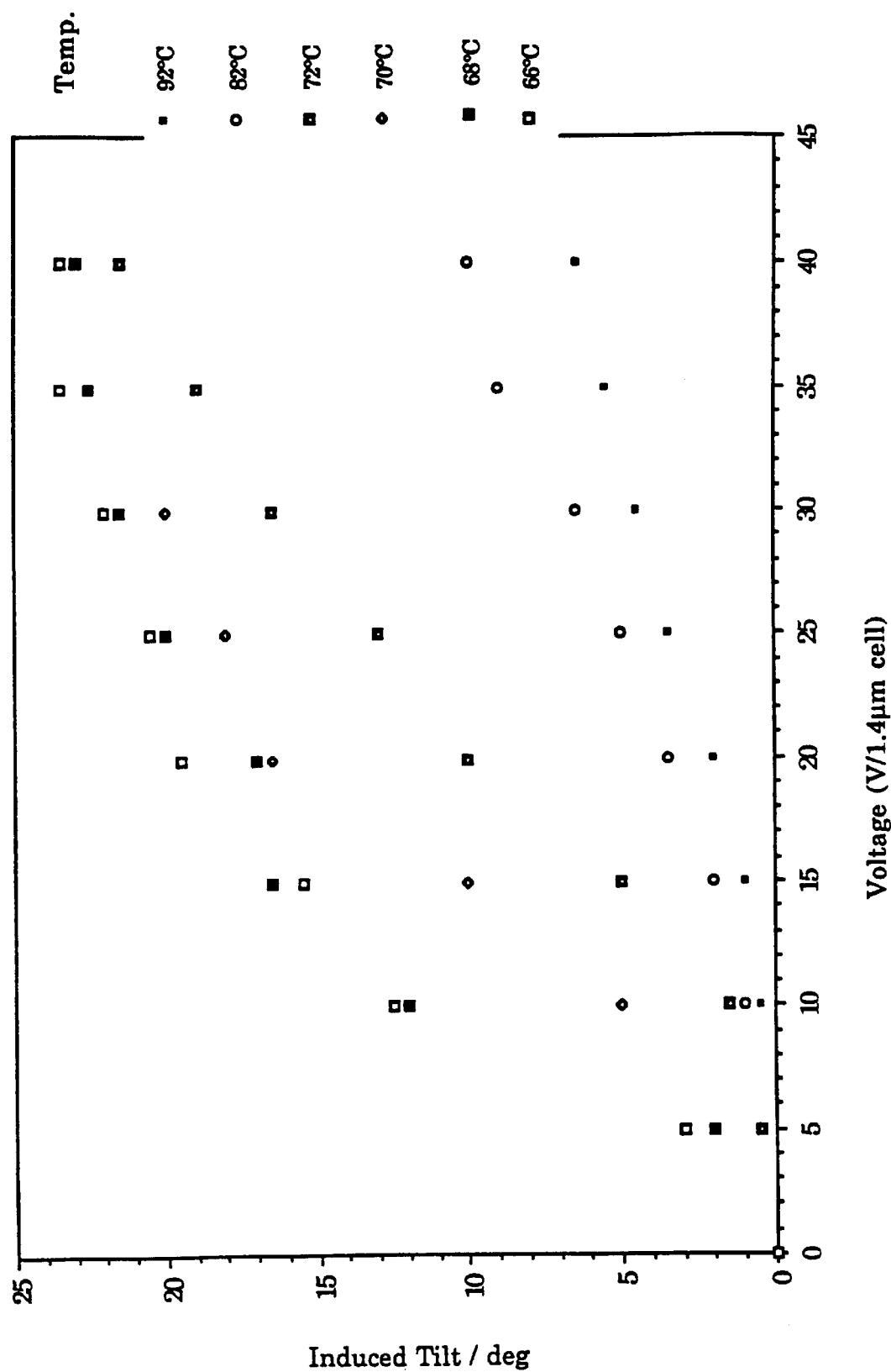
FIG. 22 is a graph of tilt angle/° versus applied voltage/V over a range of temperatures for compound 70.

Graphs of induced tilt versus voltage are illustrated in FIGS. 20–22 for example compounds 18, 60 and 70.

In FIG. 20. Induced tilt/* versus Voltage/V is shown at three different temperatures in a 1.8 μm cell for compound 18.

In FIG. 21. Induced tilt/* versus Voltage/V is shown at four different temperatures in a 2 μm cell for compound 60.

In FIG. 22. Induced tilt/* versus Voltage/V is shown at seven different temperatures in a 1.4 μm cell for compound 70.

Induced tilt values of up to 17° at 62° C. using approximately 15V/μm have been measured for the material illustrated in FIG. 22.

10% of compound 18 was mixed with compound 94. This resulted in the following phase transitions:

K 50.0 $S_C^*$ 114.0 $S_A^*$ 146.0 I

Ps=16.8 nC cm$^{-2}$ at ($T_A^* =_C^* -10°$ C.).

Ps measurements were also made on compounds which had been mixed with the following 1:1:1 mixture H1:

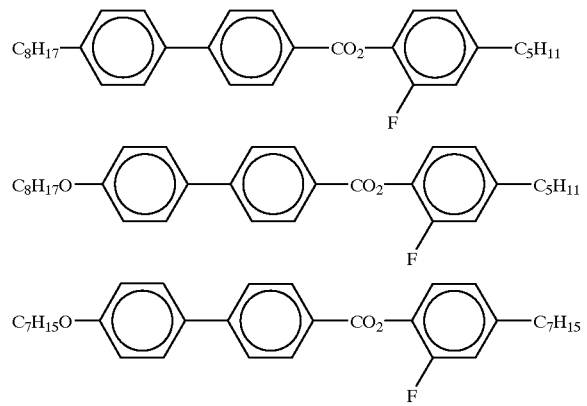

5% of the following compound mixed with H1 resulted in a Ps of 1.3 nC/cm$^2$ at $T_C^* -_A^*$ −10° C.

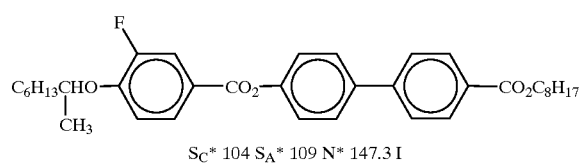

Sc* 104 S$_A$* 109 N* 147.3 I

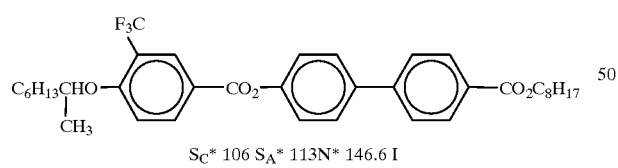

Sc* 106 S$_A$* 113N* 146.6 I

Suitable devices which the materials of the present invention may be incorporated in include beam steerers, piezoelectric actuators or sensors and pyroelectric sensors and displays in general.

The materials of the present invention may also be useful as dopants in ferroelectrics.

The materials of the current invention may be mixed together and/or with other liquid crystal compounds.

The materials of the present invention may also be useful as second order non-linear optic materials for second harmonic conversion of light eg conversion of infra-red semiconductor diode laser to the blue/green region of the spectrum, or the linear electro-optic modulation of light by the Pockels effect. These applications normally require a tilted chiral smectic phase such as $S_C^*$, $S_F^*$ or $S_J^*$ to be present.

Typically such materials may be incorporated into devices comprising two spaced cell walls which are treated on at least one facing surface with an alignment layer. Between the cell walls is a layer of smectic liquid crystal material. There may or may not be electrodes present.

These devices may require electrodes for the application of electric field(s) either perpendicular to, or parallel to the cell normal, this may, for example, aid alignment of the $S_C^*$ material in the device or enable electro-optic modulation. The electrodes may be located on the cell walls and/or within the liquid crystal material itself.

What is claimed is:

1. A compound of the formula:

Formula 1

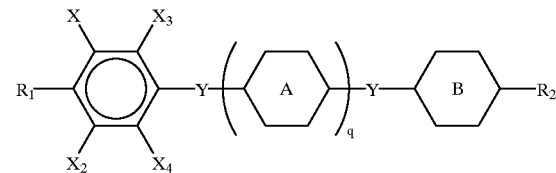

wherein
X is CF$_3$, CF$_2$H, CFH$_2$, hydrogen, alkyl or alkoxy;
X$_2$ is CF$_3$, CF$_2$H, CFH$_2$, hydrogen, alkyl or alkoxy;
X$_3$ is CF$_3$, CF$_2$H, CFH$_2$, hydrogen, alkyl or alkoxy;
X$_4$ is CF$_3$, CF$_2$H, CFH$_2$, hydrogen, alkyl or alkoxy;
A and B are independently phenyl, mono-fluorinated phenyl, di-fluorinated phenyl or cyclohexyl;
Y groups are independently selected from a single bond and C≡C; provided that at least one of the Y groups is a single bond;
q is 0 or 1;
R$_1$ is an end group of the following Formula II:

Formula II

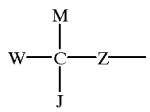

wherein Z is (CH$_2$)$_n$O where n is 0, 1 or 2;
J and M are independently selected from H, C$_{1-4}$ alkyl;
W is C$_1$–C$_{12}$ straight or branched alkyl chain;
provided J, M, W are different; that R$_2$ contains 1–14 carbon atoms wherein one or more non-adjacent CH$_2$ groups may be replaced by O; and further provided that at least one of X or X$_2$ is CF$_3$, CF$_2$H or CFH$_2$.

2. A compound according to claim 1 wherein:
W is C$_1$–C$_8$ straight chain alkyl, n is 0 or 1, M and J are independently chosen from hydrogen, methyl or ethyl;
R$_2$ contains 5–12 carbon atoms wherein one of the CH$_2$ groups may be replaced by O;
q=1;
A and B are both phenyl;
both Ys are single bonds;
one of X or X$_2$ is CF$_3$ the other is H; and
X$_3$=X$_4$=H.

* * * * *